(12) United States Patent
Matthaei et al.

(10) Patent No.: US 11,753,457 B2
(45) Date of Patent: Sep. 12, 2023

(54) SYNOVIAL EXTRACELLULAR MATRIX-SPECIFIC CHIMERIC ANTIGEN RECEPTOR FOR TARGETING REGULATORY T CELLS TO TREAT AUTOIMMUNE DISEASES

(71) Applicants: Sonoma Biotherapeutics, Inc., South San Francisco, CA (US); Curara AB, Stockholm (SE)

(72) Inventors: James Matthaei, South San Francisco, CA (US); Anne-Renee van der Vuurst de Vries, South San Francisco, CA (US); Joshua Beilke, South San Francisco, CA (US); Vivianne Malmström, Stockholm (SE); Kathryn Hooper, South San Francisco, CA (US); Rebecca Johnson, South San Francisco, CA (US); Lars Klareskog, Stockholm (SE)

(73) Assignees: Sonoma Biotherapeutics, Inc., South San Francisco, CA (US); Curara AB, Stockholm (SE)

( * ) Notice: Subject to any disclaimer, the term of this patent is extended or adjusted under 35 U.S.C. 154(b) by 0 days.

(21) Appl. No.: 18/058,162

(22) Filed: Nov. 22, 2022

(65) Prior Publication Data

US 2023/0080155 A1 Mar. 16, 2023

Related U.S. Application Data

(63) Continuation of application No. PCT/US2022/074321, filed on Jul. 29, 2022.

(60) Provisional application No. 63/339,361, filed on May 6, 2022, provisional application No. 63/227,320, filed on Jul. 29, 2021.

(51) Int. Cl.
| | |
|---|---|
| *A61K 39/00* | (2006.01) |
| *C07K 14/725* | (2006.01) |
| *A61P 37/06* | (2006.01) |
| *A61P 19/02* | (2006.01) |
| *A61K 35/17* | (2015.01) |
| *C07K 14/705* | (2006.01) |
| *C07K 16/18* | (2006.01) |
| *C07K 16/36* | (2006.01) |
| *C12N 5/0783* | (2010.01) |
| *C12N 15/62* | (2006.01) |
| *C12N 15/85* | (2006.01) |
| *A61K 38/00* | (2006.01) |

(52) U.S. Cl.
CPC ......... *C07K 14/7051* (2013.01); *A61K 35/17* (2013.01); *A61P 19/02* (2018.01); *A61P 37/06* (2018.01); *C07K 14/70517* (2013.01); *C07K 14/70521* (2013.01); *C07K 16/18* (2013.01); *C07K 16/36* (2013.01); *C12N 5/0636* (2013.01); *C12N 15/625* (2013.01); *C12N 15/85* (2013.01); *A61K 38/00* (2013.01); *A61K 39/00* (2013.01); *C07K 2317/622* (2013.01); *C12N 2501/2302* (2013.01); *C12N 2501/998* (2013.01)

(58) Field of Classification Search
None
See application file for complete search history.

(56) References Cited

U.S. PATENT DOCUMENTS

| | | |
|---|---|---|
| 2016/0024183 A1 | 1/2016 | Shoenfeld et al. |
| 2016/0333422 A1 | 11/2016 | Feldman et al. |
| 2018/0148508 A1 | 5/2018 | Wang et al. |
| 2018/0360884 A1 | 12/2018 | Adusumilli |
| 2019/0263917 A1 | 8/2019 | Qin et al. |
| 2020/0255825 A1 | 8/2020 | Midwood et al. |
| 2020/0277357 A1 | 9/2020 | Klareskog et al. |
| 2020/0330515 A1 | 10/2020 | Maus et al. |
| 2020/0399355 A1 | 12/2020 | Bluestone et al. |
| 2021/0017248 A1 | 1/2021 | Bluestone et al. |
| 2022/0281943 A1 | 9/2022 | Bluestone et al. |

FOREIGN PATENT DOCUMENTS

| | | |
|---|---|---|
| WO | 2009013543 A2 | 1/2009 |
| WO | 2016033331 A1 | 3/2016 |
| WO | 2016090337 A1 | 6/2016 |
| WO | 2017079694 A2 | 5/2017 |
| WO | 2017100428 A1 | 6/2017 |
| WO | 2019152781 A1 | 8/2019 |
| WO | 2019157461 A1 | 8/2019 |
| WO | 2021030257 A1 | 2/2021 |

OTHER PUBLICATIONS

Amara, K. et al. (Mar. 2013). "Monoclonal IgG Antibodies Generated from Joint-derived B cells of RA Patients Have a Strong Bias Toward Citrullinated Autoantigen Recognition," J Exp Med 210(3):445-455. Retracted Dec. 19, 2018.

(Continued)

*Primary Examiner* — Zachary S Skelding
(74) *Attorney, Agent, or Firm* — Morrison & Foerster LLP

(57) ABSTRACT

Disclosed herein are chimeric antigen receptors ("CARs") comprising an antigen binding site that recognizes citrullinated polypeptides. Citrullinated polypeptides, such as citrullinated vimentin, fibrinogen, and filaggrin, are expressed in the synovium of subjects with rheumatoid arthritis. Further disclosed are T cells, and in particular, Treg cells, that express these CARs. Administration of these CAR-T cells is useful in the treatment of rheumatoid arthritis as well as other diseases associated with citrullinated peptides.

30 Claims, 30 Drawing Sheets
Specification includes a Sequence Listing.

(56) References Cited

OTHER PUBLICATIONS

Burmester, G.R. et al. (Jun. 2017). "Novel Treatment Strategies in Rheumatoid Arthritis," Lancet 389(10086):2338-2348.
Feitsma, A.L. et al. (Jan. 2010). "Identification of Citrullinated Vimentin Peptides as T Cell Epitopes in HLA-DR4-Positive Patients with Rheumatoid Arthritis," Arthritis and Rheumatism 62(1):117-125.
Oldham, R.A.A. et al. (Aug. 2017). "Practical Considerations for Chimeric Antigen Receptor Design and Delivery," Expert Opin Biol Ther. 17(8):961-978.
Posey Jr., A.D. et al. (Jun. 2016). "Engineered CAR T Cells Targeting the Cancer-Associated Tn-Glycoform of the Membrane Mucin MUC1 Control Adenocarcinoma," Immunity 44(6):1444-1454.
Raffin, C. et al. (Mar. 2020). "T-reg Cell-based Therapies: Challenges and Perspectives," Nature Reviews Immunology 20(3):158-172.
Raffin, C. et al. (May 2016). "Development of Citrullinated-vimentin-specific CAR for Targeting Tregs to Treat Autoimmune Rheumatoid Arthritis," J Immunol 196 (1 Supplement):210.19, 2 pages. Abstract only.
Raffin, C. et al. (May 2018). "Development of Citrullinated-vimentin-specific CAR for Targeting Tregs to Treat Autoimmune Rheumatoid Arthritis," J Immunol 200 (1 Supplement):176.17, 3 pages. Abstract only.
Sahlstrom, P. et al. (Oct. 2020). "Different Hierarchies of Anti-modified Protein Autoantibody Reactivities in Rheumatoid Arthritis," Arthritis Rheumatology 72(10):1643-1657. Supplementary material attached.
Steen, J. et al. (Feb. 2019). "Recognition of Amino Acid Motifs, rather than Specific Proteins, by Human Plasma Cell-derived Monoclonal Antibodies to Posttranslationally Modified Proteins in Rheumatoid Arthritis," Arthritis Rheumatology 71(2):196-209. Supplementary material attached.
Wang, Y. et al. (Dec. 2017). "New Chimeric Antigen Receptor Design for Solid Tumors," Frontiers in Immunology 8:1934, 9 pages.
International Search Report and Written Opinion dated Jan. 5, 2023, for PCT Application No. PCT/US22/74321, filed on Jul. 29, 2022, 15 pages.

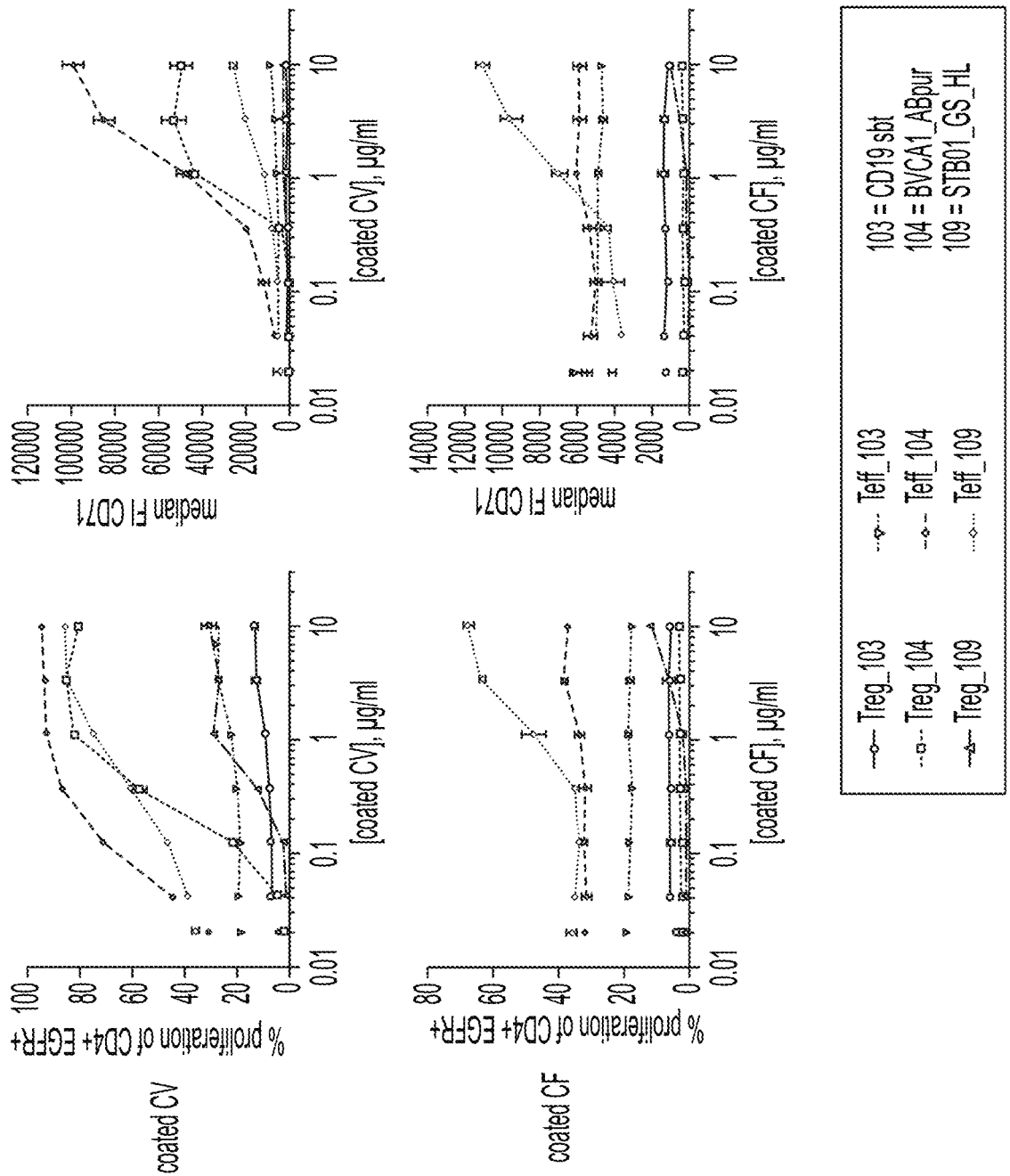

SYNOVIAL EXTRACELLULAR MATRIX-SPECIFIC CHIMERIC ANTIGEN RECEPTOR FOR TARGETING REGULATORY T CELLS TO TREAT AUTOIMMUNE DISEASES

CROSS REFERENCE TO RELATED APPLICATIONS

This application is a continuation of PCT/US2022/074321 filed on Jul. 29, 2022 which claims the benefit of U.S. Provisional Application No. 63/227,320, filed Jul. 29, 2021, and U.S. Provisional Application No. 63/339,361, filed May 6, 2022, each of which is hereby incorporated by reference in its entirety.

REFERENCE TO AN ELECTRONIC SEQUENCE LISTING

The content of the electronic sequence listing (237752000301SEQLIST.xml; Size: 50,876 bytes; and Date of Creation: Nov. 17, 2022) is herein incorporated by reference in its entirety.

FIELD

The present disclosure relates to chimeric antigen receptors reactive with citrullinated antigens and regulatory T cells expressing the receptors for treating autoimmune disease.

BACKGROUND

Autoimmune diseases affect a significant number of people. For example. Rheumatoid Arthritis (RA) is a chronic inflammatory disease targeting peripheral joints leading to bone erosion, impairment of mobility, and decreased quality of life. It is affecting 0.5-1% of the population worldwide and the incidence rate keeps rising. The pathogenesis of RA is mainly localized in the synovial joint where immune cells composed of T cells, B cells, macrophages, and dendritic cells infiltrate the synovium. Moreover, fibroblast-like synoviocytes present in the sublining layer of the synovium proliferate and contribute to cartilage damage.

Synovial hyperplasia in rheumatoid arthritis results in infiltration of the synovium by immune cells, and subsequent cartilage damage and bone erosion.

Currently there is no cure for RA as well as for many other autoimmune conditions. Lifelong treatment is usually required for patients with RA, which in addition of being extremely expensive, may cause severe side effects in the long term such as infections and rheumatoid arthritis risk.

BRIEF DESCRIPTION OF THE DRAWINGS

The accompanying drawings, which are incorporated herein and form a part of the specification, illustrate exemplary embodiments and, together with the description, further serve to enable a person skilled in the pertinent art to make and use these embodiments and others that will be apparent to those skilled in the art. The invention will be more particularly described in conjunction with the following drawings wherein:

FIG. 9 SBT01G CAR as effectors and Tregs respond to Citrullinated Fibrinogen but BVCA1 does not.

FIG. 16A shows that CV-CAR Treg cells are able to suppress proliferation of CD3/CD28-pre-activated Teff cells in the presence but not the absence of CV. FIG. 16B shows that CV-CAR Treg cells are able to suppress proliferation of CD19-CAR Teff cells in the presence of CV, whereas untransduced Treg cells are not.

FIG. 18A shows how a proliferation ratio of the CV-CAR Tregs (EGFR-+) was determined. Specifically, the proliferation ratio equals the % of EGFR+, CTV− cells divided by the % of EGFR+, CTV− cells. FIG. 18B shows how a fold change in EGFR ratio was determined.

FIG. 19A shows the absolute number of CD45+, CD3+ Tregs in the lungs of various study groups, while FIG. 19B shows the proliferation ratio of the Tregs in the lungs of various study groups.

SUMMARY

Figure 1:
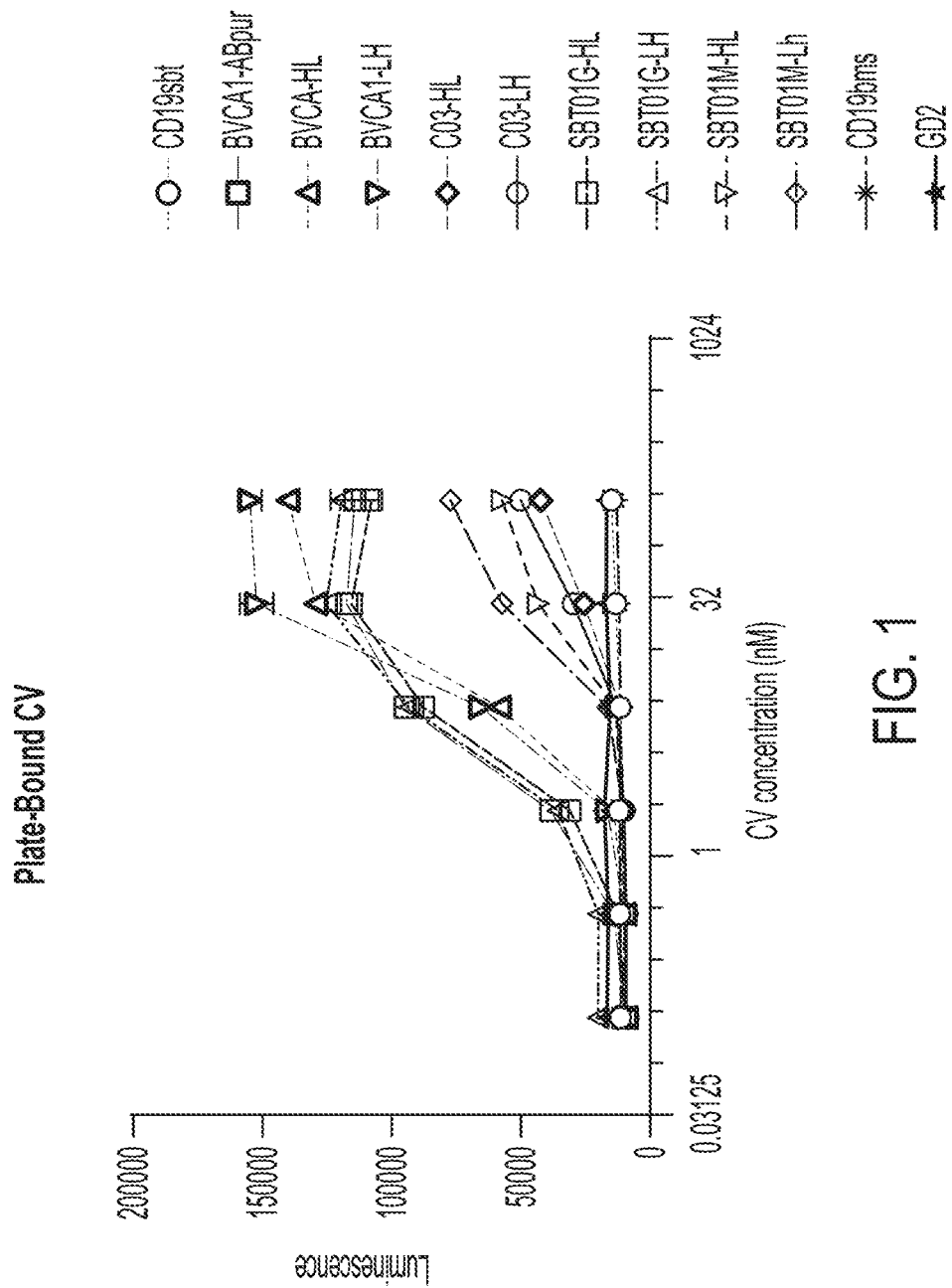
FIG. 1: Initial data comprising an MND promoter and EGFRt backbone showed that CV CARs BVCA1 and SBT01G had strongest response to plate-bound full-length CV (n=2).

Regulatory T cells (Tregs) are defective in patients and mouse models of RA. Therefore, Treg-based adoptive cell therapy (ACT) represents a promising approach in RA. In fact, Treg-based ACT reverses disease in animal models of RA. In this study, an antibody isolated from a RA patient was used to engineer a CAR specific for citrullinated vimentin (CV) and other posttranslational modified proteins found abundantly and almost exclusively in the synovial extracellular matrix (ECM) of affected joints.

Disclosed herein are chimeric antigen receptors (CAR) which specifically recognize antigens associated with autoimmune diseases. In particular, the CARs can be specific for post-translationally modified antigens. In particular, the CARs can be specific for binding to citrullinated polypeptides, including vimentin, citrullinated filaggrin and citrullinated fibrinogen.

Chimeric antigen receptors (CAR) were engineered to specifically target post-translationally modified proteins, namely citrullinated vimentin, citrullinated filaggrin and citrullinated fibrinogen, that are expressed in the extracellular matrix of inflamed joints in patients with Rheumatoid Arthritis (RA). In some embodiments, the single chain fragment variable (scFv) part of the CAR is obtained from an antibody highly specific for citrullinated proteins isolated from the peripheral blood of an RA patient. In one embodiment, specific scFv chains were inserted into a second-generation CAR construct. In some embodiments, the scFv chains were inserted into a CAR construct cloned in a lentiviral vector. In the detailed description, references to antibodies are applicable to antigen-binding domains of the CARs of the present disclosure unless the context indicates otherwise.

DETAILED DESCRIPTION

I. Definitions

Unless otherwise specified, terms and symbols of biochemistry, nucleic acid chemistry, molecular biology, developmental biology and molecular genetics follow those of standard treaties and texts in the field, for example, Sambrook et al, Molecular Cloning: A Laboratory Manual, 2nd Edition (Cold Spring Harbor Press, 1989); Alberts and Singer, Developmental Biology, Eighth Edition (Sinauer Associates Inc., Sunderland, Mass., 2006); Kornberg and Baker, DNA Replication, Second Edition (W.H. Freeman, New York, 1992); Gaits, ed., Oligonucleotide Synthesis: A Practical Approach (IRL Press, Oxford, 1984); Lehninger, Biochemistry, Second Edition (Worth Publishers, New York, 1975); Eckstein, ed., Oligonucleotides and Analogs: A Practical Approach (Oxford University Press, New York, 1991); and the like.

As used herein, the terms "antigen," "immunogen," and "antibody target," refer to a molecule, compound, or complex that is recognized by an antibody, i.e., can be bound by the antibody. The term can refer to any molecule that can be recognized by an antibody, e.g., a polypeptide, polynucleotide, carbohydrate, lipid, chemical moiety, or combinations thereof (e.g., phosphorylated or glycosylated polypeptides, etc.). One of skill will understand that the term does not indicate that the molecule is immunogenic in every context, but simply indicates that it can be targeted by an antibody.

As used herein, the term "epitope" refers to the localized site on an antigen that is recognized and bound by an antibody. Epitopes can include a few amino acids or portions of a few amino acids, e.g., 5 or 6, or more, e.g., 20 or more amino acids, or portions of those amino acids. In some cases, the epitope includes non-protein components, e.g., from a carbohydrate, nucleic acid, or lipid. In some cases, the epitope is a three-dimensional moiety. Thus, for example, where the target is a protein, the epitope can be comprised of consecutive amino acids, or amino acids from different parts of the protein that are brought into proximity by protein folding (e.g., a discontinuous epitope).

As used herein, the term "antibody" refers to a polypeptide comprising a framework region from an immunoglobulin gene, that specifically bind and recognize an antigen. Typically, the "variable region" contains the antigen-binding region of the antibody (or its functional equivalent) and is most critical in specificity and affinity of binding. An exemplary immunoglobulin (antibody) structural unit comprises a tetramer. Each tetramer is composed of two identical pairs of polypeptide chains, each pair having one "light" (about 25 kD) and one "heavy" chain (about 50-70 kD).

Antibodies can be of (i) any of the five major classes of immunoglobulins, based on the identity of their heavy-chain constant domains—alpha (IgA), delta (IgD), epsilon (IgE), gamma (IgG) and mu (IgM), or (ii) subclasses (isotypes) thereof (E.g., IgG1, IgG2, IgG3, IgG4, IgA1 and IgA2). The light chains can be either lambda or kappa.

The following are a non-exhaustive list of different antibody forms, all retaining antigen binding activity:
 (1) whole immunoglobulins (also referred to as "intact" antibodies) (two light chains and two heavy chains, e.g., a tetramer);
 (2) an immunoglobulin polypeptide (a light chain or a heavy chain);
 (3) an antibody fragment, such as Fv (a monovalent or bi-valent variable region fragment, and can encompass only the variable regions (e.g., $V_L$ and/or $V_H$), Fab ($V_L C_L$ $V_H C_H$), F(ab')2, Fv ($V_L V_H$), scFv (single chain Fv) (a polypeptide comprising a $V_L$ and $V_H$ joined by a linker, e.g., a peptide linker), (scFv)2, sc(Fv)2, bispecific sc(Fv)2, bispecific (scFv)2, minibody (sc(FV)2 fused to CH3 domain), diabody (noncovalent dimer of single-chain Fv (scFv) fragment that consists of the heavy chain variable (VH) and light chain variable (VL) regions connected by a small peptide linker), triabody is trivalent sc(Fv)3 or trispecific sc(Fv)3;
 (4) a multivalent antibody (an antibody comprising binding regions that bind two different epitopes or proteins, e.g., "scorpion" antibody;
 (5) a fusion protein comprising a binding portion of an immunoglobulin fused to another amino acid sequence (such as a fluorescent protein); and
 (6) heavy chain only antibody or antibody fragment having only two heavy chains and lacking the two light chains usually found in antibodies.

Production and properties of tandem scFvs and diabodies are described, e.g., in Asano et al. (2011) J Biol. Chem. 286:1812; Kenanova et al. (2010) Prot Eng Design Sel 23:789; Asano et al. (2008) Prot Eng Design Sel 21:597.

The phrase "CDR sequence set" as used herein refers to the 3 heavy chain and/or 3 light chain CDRs of a particular antibody described herein. A "light chain" CDR sequence set refers to the light chain CDR sequences. A "heavy chain" CDR sequence set refers to the heavy chain CDR sequences.

A "full" CDR sequence set refers to both heavy chain and light chain CDR sequences. CDRs are predicted based on IMGT sequence alignment.

As used herein, the term "chimeric antibody" refers to an antibody having amino acid sequences derived from two or more species. In one embodiment, the variable region of both light and heavy chains correspond to the variable region of antibodies derived from one species of mammal (e.g., mouse, rat, rabbit, etc.) with the desired specificity, affinity and capability, while the constant region are homologous the sequence derived from another species (typically in the subject receiving the therapy, e.g., human) to avoid eliciting an immune response.

As used herein, the term "humanized antibody" refers to a chimeric antibody in which the CDRs, obtained from the VH and VL regions of a non-human antibody having the desired specificity, affinity and capability are grafted to a human framework sequence. In one embodiment, the framework residues of the humanized antibody are modified to refine and optimize the antibody specificity, affinity and capability. Humanization, i.e., substitution of non-human CDR sequences for the corresponding sequences of a human antibody, can be performed following the methods described in, e.g., U.S. Pat. Nos. 5,545,806; 5,569,825; 5,633,425; 5,661,016; Riechmann et al., Nature 332:323-327 (1988); Marks et al., Bio/Technology 10:779-783 (1992); Morrison, Nature 368:812-13 (1994); Fishwild et al., Nature Biotechnology 14:845-51 (1996).

As used herein, the term "human antibody" refers to an antibody produced by a human or an antibody having an amino acid sequence corresponding thereto made by any technique known in the art.

The specificity of the binding can be defined in terms of the comparative dissociation constants (Kd) of the antibody (or other targeting moiety) for target, as compared to the dissociation constant with respect to the antibody and other materials in the environment or unrelated molecules in general. A larger (higher) Kd is a Kd that describes a lower affinity interaction. Conversely a smaller (lower) Kd is a Kd that describes a higher affinity interaction or tighter binding. By way of example only, the Kd for an antibody specifically binding to a target may be femtomolar, picomolar, nanomolar, or micromolar and the Kd for the antibody binding to unrelated material may be millimolar or higher. Binding affinity can be in the micromolar range (kD=$10^{-4}$ to $10^{-6}$), nanomole range (kD=$10^{-7}$ M to $10^{-9}$ M), picomole range (kD=$10^{-10}$ M to $10^{-12}$ M), or femtomole range (kD=$10^{-13}$ M to $10^{-15}$ M).

As used herein, an antibody "binds" or "recognizes" an antigen or epitope if it binds the antigen or epitope with a Kd of less than $10^{-4}$M (i.e., in the micromolar range). The term "binds" with respect to a cell type (e.g., an antibody that binds cancer cells), typically indicates that an agent binds a majority of the cells in a pure population of those cells. For example, an antibody that binds a given cell type typically binds to at least ⅔ of the cells in a population of the indicated cells (e.g., 67, 75, 80, 85, 90, 91, 92, 93, 94, 95, 96, 97, 98, 99, or 100%). In some cases, binding to a polypeptide can be assayed by comparing binding of the antibody to a cell that presents the polypeptide to binding (or lack thereof) of the antibody to a cell that does not express the polypeptide. One of skill will recognize that some variability will arise depending on the method and/or threshold of determining binding. Affinity of an antibody for a target can be determined according to methods known in the art, e.g., as reviewed in Ernst et al. Determination of Equilibrium Dissociation Constants, Therapeutic Monoclonal Antibodies (Wiley & Sons ed. 2009).

As used herein, the term "greater affinity" as used herein refers to a relative degree of antibody binding where an antibody X binds to target Y more strongly (Kon) and/or with a smaller dissociation constant (Koff) than to target Z, and in this context antibody X has a greater affinity for target Y than for Z. Likewise, the term "lesser affinity" herein refers to a degree of antibody binding where an antibody X binds to target Y less strongly and/or with a larger dissociation constant than to target Z, and in this context antibody X has a lesser affinity for target Y than for Z. The affinity of binding between an antibody and its target antigen, can be expressed as KA equal to 1/KD where KD is equal to kon/koff. The kon and koff values can be measured using surface plasmon resonance technology, for example, using a Molecular Affinity Screening System (MASS-1) (Sierra Sensors GmbH, Hamburg, Germany). An antagonist or blocking antibody is an antibody that partially or fully blocks inhibits or neutralizes a biological activity related to the target antigen relative to the activity under similar physiological conditions when the antibody is not present. Antagonists can be competitive, non-competitive or irreversible. A competitive antagonist is a substance that binds to a natural ligand or receptor at the same site as the natural ligand-receptor interaction or binds allosterically in a manner that induces a change to prevent normal binding. A non-competitive antagonist binds at a different site than the natural ligand-receptor interaction, but lower the KD or signal resulting from the interaction. An irreversible inhibitor causes covalent modifications to the receptor preventing any subsequent binding.

As used herein, the term "avidity" refers to the overall stability of the binding complex between the antibody and the target antigen. It is governed by three factors, (i) the intrinsic affinity of the antibody for the antigen, (2) the valency of the antibody, and (3) the geometric arrangement of the interacting components. Affinity is the strength of the interaction between the antibody and a single target, whereas avidity is an accumulated strength of multiple affinities. In one embodiment, the antibodies provided herein are divalent.

As used herein, an antibody "preferentially binds" binds a first antigen relative to a second antigen if it binds the first antigen with greater affinity than it does the second antigen. Preferential binding can be at least any of 2-fold, 5-fold, 9-fold, 10-fold, 20-fold, 30-fold, 40-fold, 50-fold, 100-fold, 500-fold or 1000-fold greater affinity.

As used herein, an antibody "specifically binds" or is "specific for" a target antigen or target group of antigens if it binds the target antigen or each member of the target group of antigens with an affinity of at least any of $1\times10^{-6}$ M, $1\times10^{-7}$ M, $1\times10^{-8}$ M, $1\times10^{-9}$ M, $1\times10^{-10}$ M, $1\times10^{-11}$ M, $1\times10^{-12}$ M, and, for example, binds to the target antigen or each member of the target group of antigens with an affinity that is at least two-fold greater than its affinity for non-target antigens to which it is being compared. Typically, specific binding is characterized by binding the antigen with sufficient affinity that the antibody is useful as a diagnostic to detect the antigen or epitope and/or as a therapeutic agent in targeting the antigen or epitope.

As used herein, the term "polypeptide" refers to a molecule having a sequence of natural and/or unnatural amino acids connected through peptide bonds. The term "peptide" refers to a short polypeptide, typically no more than 30 amino acids long. The amino acid sequence of a polypeptide is referred to as its "primary structure." The term "protein"

refers to a polypeptide having a secondary, tertiary and/or quaternary structure, e.g., structures stabilized by hydrogen bonds, relationships between secondary structures and structures formed of more than one protein. Proteins can be further modified by other attached moieties such as carbohydrate (glycoproteins), lipids (lipoproteins) phosphate groups (phosphoproteins) and the like.

As used herein, an amino acid sequence "consists of" only the amino acids in that sequence.

As used herein, a first amino acid sequence "consists essentially of" a second amino acid sequence if the first amino acid sequence (1) comprises the second amino sequence and (2) is no more than 1, no more than 2 or no more than 3 amino acids longer than the second amino acid sequence.

As used herein, a first amino acid sequence is a "fragment" of a second amino acid sequence if the second amino acid sequence comprises the first amino acid sequence. In certain embodiments, a first amino acid sequence that is a fragment of a second amino acid sequence may have no more than any of 1, 2, 3, 4, 5, 6, 7, 8, 9 or 10 fewer amino acids than the second amino acid sequence.

As used herein, a "functional equivalent" of a reference amino acid sequence is a sequence that is not identical to the reference sequence, but that contains minor alterations such as, for example, insertion, deletion or substitution of one or a few amino acids. A functionally equivalent sequence retains the function (e.g., immunogenicity) of the reference sequence to which it is equivalent. If a functionally equivalent amino acid sequence contains substitution of one or more amino acids with respect to the reference sequence, these will generally be conservative amino acid substitutions.

As used herein, a "conservative amino acid substitution" is one in which one amino acid residue is replaced with another amino acid residue without abolishing the protein's desired properties. Suitable conservative amino acid substitutions can be made by substituting amino acids with similar hydrophobicity, polarity, and R-chain length for one another. See, e.g., Watson, et al., "Molecular Biology of the Gene," 4th Edition, 1987, The Benjamin/Cummings Pub. Co., Menlo Park, Calif., p. 224. Examples of conservative amino acid substitution include the following (Note, some categories are not mutually exclusive):

| Conservative Substitutions | |
|---|---|
| Type of Amino Acid | Substitutable Amino Acids |
| Hydrophilic | Ala, Pro, Gly, Glu, Asp, Gln, Asn, Ser, Thr |
| Sulphydryl | Cys |
| Aliphatic (non-polar, hydrophobic) | Ala, Val, Ile, Leu, Met, Gly, Pro |
| Basic | Lys, Arg, His |
| Aromatic | Phe, Tyr, Trp |

As used herein, the term "substantially identical" refers to identity between a first amino acid sequence that contains a sufficient or minimum number of amino acid residues that are i) identical to, or ii) conservative substitutions of aligned amino acid residues in a second amino acid sequence such that the first and second amino acid sequences have a common structural domain and/or common functional activity and/or common immunogenicity. For example, amino acid sequences that contain a common structural or antigenic domain having at least about 90%, 91%, 92%, 93%, 94%, 95%, 96%, 97%, 98% or 99% identity are termed sufficiently or substantially identical. In the context of nucleotide sequence, the term "substantially identical" is used herein to refer to a first nucleic acid sequence that contains a sufficient or minimum number of nucleotides that are identical to aligned nucleotides in a second nucleic acid sequence such that the first and second nucleotide sequences encode a polypeptide having common functional activity, or encode a common structural polypeptide domain or a common functional polypeptide activity, or encode polypeptides having the same immunogenic properties.

As used herein, a chemical entity, such as a polypeptide, is "substantially pure" or "isolated" if it is the predominant chemical entity of its kind (e.g., of polypeptides) in a composition. This includes the chemical entity representing more than 50%, more than 80%, more than 90%, more than 95%, more than 98%, more than 99%, more than 99.5%, more than 99.9%, or more than 99.99% of the chemical entities of its kind in the composition. A substantially purified fraction is a composition wherein the object species comprises at least about 50% (on a molar basis) of all macromolecular species present. Generally, a substantially pure composition means that about 80% to 90% or more of the macromolecular species present in the composition is the purified species of interest. The object species is purified to essential homogeneity (contaminant species cannot be detected in the composition by conventional detection methods) if the composition consists essentially of a single macromolecular species. Solvent species, small molecules, stabilizers (e.g., BSA), and elemental ion species are not considered macromolecular species for purposes of this definition.

The phrase "isolated antibody" refers to antibody produced in vivo or in vitro that has been removed from the source that produced the antibody, for example, an animal, hybridoma or other cell line (such as recombinant insect, yeast or bacterial cells that produce antibody).

The term "sequence identity" as used herein refers to the percentage of sequence identity between two polypeptide sequences or two nucleic acid sequences. To determine the percent identity of two amino acid sequences or of two nucleic acid sequences, the sequences are aligned for optimal comparison purposes (e.g., gaps can be introduced in the sequence of a first amino acid or nucleic acid sequence for optimal alignment with a second amino acid or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., identity=number of identical overlapping positions/total number of positions.times.100%). In one embodiment, the two sequences are the same length. The determination of percent identity between two sequences can also be accomplished using a mathematical algorithm. A preferred, non-limiting example of a mathematical algorithm utilized for the comparison of two sequences is the algorithm of Karlin and Altschul, 1990, Proc. Natl. Acad. Sci. U.S.A. 87:2264-2268, modified as in Karlin and Altschul, 1993, Proc. Natl. Acad. Sci. U.S.A. 90:5873-5877. Such an algorithm is incorporated into the NBLAST and XBLAST programs of Altschul et al., 1990, J. Mol. Biol. 215:403. BLAST nucleotide searches can be performed with the NBLAST nucleotide program parameters set, e.g., for score=100, word-length=12 to obtain nucleotide sequences homologous to a nucleic acid molecules of the present application. BLAST protein searches can be performed with the XBLAST program parameters set, e.g., to score-50, wordlength=3 to obtain amino acid sequences homologous to a protein molecule described herein. To obtain gapped alignments for comparison purposes, Gapped BLAST can be utilized as described in Altschul et al., 1997, Nucleic Acids Res. 25:3389-3402. Alternatively, PSI-BLAST can be used to perform an iterated search which detects distant relationships between molecules (Id.). When utilizing BLAST, Gapped BLAST, and PSI-Blast programs, the default parameters of the respective programs (e.g., of XBLAST and NBLAST) can be used (see, e.g., the NCBI website). Another preferred, non-limiting example of a mathematical algorithm utilized for the comparison of sequences is the algorithm of Myers and Miller, 1988, CABIOS 4:11-17. Such an algorithm is incorporated in the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. The percent identity between two sequences can be determined using techniques similar to those described above, with or without allowing gaps. In calculating percent identity, typically only exact matches are counted.

For antibodies, percentage sequence identities can be determined when antibody sequences maximally aligned by IMGT. After alignment, it a subject antibody region (e.g., the entire mature variable region of a heavy or light chain) is being compared with the same region of a reference antibody, the percentage sequence identity between the subject and reference antibody regions is the number of positions occupied by the same amino acid in both the subject and reference antibody region divided by the total number of aligned positions of the two regions, multiplied by 100 to convert to percentage.

Percent amino acid sequence identity may also be determined using the sequence comparison program NCBI-BLAST2 (Altschul et al., Nucleic Acids Res. 25:3389-3402 (1997)). The NCBI-BLAST2 sequence comparison program may be obtained from the National Institute of Health, Bethesda, Md. NCBI-BLAST2 uses several search parameters, wherein all of those search parameters are set to default values including, for example, unmask=yes, strand=all, expected occurrences=10, minimum low complexity length=15/5, multi-pass e-value=0.01, constant for multi-pass=25, dropoff for final gapped alignment=25 and scoring matrix=BLOSUM62.

In situations where NCBI-BLAST2 is employed for amino acid sequence comparisons, the amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows: 100 times the fraction X/Y, where X is the number of amino acid residues scored as identical matches by the sequence alignment program NCBI-BLAST2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. The term "nucleic acid sequence" as used herein refers to a sequence of nucleoside or nucleotide monomers consisting of naturally occurring bases, sugars and intersugar (backbone) linkages and includes cDNA. The term also includes modified or substituted sequences comprising non-naturally occurring monomers or portions thereof. The nucleic acid sequences of the present application may be deoxyribonucleic acid sequences (DNA) or ribonucleic acid sequences (RNA) and may include naturally occurring bases including adenine, guanine, cytosine, thymidine and uracil. The sequences may also contain modified bases. Examples of such modified bases include aza and deaza adenine, guanine, cytosine, thymidine and uracil; and xanthine and hypoxanthine. It is understood that polynucleotides comprising non-transcribable nucleotide bases may be useful as probes in, for example, hybridization assays. The nucleic acid can be either double stranded or single stranded, and represents the sense or antisense strand. Further, the term "nucleic acid" includes the complementary nucleic acid sequences as well as codon optimized or synonymous codon equivalents.

The term "isolated nucleic acid" as used herein refers to a nucleic acid substantially free of cellular material or culture medium when produced by recombinant DNA techniques, or chemical precursors, or other chemicals when chemically synthesized. An isolated nucleic acid is also substantially free of sequences that naturally flank the nucleic acid (i.e. sequences located at the 5' and 3' ends of the nucleic acid) from which the nucleic acid is derived.

Hybridization may occur to all or a portion of a nucleic acid sequence molecule. The hybridizing portion is typically at least 15 (e.g. 20, 25, 30, 40 or 50) nucleotides in length. Those skilled in the art will recognize that the stability of a nucleic acid duplex, or hybrids, is determined by the Tm, which in sodium containing buffers is a function of the sodium ion concentration and temperature (Tm=81.5° C.−16.6 (Log 10 [Na+])+0.41(%(G+C)−600/I), or similar equation). Accordingly, the parameters in the wash conditions that determine hybrid stability are sodium ion concentration and temperature. In order to identify molecules that are similar, but not identical, to a known nucleic acid molecule a 1% mismatch may be assumed to result in about a 1° C. decrease in Tm, for example, if nucleic acid molecules are sought that have a >95% identity, the final wash temperature will be reduced by about 5° C. Based on these considerations those skilled in the art will be able to readily select appropriate hybridization conditions. In preferred embodiments, stringent hybridization conditions are selected. By way of example the following conditions may be employed to achieve stringent hybridization: hybridization at 5× sodium chloride/sodium citrate (SSC)/5× Denhardt's solution/1.0% SDS at Tm−5° C. based on the above equation, followed by a wash of 0.2×SSC/0.1% SDS at 60° C. Moderately stringent hybridization conditions include a washing step in 3×SSC at 42° C. It is understood, however, that equivalent stringencies may be achieved using alternative buffers, salts and temperatures. Additional guidance regarding hybridization conditions may be found in: Current Protocols in Molecular Biology, John Wiley & Sons, N.Y., 2002, and in: Sambrook et al., Molecular Cloning: A Laboratory Manual, Cold Spring Harbor Laboratory Press, 2001.

As used herein, the term "expression construct" refers to a polynucleotide comprising an expression control sequence operatively linked with a heterologous nucleotide sequence (i.e., a sequence to which the expression control sequence is not normally connected to in nature) that is to be the subject of expression. As used herein, the term "expression vector" refers to a polynucleotide comprising an expression construct and sequences sufficient for replication in a host cell or insertion into a host chromosome. Plasmids and viruses are examples of expression vectors. As used herein, the term "expression control sequence" refers to a nucleotide sequence that regulates transcription and/or translation of a nucleotide sequence operatively linked thereto. Expression control sequences include promoters, enhancers, repressors (transcription regulatory sequences) and ribosome binding sites (translation regulatory sequences).

As used herein, a nucleotide sequence is "operatively linked" with an expression control sequence when the expression control sequence functions in a cell to regulate transcription of the nucleotide sequence. This includes promoting transcription of the nucleotide sequence through an interaction between a polymerase and a promoter.

The term "vector" as used herein comprises any intermediary vehicle for a nucleic acid molecule which enables said nucleic acid molecule, for example, to be introduced into prokaryotic and/or eukaryotic cells and/or integrated into a genome, and include plasmids, phagemids, bacteriophages or viral vectors such as retroviral based vectors, lentiviral vectors, Adeno Associated viral vectors and the like. The term "plasmid" as used herein generally refers to a construct of extrachromosomal genetic material, usually a circular DNA duplex, which can replicate independently of chromosomal DNA.

"Transfection" refers to the introduction of new genetic material into a cell. It includes transformation (the direct uptake and incorporation of exogenous genetic material from its surroundings through the cell membrane), transduction (the introduction of foreign DNA by a bacteriophage virus into a host cell) and conjugation.

As used herein, a "host cell" refers to a recombinant cell comprising an expression construct.

As used herein, the term "biological sample" refers to a sample containing cells (e.g., tumor cells) or biological molecules derived from cells.

As used herein, the term terms "therapy," "treatment," "therapeutic intervention" and "amelioration" refer to any activity resulting in a reduction in the severity of symptoms. The terms "treat" and "prevent" are not intended to be absolute terms. Treatment and prevention can refer to any delay in onset, amelioration of symptoms, improvement in patient survival, increase in survival time or rate, etc. Treatment and prevention can be complete or partial. The effect of treatment can be compared to an individual or pool of individuals not receiving the treatment, or to the same patient prior to treatment or at a different time during treatment. In some aspects, the severity of disease is reduced by at least 10%, as compared, e.g., to the individual before administration or to a control individual not undergoing treatment. In some aspects, the severity of disease is reduced by at least 25%, 50%, 75%, 80%, or 90%, or in some cases, no longer detectable using standard diagnostic techniques. "Treating" and "Treatment" can also mean prolonging survival as compared to expected survival if not receiving treatment. "Treating" and "treatment" as used herein also include prophylactic treatment.

Compositions or methods "comprising" or "including" one or more recited elements may include other elements not specifically recited (e.g., open-ended terms meaning including but not limited to). For example, a composition that "comprises" or "includes" an antibody may contain the antibody alone or in combination with other ingredients. In contrast, the phrase "consisting of" is closed, indicating that such embodiments do not include additional elements. The term "consisting essentially of" refers to the inclusion of recited elements and other elements that do not materially affect the basic and novel characteristics of a claimed combination (e.g., partially closed term). It is understood that aspects and embodiments described herein as "comprising" include "consisting of" and "consisting essentially of" embodiments.

As used herein, the following meanings apply unless otherwise specified. The word "may" is used in a permissive sense (i.e., meaning having the potential to), rather than the mandatory sense (i.e., meaning must). The singular forms "a," "an," and "the" include plural referents. Thus, for example, reference to "an element" includes a combination of two or more elements, notwithstanding use of other terms and phrases for one or more elements, such as "one or more." The phrase "at least one" includes "one", "one or more", "one or a plurality" and "a plurality". The term "or" is, unless indicated otherwise, non-exclusive, i.e., encompassing both "and" and "or." The term "any of" between a modifier and a sequence means that the modifier modifies each member of the sequence. So, for example, the phrase "at least any of 1, 2 or 3" means "at least 1, at least 2 or at least 3".

II. Chimeric Antigen Receptors

"Chimeric antigen receptors" or "CARs" are engineered molecules comprising an optional signal peptide, a target binding domain, an optional hinge region, a transmembrane domain, an intracellular signaling domain and an optional co-stimulatory domain. CARs are based on the structure of T cell receptors, which are expressed on T cells and which are involved in the cell-mediated immune response. The "target binding domain" is also referred to herein as an "antigen binding domain", and as such the term "target" encompasses an "antigen,"

So-called "first-generation" CARs had a targeting domain and a CD3ξ signal transduction domain. So-called "second generation" CARs further included a co-stimulatory domain, such as a CD28 or 4-1BB domain. So-called "third generation" CARs comprise multiple co-stimulatory domains. So-called "fourth generation" CARs, also referred to as "TRUCKS" are engineered to release a transgenic cytokine upon CAR signaling.

Chimeric antigen receptors ("CARs") include the following elements: (1) an optional signal peptide, (2) a target binding domain, (3) an optional hinge region; (4) a transmembrane region; (5) an intracellular domain comprising a signal transduction domain. Optionally, the CAR can include any of: a CD3ζ signal transduction domain, an Fc receptor signal transduction domain, a co-stimulatory (signal transduction) domain. That is, these optional elements can be included in addition to or instead of other optional elements. The target binding domain is heterologous to at least one of the other domains. That is, the target binding domain does not naturally occur on a T cell receptor, or is not in the same protein as at least one of the other domains.

The "target binding domain" provides binding specificity to the CAR. The "signal peptide" guides the polypeptide through the cell membrane. The target binding domain can bind to a domain of an antibody that binds to the target antigen for a so-called "Universal CAR". The "hinge region" is a flexible connector region, e.g., a natural or synthetic polypeptide, or any other type of molecule, providing structural flexibility and spacing to flanking polypeptide regions. The "transmembrane domain" is a membrane-spanning protein domain, typically hydrophobic. The "signal transduction domain" or "signaling domain" transmits a signal through a signal transduction pathway into the cell upon binding. Such signaling activates an activity of the cell. "Co-stimulatory domains" are accessory signaling domains that further transmit signals.

In some embodiments, the CAR comprises:
(i) an target-binding domain (also referred to herein as an antigen binding domain) reactive with a citrullinated protein or citrullinated fragment thereof, such as a VH-VL or VL-VH, wherein the two variable domains are separated by a flexible linker of from 15-25 amino acids in length;
(ii) a hinge domain;
(iii) a co-stimulatory domain; and
(iv) an intracellular signaling domain (also referred to herein as an activation domain). That is, in some embodiments the CAR comprises an antigen-binding domain fused to a CAR platform comprising a hinge domain, a transmembrane domain, and an intracellular domain comprising a costimulatory domain and an activation domain. The CAR may further include a signal peptide (also referred to herein as a leader sequence) to direct expression of the CAR to the surface of a cell, such as a Treg.

In some embodiments, the CAR comprises an antigen-binding domain fused in frame to a CAR platform comprising the amino acid sequences of SEQ ID NO:15, SEQ ID:17, SEQ ID NO:28, and SEQ ID:19. In other embodiments, the CAR comprises an antigen-binding domain fused in frame to a CAR platform comprising the amino acid sequences of SEQ ID NO:30, SEQ SEQ ID NO:28, and SEQ ID:19. In some embodiments, the CAR comprises an antigen-binding domain fused in frame to a CAR platform comprising the amino acid sequences of SEQ ID NO:30, SEQ ID:16, SEQ ID NO:29, and SEQ ID:19. In other embodiments, the CAR comprises an antigen-binding domain fused in frame to a CAR platform comprising the amino acid sequences of SEQ ID NO:30, SEQ ID:16, SEQ ID NO:29, and SEQ ID:19.

A. Signal Peptide

A signal peptide can be any peptide having the function of allowing a polypeptide to traverse a cell membrane. The signal peptide can be derived from CD4, CD8, CD28, TLR or immunoglobulin family of receptors.

For example, the signal peptide can comprise the sequence:

```
                                              (SEQ ID NO: 18)
MLLLVTSLLLCELPHPAFLLIP;
or
                                              (SEQ ID NO: 23)
MALPVTALLLPLALLLHAAR.
```

B. Target Binding Domain

1. Structure

The target binding domain can include any polypeptide comprising a target binding function, e.g., an antibody as defined herein. In one embodiment, the target binding domain can comprise an antibody form retaining antigen binding activity as defined herein. In one embodiment, the target binding domain can comprise a single chain antibody (scFV). The scFv can be connected to the transmembrane domain via a hinge domain whose length, flexibility and origin provides variability in the CAR's design, and can, along with the transmembrane domain, contribute to the interaction with antigen, building of the immunologic synapse and impact the CAR's association with additional proteins needed to impart a robust activation signal.

2. Targets/Antigens

Chimeric antigen receptors disclosed herein comprise a target binding domain (also referred to herein as an antigen-binding domain) that binds to citrullinated antigens, e.g., those found in the synovium of subjects with rheumatoid arthritis. In particular, the target binding domain can bind to one or more of (i) citrullinated vimentin, (ii) citrullinated filaggrin, (iii) citrullinated fibrinogen and (iv) citrullinated peptides thereof. In some embodiments, the target binding domain can bind to a citrullinated peptide fragment of (i)-(iii), wherein the peptide fragment is at least of 10 amino acids in length, e.g. of at least 12 amino acids, at least 14 amino acids or at least 16 amino acids in length. In some embodiments, the target binding domain further binds to tenascin C. In some embodiments, the target binding domain can bind to two or more of (i) citrullinated vimentin, (ii) citrullinated filaggrin, (iii) citrullinated fibrinogen, and (iv) tenascin C, or citrullinated peptide fragments thereof.

In some embodiments, the target domain is one or more citrullinated peptides selected from the following sequences:

```
                                              (SEQ ID NO: 24)
         ST(Cit)SVSSSSY(Cit)(Cit)MFGG;

(SEQ ID NO: 25)
         VYAT(Cit)SSAV(Cit)L(Cit)SSV;

(SEQ ID NO: 26)
         (Cit)PAPPPISGGGY(Cit)A(Cit);

(SEQ ID NO: 27)
         SHQEST(Cit)GRSRGRSGRSGS.
```

In some embodiments, the antigen binding domain binds to one or more citrullinated peptides, but does not bind to non-citrullinated counterparts. In some embodiments, the antigen binding domain binds to a citrullinated vimentin peptide set forth as SEQ ID NO:24, but not STRSVSSSSYRRMFGG (SEQ ID NO:45). In some embodiments, the antigen binding domain binds to a citrullinated vimentin peptide set forth as SEQ ID NO:25, but not VYATRSSAVRLRSSV (SEQ ID NO:46). In some embodiments, the antigen binding domain binds to a citrullinated fibrinogen peptide set forth as SEQ ID NO:26, but not RPAPPPISGGGYRAR (SEQ ID NO:47). In some embodiments, the antigen binding domain binds to a citrullinated filaggrin peptide set forth as SEQ ID NO:27, but not SHQESTRGRSRGRSGRSGS (SEQ ID NO:48).

The target binding domain can comprise sequences from an antibody VH and VL domain. In some embodiments, the target binding domain can comprise sequences from heavy chain only antibody or antibody fragment having only two VH domains. This includes particular CDR sets from VH and VL domains. In some embodiments the target binding domain comprises the CDRs from the VH domains of SEQ ID NO:1 or SEQ ID NO:2. In some embodiments the target binding domain comprises the CDRs from the VL domains of SEQ ID NO:3 or SEQ ID NO:4. In some embodiments the target binding domain comprises the CDRs from VH and VL domains of SEQ ID NO:1 and SEQ ID NO:3, respectively. In some embodiments the target binding domain comprises the CDRs from VH and VL domains of SEQ ID NO:1 and SEQ ID NO:4, respectively. In some embodiments the target binding domain comprises the CDRs from VH and VL domains of SEQ ID NO:2 and SEQ ID NO:3, respectively. In some embodiments the target binding domain comprises the CDRs from VH and VL domains of SEQ ID NO:2 and SEQ ID NO:4, respectively.

In some embodiments the target binding domain comprises the complementarity-determining regions (CDRs) from VH and VL domains of SEQ ID NO:1 (SBT01 VH (M)) and SEQ ID NO:4 (SBT01 VL (G)). In some embodiments, the VH domain of the target-binding domain comprises a VH-CDR1 comprising the amino acid sequence of SEQ ID NO:32, a VH-CDR2 comprising the amino acid sequence of SEQ ID NO:34, and a VH-CDR3 comprising the amino acid sequence of SEQ ID NO:36, and the VL domain of the target-binding domain comprises a VL-CDR1 comprising the amino acid sequence of SEQ ID NO:39, a VL-CDR2 comprising the amino acid sequence of SEQ ID NO:41, and a VL-CDR3 comprising the amino acid sequence of SEQ ID NO:43.

aforementioned sequences, provided target binding domain binds to a citrullinated antigen as described herein.

The target binding region can comprise VL sequences selected from:

(1) SBT01 VL (M)
(SEQ ID NO: 3)
SYVLTQPPSVSLAPGETATITCGGDDIENQNVNWYQQKSGQAPMLLIFF
DTRRPSGIPERFSGSRSEDTANLTITRVEAGDDADYFCQVYDRKTDHQV
FGPGTTVTVL;

(2) SBT01 VL (G)
(SEQ ID NO: 4)
SYVLTQPPSVSVAPGKTARITCGGNNIGSKSVHWYQQKPGQAPVLVIYY
DSDRPSGIPERFSGSNSGNTATLTISRVEAGDEADYYCQVWDSSSDHQV
FGTGTKVTVL;

| Region | SEQ ID | Sequence Fragment | Residues | Length |
|---|---|---|---|---|
| HFR1 | NO: 31 | HLHLQESGPGLVKPSETLSLTCTVSGGSIN | 1-30 | 30 |
| CDR-H1 | NO: 32 | DTTYYWG | 31-37 | 7 |
| HFR2 | NO: 33 | WIRQPPGKGLEWIG | 38-51 | 14 |
| CDR-H2 | NO: 34 | SIYYRGNTHYNSSLRS | 52-67 | 16 |
| HFR3 | NO: 35 | RVTMSVDTSKNRFSLVKVTSVTAADTAVYYCAR | 68-99 | 32 |
| CDR-H3 | NO: 36 | LDPFDY | 100-105 | 6 |
| HRF4 | NO: 37 | WGRGTLVTVSS | 106-116 | 11 |

| Region | SEQ ID | Sequence Fragment | Residues | Length |
|---|---|---|---|---|
| LFR1 | NO: 38 | SYVLTQPPSVSVAPGKTARITC | 1-22 | 22 |
| CDR-L1 | NO: 39 | GGNNIGSKSVH | 23-33 | 11 |
| LFR2 | NO: 40 | WYQQKPGQAPVLVIY | 34-48 | 15 |
| CDR-L2 | NO: 41 | YDSDRPS | 49-55 | 7 |
| LFR3 | NO: 42 | GIPERFSGSNSGNTATLTISRVEAGDEADYYC | 56-87 | 32 |
| CDR-L3 | NO: 43 | QVWDSSSDHQV | 88-98 | 11 |
| LFR4 | NO: 44 | FGTGTKVTV | 99-108 | 11 |

In certain embodiments, the target binding domain comprises VH sequences selected from:

(1) SBT01 VH (M)
(SEQ ID NO: 1)
HLHLQESGPGLVKPSETLSLTCTVSGGSINDTTYYWGWIRQPPGKGLEW
IGSIYYRGNTHYNSSLRSRVTMSVDTSKNRFSLKVTSVTAADTAVYYCA
RLDPFDYWGRGTLVTVSS;

(2) SBT01 VH (G)
(SEQ ID NO: 2)
QLQLQESGPGLVKPSETLSLTCTVSGGSISSSSYYWGWIRQPPGKGLEW
IGSIYYSGSTYYNPSLKSRVTISVDTSKNQFSLKLSSVTAADTAVYYCA
RLDPFDYWGRGTLVTVSS;

or
a sequence having at least any of 80%, 85%, 90%, 95%, 97%, 98%, 99% or 99.5% sequence identify with the aforementioned sequences, provided target binding domain binds to a citrullinated antigen as described herein.

or
a sequence having at least any of 80%, 85%, 90%, 95%, 97%, 98%, 99% or 99.5% sequence identify with the aforementioned sequences, provided target binding domain binds to a citrullinated antigen as described herein.

In another embodiment, the antigen binding region comprises an scFV comprising one or more VH domains comprising an amino acid sequence of VH domains of SEQ ID NO:1 or SEQ ID NO:2. In some embodiments, the antigen binding region comprises an scFV comprising an amino acid sequence having at least any of 80%, 85%, 90%, 95%, 97%, 98%, 99% or 99.5% of SEQ ID NO:1 or SEQ ID NO:2, provided the scFV domain binds to a citrullinated antigen as described herein.

In some embodiments, the scFV comprises the VL domains of SEQ ID NO:3 or SEQ ID NO:4. In some embodiments, the antigen binding region comprises an scFV comprising an amino acid sequence having at least any of 80%, 85%, 90%, 95%, 97%, 98%, 99% or 99.5% of SEQ ID NO: 3 or SEQ ID NO:4, provided the scFV domain binds to a citrullinated antigen as described herein.

In some embodiments, the scFV domain comprises the VH and VL domains of SEQ ID NO:1 and SEQ ID NO:3, respectively. In some embodiments, the antigen binding region comprises an scFV comprising an amino acid sequence having at least any of 80%, 85%, 90%, 95%, 97%, 98%, 99% or 99.5% of SEQ ID NO: 1 or SEQ ID NO:3, provided the scFV domain binds to a citrullinated antigen as described herein. In some embodiments, a linker selected from SEQ ID NO: 20, SEQ ID NO: 21 or SEQ ID NO: 22 is placed between the VH and VL domains.

In some embodiments, the scFV domain comprises the VH and VL domains of SEQ ID NO:1 and SEQ ID NO:4, respectively. In some embodiments, the antigen binding region comprises an scFV comprising an amino acid sequence having at least any of 80%, 85%, 90%, 95%, 97%, 98%, 99% or 99.5% of SEQ ID NO: 1 and SEQ ID NO:4, provided the scFV domain binds to a citrullinated antigen as described herein. In some embodiments, a linker selected from SEQ ID NO: 20, SEQ ID NO: 21 or SEQ ID NO: 22 is placed between the VH and VL domains.

In some embodiments, the scFV domain comprises the VH and VL domains of SEQ ID NO: 2 and SEQ ID NO:3, respectively. In some embodiments, the antigen binding region comprises an scFV comprising an amino acid sequence having at least any of 80%, 85%, 90%, 95%, 97%, 98%, 99% or 99.5% of SEQ ID NO: 2 and SEQ ID NO: 3, provided the scFV domain binds to a citrullinated antigen as described herein. In some embodiments, a linker selected from SEQ ID NO: 20, SEQ ID NO: 21 or SEQ ID NO: 22 is placed between the VH and VL domains.

In some embodiments, the scFV domain comprises the VH and VL domains of SEQ ID NO:2 and SEQ ID NO:4, respectively. In some embodiments, the antigen binding region comprises an scFV comprising an amino acid sequence having at least any of 80%, 85%, 90%, 95%, 97%, 98%, 99% or 99.5% of SEQ ID NO: 2 and SEQ ID NO: 4, provided the scFV domain binds to a citrullinated antigen as described herein. In some embodiments, a linker selected from SEQ ID NO: 20, SEQ ID NO: 21 or SEQ ID NO: 22 is placed between the VH and VL domains.

In another embodiment, the antigen binding region comprises an scFV comprising an amino acid sequence selected from:

SBT01G-VHVL-GGGSx3 Linker-PSB_0149
(SEQ ID NO: 5)
HLHLQESGPGLVKPSETLSLTCTVSGGSINDTTYYWGWIRQPPGKGLEW

IGSIYYRGNTHYNSSLRSRVTMSVDTSKNRFSLKVTSVTAADTAVYYCA

RLDPFDYWGRGTLVTVSSGGGGSGGGGSGGGGSSYVLTOPPSVSVAPGK

TARITCGGNNIGSKSVHWYQQKPGQAPVLVIYYDSDRPSGIPERFSGSN

SGNTATLTISRVEAGDEADYYCQVWDSSSDHQVFGTGTKVTVLR (GGGSx3 linker underlined);

SBT01G-VHVL-Whitlow 218 Linker-pSB_0158
(SEQ ID NO: 6)
HLHLQESGPGLVKPSETLSLTCTVSGGSINDTTYYWGWIRQPPGKGLEW

IGSIYYRGNTHYNSSLRSRVTMSVDTSKNRFSLKVTSVTAADTAVYYCA

RLDPFDYWGRGTLVTVSSGSTSGSGKPGSGEGSTKGSYVLTOPPSVSVA

PGKTARITCGGNNIGSKSVHWYQQKPGQAPVLVIYYDSDRPSGIPERFS

GSNSGNTATLTISRVEAGDEADYYCQVWDSSSDHQVFGTGTKVTVLR (Whitlow 218 Linker underlined);

SBT01G-VHVL-AB pur Linker-pSB_0159
(SEQ ID NO: 7)
HLHLQESGPGLVKPSETLSLTCTVSGGSINDTTYYWGWIRQPPGKGLEW

IGSIYYRGNTHYNSSLRSRVTMSVDTSKNRFSLKVTSVTAADTAVYYCA

RLDPFDYWGRGTLVTVSSASSGGSTSGSGKPGSGEGSSGSARSYVLTQP

PSVSVAPGKTARITCGGNNSGSKSVHWYQQKPGQAPVLVIYYDSDRPSG

IPERFSGSNSGNTATLTISRVEAGDEADYYCQVWDSSSDHQVFGTGTKV

TVLR (AB pur Linker underlined):

or
a sequence having at least any of 80%, 85%, 90%, 95%, 97%, 98%, 99% or 99.5% sequence identify with the aforementioned sequences, provided target binding domain binds to a citrullinated antigen as described herein.

For example, the linker can comprise the sequence:

(SEQ ID NO: 20)
GGGGSGGGGSGGGGS GGGSx3 Linker;
or (SEQ ID NO: 21)
GSTSGSGKPGSGEGSTKG Whitlow 218 Linker;
or (SEQ ID NO: 22)
ASSGGSTSGSGKPGSGEGSSGSAR AB pur Linker.

Optionally, any of the foregoing sequences can include the CDR sets from the VH and VL domains described above.

C. Hinge Region

In some embodiments, the hinge region of the disclosed CARs can be selected from the CD8, CD4, or CD28 extracellular domain, the Fc region of an IgG1 antibody, or the extracellular domain of any of the TLR receptors as is known to one of skill in the art and can be found in the GenBank database.

For example, the hinge region can comprise the sequence:

(SEQ ID NO: 30)
IEVMYPPPYLDNEKSNGTIIHVKGKHLCPSPLFPGPSKP (CD28);
or (SEQ ID NO: 15)
TTTPAPRPPTPAPTIASQPLSLRPEACRPAAGGAVHTRGLDFACDIYIW
APLAGTCGVLLLSLVITLYC (CD8);

or
a sequence having at least any of 80%, 85%, 90%, 95%, 97%, 98%, 99% or 99.5% sequence identify with the aforementioned hinge region sequences.

D. Transmembrane Domain

The transmembrane domain can comprise a transmembrane domain of an immunoglobulin family receptor, such as CD8. The intracellular domain can be selected from any membrane-spanning molecule on a T cell. For example, the transmembrane (TM) domain of the disclosed CAR can comprise the TM domain of CD2, CD3, CD16, CD32, CD64, CD28, CD247, 4-1BBL, CD4, or CD8.

For example, the transmembrane domain can comprise the sequence:

```
                                            (SEQ ID NO: 16)
FWVLVVVGGVLACYSLLVTVAFIIFWV;
or
                                            (SEQ ID NO: 17)
IYIWAPLAGTCGVLLLSLVITLYC;
``` or
- a sequence having at least any of 80%, 85%, 90%, 95%, 97%, 98%, 99% or 99.5% sequence identify with the aforementioned hinge region sequences.

E. Signal Transduction Domain

1. CD3ζ Signal Transduction Domain

In some embodiments, the signal transduction domain comprises a CD3ζ signaling domain. The CD3ζ signaling domain of the disclosed CAR molecule can comprise a CD3ζ amino acid sequence, e.g., a signal transduction domain of CD3 zeta.

For example, the CD3ζ signal transduction domain can comprise the sequence:

```
                                            (SEQ ID NO: 19)
RVKFSRSADAPAYQQGQNQLYNELNLGRREEYDVLDKRRGRDPEMGGKP
RRKNPQEGLYNELQKDKMAEAYSEIGMKGERRRGKGHDGLYQGLSTATK
DTYDALHMQALPPR;
``` or
- a sequence having at least any of 80%, 85%, 90%, 95%, 97%, 98%, 99% or 99.5% sequence identify with the aforementioned CD3 zeta signal transduction domain sequence.

For example, the CD3 zeta signal transduction domain can include amino acids 21-163, 31-142, 68-89 and/or 138-158 of the sequence shown in SEQ ID NO:19, or functional variants thereof (e.g., with 1, 2, 3, 4, 5, 6, 7, 8, 9, 10, or 10-20 amino acid substitutions, deletions, or additions).

2. Fc Receptor Signal Transduction Domain

In some embodiments, the signal transduction domain comprises an Fc signaling domain. The Fc signaling domain can be any one of the Fc-alpha, Fc-gamma, Fc-epsilon, Fc-mu, and Fc-delta receptors. For example, the Fc receptor signaling domain can comprise amino acids involved in interaction with Src (e.g., Fgr, Fyn, Hck, Lyn, Yes, and Src) and ZAP-70 family kinases, e.g., one or more ITAM domains (see, e.g., Sanchez-Mejorada et al. (1998) *J. Leukocyte Biol.* 63:531; Garcia-Garcia et al. (2002) *J. Leukocyte Biol.* 72:1092). In some embodiments, the Fc receptor signal transduction domain includes at least one ITAM domain, e.g., from any one of the Fc-alpha, Fc-gamma, Fc-epsilon, Fc-mu, and Fc-delta receptors, or substantially identical thereto.

Sequences also can be found as follows:

| Molecule | GenBank No. |
| --- | --- |
| CD3ζ | NP_000725.1 |
| Fc gamma receptor family (CD16) | NP_000560.5 |
|  | NP_001231682.1 |
| Fc gamma receptor family (CD32) | AAH20823.1 |
|  | AAH19931.1 |
|  | AAI48274.1 |
|  | AAI37398.1 |
| Fc gamma receptor family (CD64) | AAI60240.1 |
|  | AAH32634.1 |
|  | AAI56865.1 |

F. Co-Stimulatory Domain

The CARs of this disclosure can include one or more co-stimulatory domains in addition to a signal transduction domain of CD3ζ or an Fc receptor. Co-stimulatory domains can be derived from, for example, CD28, 4-1BB, CD2, CD27, CD30, OX40, CD40, PD-1, PD-L1, PD-L2, ICOS, LFA-1, CD7, LIGHT, NKG2C, B7-H3, CD83L, B7-1 (CD80), B7-2 (CD86), B7-H3, B7-H4 and others. The CAR constructs can contain two or more co-stimulatory signaling domains (e.g., CD28 and 4-1BB).

The co-stimulatory domain or domains can be positioned between the signal transduction domain and the transmembrane region.

In certain embodiments, a CD28 co-stimulatory domain can comprise the sequence:

```
                                            (SEQ ID NO: 29)
RSKRSRLLHSDYMNMTPRRPGPTRKHYQPYAPPRDFAAYRS;
``` or
- a sequence having at least any of 80%, 85%, 90%, 95%, 97%, 98%, 99% or 99.5% sequence identify with the aforementioned sequence.

In certain embodiments, a 41BB co-stimulatory domain can comprise the sequence:

```
                                            (SEQ ID NO: 28)
KRGRKKLLYIFKQPFMRPVQTTQEEDGCSCRFPEEEEGGCEL;
``` or
- a sequence having at least any of 80%, 85%, 90%, 95%, 97%, 98%, 99% or 99.5% sequence identify with the aforementioned sequence.

III. Nucleic Acids

A. Nucleic Acids Encoding CARs

Disclosed herein are nucleic acid molecules (polynucleotides) comprising a nucleotide sequence that encodes a CAR of this disclosure. The nucleic acid of the disclosed CAR can be in the form of DNA or in the form of RNA. DNA includes cDNA, genomic DNA, and synthetic DNA; and can be double-stranded or single-stranded, and if single stranded can be the coding strand or non-coding (anti-sense) strand. RNA includes mRNA, siRNA, sRNA, ssRNA and so on.

For example, nucleic acids can comprise nucleotide sequences that encode the polypeptides of any of SEQ ID NO:1, SEQ ID NO:2, SEQ ID NO:3, SEQ ID NO:4. In certain embodiments, the nucleotide sequences encoding VH domains comprise:

(1) SBT01 VH (M)
(SEQ ID NO: 8)
CACCTGCACTTGCAGGAGTCGGGCCCAGGACTTGTGAAGCCTTCGGAGA

CCCTGTCCCTCACCTGCACTGTCTCTGGTGGCTCCATCAACGATACCAC

TTACTACTGGGGCTGGATTCGCCAGCCCCCGGGAAGGGACTGGAGTGG

ATTGGGAGTATCTATTACCGGGGAACACCCACTACAATTCGTCCCTGA

GGAGTCGCGTCACCATGTCTGTCGACACTTCCAAGAACCGATTCTCCCT

GAAGGTCACTTCTGTGACTGCCGCAGACACGGCTGTCTATTACTGTGCG

AGACTCGACCCATTTGACTACTGGGGCCGTGGCACCCTGGTCACTGTCT

CGAGC, (2) SBT01 VH (G)
(SEQ ID NO: 9)
CAGCTGCAGCTGCAGGAGTCGGGCCCAGGACTGGTGAAGCCTTCGGAGA

CCCTGTCCCTCACCTGCACTGTCTCTGGTGGCTCCATCAGCAGTAGTAG

TTACTACTGGGGCTGGATCCGCCAGCCCCCAGGGAAGGGGCTGGAGTGG

ATTGGGAGTATCTATTATAGTGGGAGCACCTACTACAACCCGTCCCTCA

AGAGTCGAGTCACCATATCCGTAGACACGTCCAAGAACCAGTTCTCCCT

GAAGCTGAGCTCTGTGACCGCCGCAGACACGGCTGTGTATTACTGTGCG

AGACTCGACCCATTTGACTACTGGGGCCGTGGCACCCTGGTCACTGTCT

CGAGC;

or
a sequence having at least any of 80%, 85%, 90%, 95%, 97%, 98%, 99% or 99.5% sequence identify with the aforementioned sequences.

In certain embodiments, the nucleotide sequences encoding VL domains comprise:

(1) SBT01 VL (M)
(SEQ ID NO: 10)
TCCTATGTCCTGACTCAGCCACCCTCAGTGTCGCTGGCCCCGGGAGAGA

CGGCCACAATTACTTGTGGTGGAGACGACATTGAAAATCAAAATGTCAA

CTGGTATCAGCAGAAGTCAGGTCAGGCCCCTATGCTGCTCATCTTCTTT

GATACCAGACGGCCCTCAGGGATCCCGGAGCGATTCTCTGGCTCCAGGT

CTGAGGACACGGCCAACCTGACCATCACCAGGGTCGAGGCCGGGGATGA

CGCCGACTATTTCTGTCAGGTGTATGATAGGAAGACTGATCACCAAGTC

TTCGGACCTGGGACCACGGTCACCGTCCTA;

(2) SBT01 VL (G)
(SEQ ID NO: 11)
TCCTATGTGCTGACTCAGCCACCCTCAGTGTCAGTGGCCCCAGGAAAGA

CGGCCAGGATTACCTGTGGGGGAAACAACATTGGAAGTAAAAGTGTGCA

CTGGTACCAGCAGAAGCCAGGCCAGGCCCCTGTGCTGGTCATCTATTAT

GATAGCGACCGGCCCTCAGGGATCCCTGAGCGATTCTCTGGCTCCAACT

CTGGGAACACGGCCACCCTGACCATCAGCAGGGTCGAAGCCGGGGATGA

GGCCGACTATTACTGTCAGGTGTGGGACAGTAGTAGTGATCACCAAGTC

TTCGGAACTGGGACCAAGGTCACCGTCCTA;

or
a sequence having at least any of 80%, 85%, 90%, 95%, 97%, 98%, 99% or 99.5% sequence identify with the aforementioned sequences.

In another embodiment, the nucleic acid molecule encoding VH domains comprise SEQ ID NO: 8 or SEQ ID NO:9. In some embodiments, the nucleic acid molecule encoding VH domains comprise a nucleic sequence having at least any of 80%, 85%, 90%, 95%, 97%, 98%, 99% or 99.5% of SEQ ID NO:8 or SEQ ID NO:9, provided the scFV domain binds to a citrullinated antigen as described herein.

In some embodiments, the nucleic acid molecule encoding VL domains comprise SEQ ID NO: 10 or SEQ ID NO: 11. In some embodiments, the nucleic acid molecule encoding VL domains comprise a nucleic sequence having at least any 80%, 85%, 90%, 95%, 97%, 98%, 99% or 99.5% of SEQ ID NO: 10 or SEQ ID NO: 11, provided the scFV domain binds to a citrullinated antigen as described herein.

In some embodiments, the nucleic acid molecule encoding an scFV domain comprise SEQ ID NO:8 and SEQ ID NO:10. In some embodiments, the nucleic acid molecule encoding the scFV comprises an amino acid sequence having at least any of 80%, 85%, 90%, 95%, 97%, 98%, 99% or 99.5% of SEQ ID NO: 8 or SEQ ID NO:10, provided the scFV domain binds to a citrullinated antigen as described herein.

In some embodiments, the nucleic acid molecule encoding an scFV domain comprise SEQ ID NO: 8 and SEQ ID NO: 11. In some embodiments, the nucleic acid molecule encoding the scFV comprises an amino acid sequence having at least any of 80%, 85%, 90%, 95%, 97%, 98%, 99% or 99.5% of SEQ ID NO: 8 or SEQ ID NO:11, provided the scFV domain binds to a citrullinated antigen as described herein.

In some embodiments, the nucleic acid molecule encoding an scFV domain comprise SEQ ID NO: 9 and SEQ ID NO:10. In some embodiments, the nucleic acid molecule encoding the scFV comprises an amino acid sequence having at least any of 80%, 85%, 90%, 95%, 97%, 98%, 99% or 99.5% of SEQ ID NO: 9 or SEQ ID NO: 10, provided the scFV domain binds to a citrullinated antigen as described herein.

In some embodiments, the nucleic acid molecule encoding an scFV domain comprise SEQ ID NO: 9 and SEQ ID NO:11. In some embodiments, the nucleic acid molecule encoding the scFV comprises an amino acid sequence having at least any of 80%, 85%, 90%, 95%, 97%, 98%, 99% or 99.5% of SEQ ID NO: 9 or SEQ ID NO: 11, provided the scFV domain binds to a citrullinated antigen as described herein.

In another embodiment, the nucleic acid molecule encodes an scFv molecule and has a nucleotide sequence:

SBT01G-VHVL GGGSx3 Linker-pSB_0149
(SEQ ID NO: 12)
CACCTGCACTTGCAGGAGTCGGGCCCAGGACTTGTGAAGCCTTCGGAGA

CCCTGTCCCTCACCTGCACTGTCTCTGGTGGCTCCATCAACGATACCAC

TTACTACTGGGGCTGGATTCGCCAGCCCCCGGGAAGGGACTGGAGTGG

ATTGGGAGTATCTATTACCGGGGAACACCCACTACAATTCGTCCCTGA

GGAGTCGCGTCACCATGTCTGTCGACACTTCCAAGAACCGATTCTCCCT

GAAGGTCACTTCTGTGACTGCCGCAGACACGGCTGTCTATTACTGTGCG

AGACTCGACCCATTTGACTACTGGGGCCGTGGCACCCTGGTCACTGTCT

CGAGCGGTGGCGGTGGCTCGGGCGGTGGTGGGTCGGGTGGCGGCGGATC

TTCCTATGTGCTGACTCAGCCACCCTCAGTGTCAGTGGCCCCAGGAAAG

```
ACGGCCAGGATTACCTGTGGGGGAAACAACATTGGAAGTAAAAGTGTGC

ACTGGTACCAGCAGAAGCCAGGCCAGGCCCCTGTGCTGGTCATCTATTA

TGATAGCGACCGGCCCTCAGGGATCCCTGAGCATTCTCTGGCTCCAACT

CTGGGAACACGGCCACCCTGACCATCAGCAGGGTCGAAGCCGGGGATGA

GGCCGACTATTACTGTCAGGTGTGGGACAGTAGTAGTGATCACCAAGTC

TTCGGAACTGGGACCAAGGTCACCGTCCTACGC (GGGSx3 linker underlined);
``` or
a sequence having at least any of 80%, 85%, 90%, 95%, 97%, 98%, 99% or 99.5% sequence identify with the aforementioned sequence.

In another embodiment, the nucleic acid molecule encodes an scFv molecule and has a nucleotide sequence:

```
SBT01G-VHVL-Whitlow 218 Linker-pSB_0158
                                    (SEQ ID NO: 13)
CACCTGCACTTGCAGGAGTCGGGCCCAGGACTTGTGAAGCCTTCGGAGA

CCCTGTCCCTCACCTGCACTGTCTCTGGTGGCTCCATCAACGATACCAC

TTACTACTGGGGCTGGATTCGCCAGCCCCCGGGAAGGGACTGGAGTGG

ATTGGGAGTATCTATTACCGGGGAACACCCACTACAATTCGTCCCTGA

GGAGTCGCGTCACCATGTCTGTCGACACTTCCAAGAACCGATTCTCCCT

GAAGGTCACTTCTGTGACTGCCGCAGACACGGCTGTCTATTACTGTGCG

AGACTCGACCCATTTGACTACTGGGGCCGTGGCACCCTGGTCACTGTCT

CGAGCGGAAGCACGAGTGGTTCAGGCAAACCGGGTTCCGGTGAAGGTTC

AACAAAAGGTTCCTATGTGCTGACTCAGCCACCCTCAGTGTCAGTGGCC

CCAGGAAAGACGGCCAGGATTACCTGTGGGGGAAACAACATTGGAAGTA

AAAGTGTGCACTGGTACCAGCAGAAGCCAGGCCAGGCCCCTGTGCTGGT

CATCTATTATGATAGCGACCGGCCCTCAGGGATCCCTGAGCGATTCTCT

GGCTCCAACTCTGGGAACACGGCCACCCTGACCATCAGCAGGGTCGAAG

CCGGGGATGAGGCCGACTATTACTGTCAGGTGTGGGACAGTAGTAGTGA

TCACCAAGTCTTCGGAACTGGGACCAAGGTCACCGTCCTACGC (Whitlow 218 Linker underlined);
``` or
a sequence having at least any of 80%, 85%, 90%, 95%, 97%, 98%, 99% or 99.5% sequence identify with the aforementioned sequence.

In another embodiment, the nucleic acid molecule encodes an scFv molecule and has a nucleotide sequence:

```
SBT01G-VHVL-AB pur Linker-pSB_0159
                                    (SEQ ID NO: 14)
CACCTGCACTTGCAGGAGTCGGGCCCAGGACTTGTGAAGCCTTCGGAGA

CCCTGTCCCTCACCTGCACTGTCTCTGGTGGCTCCATCAACGATACCAC

TTACTACTGGGGCTGGATTCGCCAGCCCCCGGGAAGGGACTGGAGTGG

ATTGGGAGTATCTATTACCGGGGAACACCCACTACAATTCGTCCCTGA

GGAGTCGCGTCACCATGTCTGTCGACACTTCCAAGAACCGATTCTCCCT

GAAGGTCACTTCTGTGACTGCCGCAGACACGGCTGTCTATTACTGTGCG

AGACTCGACCCATTTGACTACTGGGGCCGTGGCACCCTGGTCACTGTCT

CGAGCGCCTCTAGCGGGGGGAGCACATCAGGAAGCGGCAAGCCCGGTAG

CGGCGAAGGCTCCTCTGGCAGCGCCCGCTCCTATGTGCTGACTCAGCCA

CCCTCAGTGTCAGTGGCCCCAGGAAAGACGGCCAGGATTACCTGTGGGG

GAAACAACATTGGAAGTAAAAGTGTGCACTGGTACCAGCAGAAGCCAGG

CCAGGCCCCTGTGCTGGTCATCTATTATGATAGCGACCGGCCCTCAGGG

ATCCCTGAGCGATTCTCTGGCTCCAACTCTGGGAACACGGCCACCCTGA

CCATCAGCAGGGTCGAAGCCGGGGATGAGGCCGACTATTACTGTCAGGT

GTGGGACAGTAGTAGTGATCACCAAGTCTTCGGAACTGGGACCAAGGTC

ACCGTCCTACGC (AB pur Linker underlined);
``` or
a sequence having at least any of 80%, 85%, 90%, 95%, 97%, 98%, 99% or 99.5% sequence identify with the aforementioned sequences.

Optionally, these can include sequences encoding the CDR sets from the VH and VL domains described herein.

The polynucleotide variants can contain alterations in the coding regions, non-coding regions, or both. In some embodiments, the polynucleotide variants contain alterations that produce silent substitutions, additions, or deletions, but do not alter the properties or activities of the encoded CAR polypeptide. In some embodiments, the polynucleotide variants contain alterations that do not produce any changes in the amino acid sequence. In some embodiments, polynucleotide variants contain "silent" substitutions due to the degeneracy of the genetic code. Polynucleotide variants can be produced for a variety of reasons, for example, to optimize codon expression for a particular host.

In some embodiments, the polynucleotides as described herein are isolated.

Polynucleotides encoding CARs be isolated molecules, or can be included within a vector, such as a plasmid, a cosmid, an artificial chromosome or a virus. Such vectors can be used to transfect target cells.

B. Expression Constructs and Vectors

Polynucleotides encoding CARs of this disclosure can include regulatory elements operatively linked with a nucleotide sequence encoding the CAR. For example, a polynucleotide can include one or more transcription regulatory elements, such as promoters or enhancers, which, when the polynucleotide is present in a cell, cause the sequence encoding the CAR to be expressed within the cell.

Nucleic acids disclosed herein can be incorporated into vectors capable of transfecting cells. Such vectors include, without limitation, viral vectors plasmids and microvesicles, e.g., liposomes. Exemplary viral vectors adenoviral vectors Ad, AAV, lentivirus, and vesicular stomatitis virus (VSV) and retroviruses. Lentiviruses are a genus of the Retroviridae family and include HIV, SIV, and FIV. Lentiviruses can deliver a large quantities of genetic material into the DNA of the host cell. They are able to infect non-dividing cells.

IV. Cells

In some embodiments, the recombinant (host) cell having the nucleic acid molecule encoding the disclosed CAR wherein the nucleic acid molecule can further comprises an expression control sequence operatively linked with the nucleotide sequence encoding the CAR. The assembled CAR (by synthesis, site-directed mutagenesis or another method, as is known to one of skill in the art), the nucleic acid molecule encoding the disclosed CAR can be inserted into an expression vector and operatively linked to an expression control sequence appropriate for expression of the disclosed CAR in a desired host. Correct assembly can be confirmed by nucleotide sequencing, restriction mapping, and/or expression of the CAR polypeptide in a suitable host. As is well known in the art, in order to obtain high expression levels of a transfected gene in a host, the gene must be operatively linked to transcriptional and translational expression control sequences that are functional in the chosen expression host.

This disclosure also provides cells (e.g., recombinant cells) comprising nucleic acid molecules encoding CARs and/or expressing CARs.

The nucleic acid molecule encoding the disclosed CAR can be delivered to a host cell, including but not limited to a T cell, B cell, myeloid progenitor, macrophage, and so on, by a plasmid or a viral vector as is known to one of skill in the art. The resulting recombinant (host) cell can include but is not limited to a T-cell, a CD4 T-cell, a Treg cell, a CD8 alpha T-cell, CD8 beta T cell, T helper cell, granulocyte (neutrophils, basophils, eosinophils), megakaryocytes, monocyte, macrophage and a dendritic cell, a memory stem cell as well as cells expressing MHC class I or class II as is known to one of skill in the art. In some embodiments, the recombinant (host) cell having the nucleic acid molecule encoding the disclosed CAR can be a myeloid progenitor cell selected from the group consisting of a common myeloid progenitor, a granulocyte macrophage progenitor, a megakaryocyte erythrocyte progenitor, a granulocyte progenitor and a monocyte progenitor as is known to one of skill in the art. In some embodiments, the myeloid cell is an autologous or allogeneic cell.

In some embodiments, the cells expressing the CARs of this disclosure are Treg cells. "Regulatory T cells," or "$T_{reg}$ cells," are cells belonging to a specialized subpopulation of T cells that act to suppress immune response, thereby maintaining homeostasis and self-tolerance. $T_{reg}$s are able to inhibit T cell proliferation and cytokine production and play a critical role in preventing autoimmunity. $T_{reg}$s are characterized by expression of FoxP3. Surface markers for $T_{reg}$s include CD4, CD25high (high molecular density) and CD127low (low molecular density). Mouse and human Tregs express GITR/AITR, and CTLA-4. Human CD4+ FoxP3+ Treg cells can be divided into three sub-populations: (1) CD45RA+CD25+FoxP310w resting Treg cells, (2) CD45RO+CD25highFoxP3high activated Treg cells, and (3) proinflammatory cytokine-producing CD45RO+CD25+ FoxP3low nonsuppressive effector cells (Teffs).

The cells to be transformed with the nucleic acids disclosed herein can be cells taken from a subject into whom the recombinant cells are to be administered. In this way, issues of an allogeneic immune response can be mitigated.

Cells can be expanded ex vivo before administration to a subject.

Treg cells into which nucleic acids expressing the CARs of this disclosure have been incorporated can express these CARs and be used in the methods described herein to treat rheumatoid arthritis.

Also, the proteins produced by a transformed/recombinant host can be purified according to any suitable method. Such methods include chromatography (e.g., ion exchange, affinity, and sizing column chromatography), centrifugation, differential solubility, or by any other standard technique for protein purification. Affinity tags such as hexa-histidine, maltose binding domain, influenza coat sequence and glutathione-S-transferase can be attached to the protein to allow easy purification by passage over an appropriate affinity column. In some embodiments, proteins can also be physically characterized using such techniques as proteolysis, high performance liquid chromatography (HPLC), nuclear magnetic resonance and x-ray crystallography.

V. Compositions

Also disclosed are pharmaceutical compositions comprising a recombinant cell having a nucleic acid molecule encoding the disclosed CAR polypeptide and/or expressing the disclosed CAR polypeptide, and a pharmaceutically acceptable carrier, as well as methods of use in the treatment rheumatoid arthritis.

As used herein, the term "pharmaceutical composition" refers to a composition comprising a pharmaceutical compound (e.g., a drug or a recombinant Treg cell as described herein) and a pharmaceutically acceptable carrier.

As used herein, the term "pharmaceutically acceptable" refers to a carrier that is compatible with the other ingredients of a pharmaceutical composition and can be safely administered to a subject. The term is used synonymously with "physiologically acceptable" and "pharmacologically acceptable". Pharmaceutical compositions and techniques for their preparation and use are known to those of skill in the art in light of the present disclosure. For a detailed listing of suitable pharmacological compositions and techniques for their administration one may refer to texts such as Remington's Pharmaceutical Sciences, 17th ed. 1985; Brunton et al., "Goodman and Gilman's The Pharmacological Basis of Therapeutics," McGraw-Hill, 2005; University of the Sciences in Philadelphia (eds.), "Remington: The Science and Practice of Pharmacy," Lippincott Williams & Wilkins, 2005; and University of the Sciences in Philadelphia (eds.), "Remington; The Principles of Pharmacy Practice," Lippincott Williams & Wilkins, 2008.

Pharmaceutically acceptable carriers will generally be sterile, at least for human use. A pharmaceutical composition will generally comprise agents for buffering and preservation in storage, and can include buffers and carriers for appropriate delivery, depending on the route of administration. Examples of pharmaceutically acceptable carriers include, without limitation, normal (0.9%) saline, phosphate-buffered saline (PBS) Hank's balanced salt solution (HBSS) and multiple electrolyte solutions such as Plasma-Lyte ATM (Baxter).

Pharmaceutical compositions can be formulated for any route of administration, including mucosal (e.g., nasal, sublingual, vaginal, buccal, or rectal), parenteral (e.g., subcutaneous, intravenous, intramuscular, or intraarterial injection, either bolus or infusion), oral, or transdermal.

Injectable (e.g., intravenous) compositions can comprise a solution of the composition suspended in an acceptable carrier, such as an aqueous carrier. Any of a variety of aqueous carriers can be used, e.g., water, buffered water, 0.4% saline, 0.9% isotonic saline, 0.3% glycine, 5% dextrose, and the like, and may include glycoproteins for enhanced stability, such as albumin, lipoprotein, globulin, etc. Often, normal buffered saline (135-150 mM NaCl) will be used. The compositions can contain pharmaceutically acceptable auxiliary substances to approximate physiological conditions, such as pH adjusting and buffering agents, tonicity adjusting agents, wetting agents, e.g., sodium acetate, sodium lactate, sodium chloride, potassium chloride, calcium chloride, sorbitan monolaurate, triethanolamine oleate, etc. In some embodiments, the composition can be formulated in a kit for intravenous administration.

Formulations suitable for parenteral administration, such as, for example, by intraarticular (in the joints), intravenous, intramuscular, intratumoral, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. Injection solutions and suspensions can also be prepared from sterile powders, granules, and tablets. In the practice of the present invention, compositions can be administered, for example, by intravenous infusion, topically, intraperitoneally, intravesically, or intrathecally. The formulations of compositions can be presented in unit-dose or multi-dose sealed containers, such as ampoules and vials.

Cells can be cryopreserved. Cryopreservation can include formulating cells with a cryopreservation agent, such as DMSO. Commercially available media include, for example, CryoStor® and pZerve®, available from Millipore Sigma.

Compositions can be formulated as dosage forms for administration. The term "dosage form" refers to the particular format of the pharmaceutical, and depends on the route of administration. Examples of dosage forms include, but are not limited to: dispersions; suppositories; ointments; cataplasms (poultices); pastes; powders; dressings; creams; plasters; solutions; patches; aerosols (e.g., nasal sprays or inhalers); gels; liquid dosage forms suitable for oral or mucosal administration to a patient, including suspensions (e.g., aqueous or non-aqueous liquid suspensions, oil-in-water emulsions, or a water-in-oil liquid emulsions), solutions, and elixirs; liquid dosage forms suitable for parenteral administration to a patient; and sterile solids (e.g., crystalline or amorphous solids) that can be reconstituted to provide liquid dosage forms suitable for parenteral administration to a patient.

The terms "dose" and "dosage" are used interchangeably herein. A dose refers to the amount of active ingredient given to an individual at each administration. The dose will vary depending on a number of factors, including frequency of administration; size and tolerance of the individual; severity of the condition; risk of side effects; the route of administration; and the imaging modality of the detectable label (if present). One of skill in the art will recognize that the dose can be modified depending on the above factors or based on therapeutic progress.

The pharmaceutical preparation can be packaged or prepared in unit dosage form. In such form, the preparation is subdivided into unit doses containing appropriate quantities of the active component, e.g., according to the dose of the therapeutic agent or concentration of the composition. The unit dosage form can be a packaged preparation, the package containing discrete quantities of preparation. The composition can, if desired, also contain other compatible therapeutic agents.

In some embodiments, the compositions of the invention comprise a recombinant cell having a nucleic acid molecule encoding a CAR polypeptide comprising the complementarity-determining regions (CDRs) from the VH domains of SEQ ID NO:1 or SEQ ID NO:2. In some embodiments, the compositions of the invention comprise a recombinant cell having a nucleic acid molecule encoding a CAR polypeptide comprising the CDRs from the VL domains of SEQ ID NO:3 or SEQ ID NO:4. In some embodiments, the compositions of the invention comprise a recombinant cell having a nucleic acid molecule encoding a CAR polypeptide comprising the CDRs from VH and VL domains of SEQ ID NO:1 and SEQ ID NO:3. In some embodiments, the compositions of the invention comprise a recombinant cell having a nucleic acid molecule encoding a CAR polypeptide comprising the CDRs from VH and VL domains of SEQ ID NO:1 and SEQ ID NO:4. In some embodiments, the compositions of the invention comprise a recombinant cell having a nucleic acid molecule encoding a CAR polypeptide comprising the CDRs from VH and VL domains of SEQ ID NO:2 and SEQ ID NO:3. In some embodiments, the compositions of the invention comprise a recombinant cell having a nucleic acid molecule encoding a CAR polypeptide comprising the CDRs from VH and VL domains of SEQ ID NO:2 and SEQ ID NO:4. In some embodiments, the cell is a T-cell, a CD4 T-cell, a Treg cell, a CD8 alpha T-cell, CD8 beta T cell, T helper cell, granulocyte (neutrophils, basophils, eosinophils), megakaryocytes, monocyte, macrophage and a dendritic cell, or a T memory stem cell. In some embodiments, the cell is a Treg cell.

In some embodiments, the compositions of the invention comprise a recombinant cell having a nucleic acid molecule encoding a CAR polypeptide comprising the CDRs from VH and VL domains of SEQ ID NO:1 (SBT01 VH (M)) and SEQ ID NO:4 (SBT01 VL (G)). In some embodiments, the VH domain of the CAR polypeptide comprises a VH-CDR1 comprising the amino acid sequence of SEQ ID NO:32, a VH-CDR2 comprising the amino acid sequence of SEQ ID NO:34, and a VH-CDR3 comprising the amino acid sequence of SEQ ID NO:36, and the VL domain of CAR polypeptide comprises a VL-CDR1 comprising the amino acid sequence of SEQ ID NO:39, a VL-CDR2 comprising the amino acid sequence of SEQ ID NO:41, and a VL-CDR3 comprising the amino acid sequence of SEQ ID NO:43. In some embodiments, the cell is a T-cell, a CD4 T-cell, a Treg cell, a CD8 alpha T-cell, CD8 beta T cell, T helper cell, granulocyte (neutrophils, basophils, eosinophils), megakaryocytes, monocyte, macrophage and a dendritic cell, or a T memory stem cell. In some embodiments, the cell is a Treg cell.

In another embodiment, the compositions of the invention comprise a recombinant cell having a nucleic acid molecule encoding a CAR polypeptide comprising an scFV comprising one or more VH domains comprising the amino acid sequence of VH domains of SEQ ID NO:1 or SEQ ID NO:2. In some embodiments, the nucleic acid molecule encoding a CAR polypeptide comprises an scFV comprising an amino acid sequence having at least any of 80%, 85%, 90%, 95%, 97%, 98%, 99% or 99.5% of SEQ ID NO:1 or SEQ ID NO:2, provided the scFV domain binds to a citrullinated antigen as described herein. In some embodiments, the cell is a T-cell, a CD4 T-cell, a Treg cell, a CD8 alpha T-cell, CD8 beta T cell, T helper cell, granulocyte (neutrophils, basophils, eosinophils), megakaryocytes, monocyte, macrophage and a dendritic cell, or a T memory stem cell. In some embodiments, the cell is a Treg cell.

In some embodiments, the compositions of the invention comprise a recombinant cell having a nucleic acid molecule encoding a CAR polypeptide comprising an scFV comprising the VL domains of SEQ ID NO:3 or SEQ ID NO:4. In some embodiments, the nucleic acid molecule encoding a CAR polypeptide comprises an scFV comprising an amino acid sequence having at least any of 80%, 85%, 90%, 95%, 97%, 98%, 99% or 99.5% of SEQ ID NO: 3 or SEQ ID NO:4, provided the scFV domain binds to a citrullinated antigen as described herein. In some embodiments, the cell is a T-cell, a CD4 T-cell, a Treg cell, a CD8 alpha T-cell, CD8 beta cell, T helper cell, granulocyte (neutrophils, basophils, eosinophils), megakaryocytes, monocyte, macrophage and a dendritic cell, or a T memory stem cell. In some embodiments, the cell is a Treg cell.

In some embodiments, the compositions of the invention comprise a recombinant cell having a nucleic acid molecule encoding a CAR polypeptide comprising an scFV comprising the VH and VL domains of SEQ ID NO:1 and SEQ ID NO:3. In some embodiments, the nucleic acid molecule encoding a CAR polypeptide comprises an scFV comprising an amino acid sequence having at least any of 80%, 85%, 90%, 95%, 97%, 98%, 99% or 99.5% of SEQ ID NO: 1 or SEQ ID NO:3, provided the scFV domain binds to a citrullinated antigen as described herein. In some embodiments, the cell is a T-cell, a CD4 T-cell, a Treg cell, a CD8 alpha T-cell, CD8 beta T cell, T helper cell, granulocyte (neutrophils, basophils, eosinophils), megakaryocytes, monocyte, macrophage and a dendritic cell, or a T memory stem cell. In some embodiments, the cell is a Treg cell.

In some embodiments, the compositions of the invention comprise a recombinant cell having a nucleic acid molecule encoding a CAR polypeptide comprising an scFV comprising the VH and VL domains of SEQ ID NO:1 and SEQ ID NO:4. In some embodiments, the nucleic acid molecule encoding a CAR polypeptide comprises an scFV comprising an amino acid sequence having at least any of 80%, 85%, 90%, 95%, 97%, 98%, 99% or 99.5% of SEQ ID NO: 1 and SEQ ID NO:4, provided the scFV domain binds to a citrullinated antigen as described herein. In some embodiments, the cell is a T-cell, a CD4 T-cell, a Treg cell, a CD8 alpha T-cell, CD8 beta cell, helper cell, granulocyte (neutrophils, basophils, eosinophils), megakaryocytes, monocyte, macrophage and a dendritic cell, or a T memory stem cell. In some embodiments, the cell is a Treg cell.

In some embodiments, the compositions of the invention comprise a recombinant cell having a nucleic acid molecule encoding a CAR polypeptide comprising an scFV comprising the VH and VL domains of SEQ ID NO: 2 and SEQ ID NO:3. In some embodiments, the nucleic acid molecule encoding a CAR polypeptide comprises an scFV comprising an amino acid sequence having at least any of 80%, 85%, 90%, 95%, 97%, 98%, 99% or 99.5% of SEQ ID NO: 2 and SEQ ID NO: 3, provided the scFV domain binds to a citrullinated antigen as described herein. In some embodiments, the cell is a T-cell, a CD4 T-cell, a Treg cell, a CD8 alpha T-cell, CD8 beta T cell, T helper cell, granulocyte (neutrophils, basophils, eosinophils), megakaryocytes, monocyte, macrophage and a dendritic cell, or a T memory stem cell. In some embodiments, the cell is a Treg cell.

In some embodiments, the compositions of the invention comprise a recombinant cell having a nucleic acid molecule encoding a CAR polypeptide comprising an scFV comprising the VH and VL domains of SEQ ID NO:2 and SEQ ID NO:4. In some embodiments, the nucleic acid molecule encoding a CAR polypeptide comprises an scFV comprising an amino acid sequence having at least any of 80%, 85%, 90%, 95%, 97%, 98%, 99% or 99.5% of SEQ ID NO: 2 and SEQ ID NO: 4, provided the scFV domain binds to a citrullinated antigen as described herein. In some embodiments, the cell is a T-cell, a CD4 T-cell, a Treg cell, a CD8 alpha T-cell, CD8 beta T cell, T helper cell, granulocyte (neutrophils, basophils, eosinophils), megakaryocytes, monocyte, macrophage and a dendritic cell, or a T memory stem cell. In some embodiments, the cell is a Treg cell.

VI. Methods of Use

T cells, and in particular, Treg cells, that express the CARs disclosed herein are useful in the treatment of rheumatoid arthritis. Methods of use comprise administering an effective amount a pharmaceutical composition of this disclosure to a subject in need thereof, e.g., a subject suffering from rheumatoid arthritis.

As used herein, the term "subject" refers to an individual animal. The term "patient" as used herein refers to a subject under the care or supervision of a health care provider such as a doctor or nurse. Subjects include mammals, such as humans and non-human primates, such as monkeys, as well as dogs, cats, horses, bovines, rabbits, rats, mice, goats, pigs, and other mammalian species. Subjects can also include avians. A patient can be an individual that is seeking treatment, monitoring, adjustment or modification of an existing therapeutic regimen, etc. The term "rheumatoid arthritis subject" refers to an individual that has been diagnosed with rheumatoid arthritis. Rheumatoid arthritis patients can include individuals that have not received treatment, are currently receiving treatment, have had treatment, and those that have discontinued treatment.

As used herein, the terms "effective amount," "effective dose," and "therapeutically effective amount," refer to an amount of an agent that is sufficient to generate a desired response, such as reduce or eliminate a sign or symptom of a condition or ameliorate a disorder. In some examples, an "effective amount" is one that treats (including prophylaxis) one or more symptoms and/or underlying causes of any of a disorder or disease and/or prevents progression of a disease. For example, for the given parameter, a therapeutically effective amount will show an increase or decrease of therapeutic effect at least any of 5%, 10%, 15%, 20%, 25%, 40%, 50%, 60%, 75%, 80%, 90%, or at least 100%. Therapeutic efficacy can also be expressed as "-fold" increase or decrease. For example, a therapeutically effective amount can have at least any of a 1.2-fold, 1.5-fold, 2-fold, 5-fold, or more effect over a control.

The pharmaceutical composition can be administered by any suitable route, including but not limited to intravenous, subcutaneous, intramuscular or intraperitoneal routes. An example of administration of a pharmaceutical composition includes storing the composition at 10 mg/ml in sterile isotonic aqueous saline solution for injection at 4° C., and diluting it in either 100 ml or 200 ml 0.9% sodium chloride for injection prior to administration to the patient. The pharmaceutical composition is administered by intravenous infusion over the course of 1 hour at a dose of between 0.2 and 10 mg/kg. In other embodiments, the pharmaceutical composition is administered by intravenous infusion over a period of between 15 minutes and 2 hours. In still other embodiments, the administration procedure is via sub-cutaneous bolus injection.

The dose of the composition is chosen in order to provide effective therapy for the patient and is in the range of less than 0.1 mg/kg body weight to about 25 mg/kg body weight or in the range 1 mg-2 g per patient. In some cases, the dose is in the range 1-100 mg/kg, or approximately 50 mg-8000 mg/patient. The dose may be repeated at an appropriate frequency which may be in the range once per day to once every three months, depending on the pharmacokinetics of the composition (e.g., half-life of the composition in the circulation) and the pharmacodynamic response (e.g., the duration of the therapeutic effect of the composition). In some embodiments, the in vivo half-life of between about 7 and about 25 days and composition dosing is repeated between once per week and once every 3 months.

Administration can be periodic. Depending on the route of administration, the dose can be administered, e.g., once every 1, 3, 5, 7, 10, 14, 21, or 28 days or longer (e.g., once every 2, 3, 4, or 6 months). In some cases, administration is more frequent, e.g., 2 or 3 times per day. The patient can be monitored to adjust the dosage and frequency of administration depending on therapeutic progress and any adverse side effects, as will be recognized by one of skill in the art.

Thus, in some embodiments, additional administration is dependent on patient progress, e.g., the patient is monitored between administrations. For example, after the first administration or round of administrations, the patient can be monitored for rate of tumor growth, recurrence (e.g., in the case of a post-surgical patient), or general disease-related symptoms such as weakness, pain, nausea, etc.

In certain embodiments, the T cells described herein are administered to the synovia of the joints of subjects having rheumatoid arthritis. Such administration can be by injection directly into the joint.

An exemplary method of this disclosure includes isolating T lymphocytes from a biological sample obtained from the subject. Such T cell can be isolated by immunoaffinity, for example, using solid supports derivatized and anti-CD4 antibodies. CD4+ T regulatory cells (Treg) can be separated from non-Treg cells based on their marker profile. Treg cells are CD4+, CD25+, CD127lo. Non Treg cells are: CD4+, CD25+ and CD127+. The isolated Treg cells are then transfected with an expression vector encoding a chimeric antigen receptor (CAR) of this disclosure. The transfected cells are expanded. The expanded cells are administered to the subject.

VII. Kits

As used herein, the term "kit" refers to a collection of items intended for use together. The kit can optionally include a reference agent and/or instructions for use thereof. A kit can further include a shipping container adapted to hold a container, such as a vial, that contains a composition as disclosed herein. A kit can include a container that contains within it the collection of items.

Kits of this disclosure can comprise a pharmaceutical composition as described herein, contained in a container, such as a bag or bottle for intravenous administration. Also included in the kit can be a fluidic conduit, such as a plastic tube, with a drip chamber. The drip chamber can communicate through a fluidic conduit with an intravenous needle. The fluidic conduit also can comprise one or more Y-sites and a roller clamp.

EXAMPLES

Abbreviations: CAR (chimeric antigen receptor); CF (citrullinated fibrinogen); CFSE (carboxyfluorescein succinimidyl ester); CV (citrullinated vimentin); EGFR (epidermal growth factor receptor); IN (intranasal); IV (intravenous); LPS (lipopolysaccharide); PAD2 (peptidylarginine deiminase 2); PBMC (peripheral blood mononuclear cells); PBS (phosphate buffered saline); RA (rheumatoid arthritis); scFv (single-chain variable fragment); SF (synovial fluid); Teff (effector T cell); Treg (regulatory T cell); and UTD (untransduced).

Example 1: SBT01G Consistently Performed as Well as, or Superior to BVCA1 in a Luciferase System Jurkat-FF-Luciferase Transduction—50,000 cells per well were plated in each of 2 flat-bottom 96-well plates in RPMI with 2× protamine sulfate. Viruses were diluted in RPMI such that 100 µl is approx. an MOI of 1. Then 100 µl was added to one column on each 96-well plate. Plates were then spun and placed in an incubator. Samples were pooled the next day. Transduced cells were resuspended in media and transferred 100 µl to a U-bottom plate in duplicate. The cells were stained with CV-AF488 and CV-AF647 with 1:100 anti-EGFR-PE at 4° C. for 20 mins, washed once, then analyzed by Novocyte. Samples were then scaled up into 6-well plates by adding 3 ml fresh media Plate Coating—Citrullinated vimentin (CV) was first diluted 1:100 into 4 ml PBS. 5 serial 4-dilutions were made by transferring 1 ml into 3 ml. 100 µl was then added to 96-well plates. Plates were placed at 4° C. to coat overnight.

Luciferase Assay—Normalized transduced cells were pelleted and resuspended in 1 ml RPMI. The CV-coated plates were washed three times with PBS. 50 µl of cells were added to the plates. 25 µl of 3×PMA/Iono were added, and the plates were placed in the 37° C. incubator. Approximately 24 hours later, the luciferase plates were read by adding 75 µl BioGlo reagent, incubating 2-3 mins in the dark and reading the plate.

FIG. 1 shows the response of virus transduced Jurkat-FF-Luciferase cells to different concentrations of full CV coated plates. The results show that BVCA1 and STB01 had the strongest response to plate-bound, full-length CV.

Figure 2:
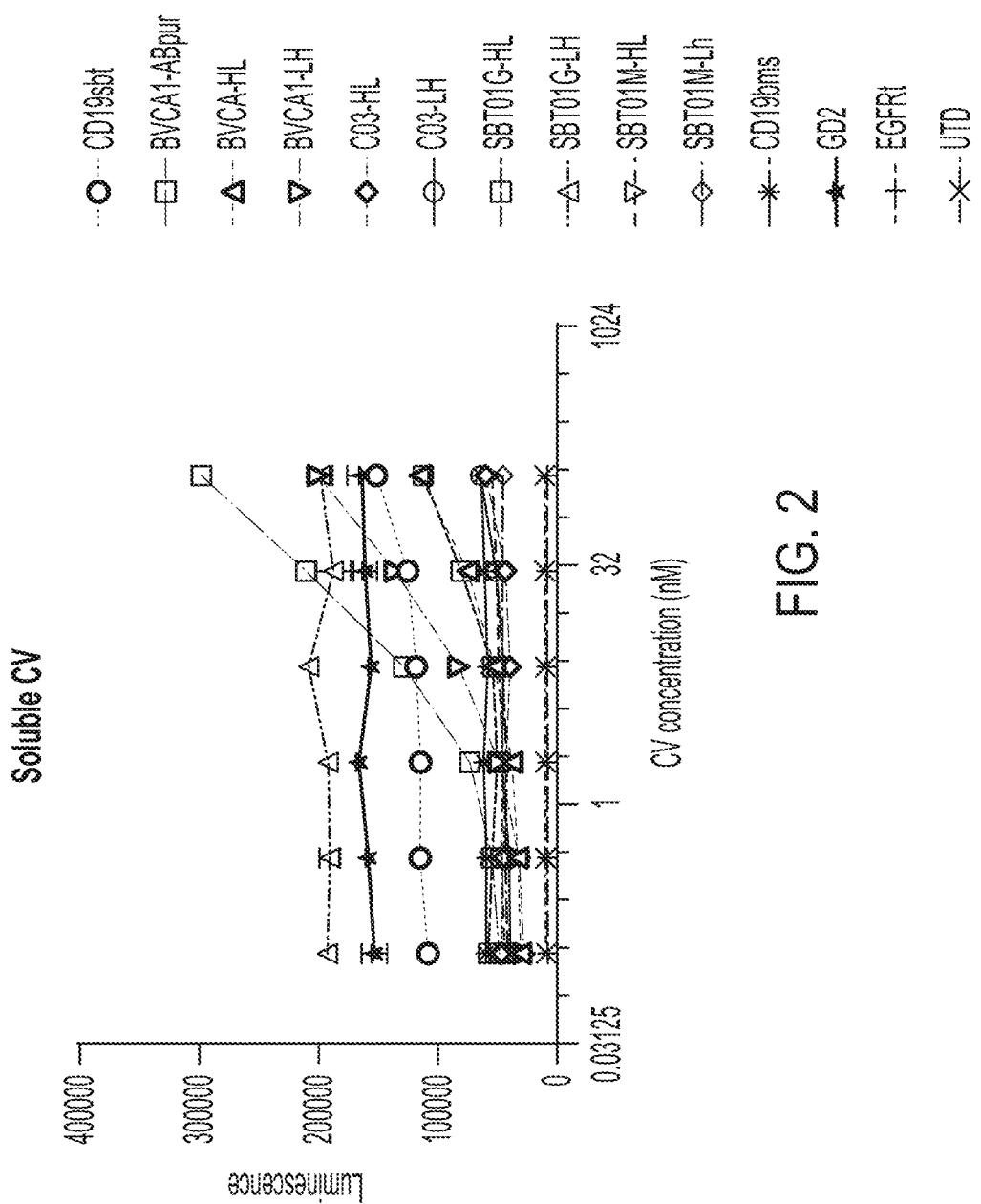
FIG. 2: Assay with soluble full-length CV showed a dose response only for CV CARs BVCA1 and SBT01G-HL (n=1).

FIG. 2 shows the response of virus transduced Jurkat-FF-Luciferase cells to different concentrations of soluble CV. The results show that only BVCA1 and SBT01G-HL had a dose-dependent response to soluble, full-length CV.

Figure 3:
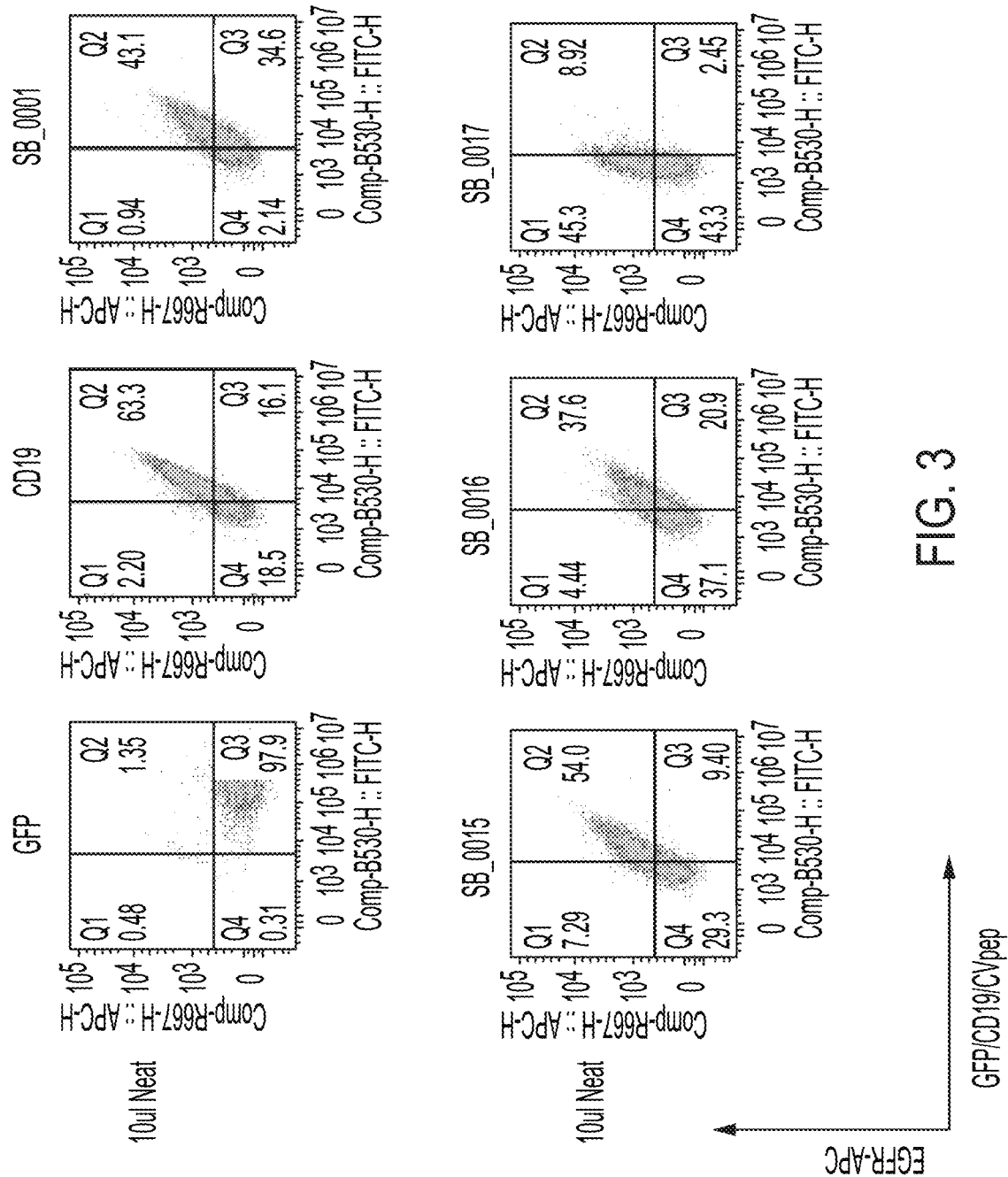
FIG. 3: Assay with soluble bead-bound-peptide demonstrated binding specificity (n=1).
Figure 3:
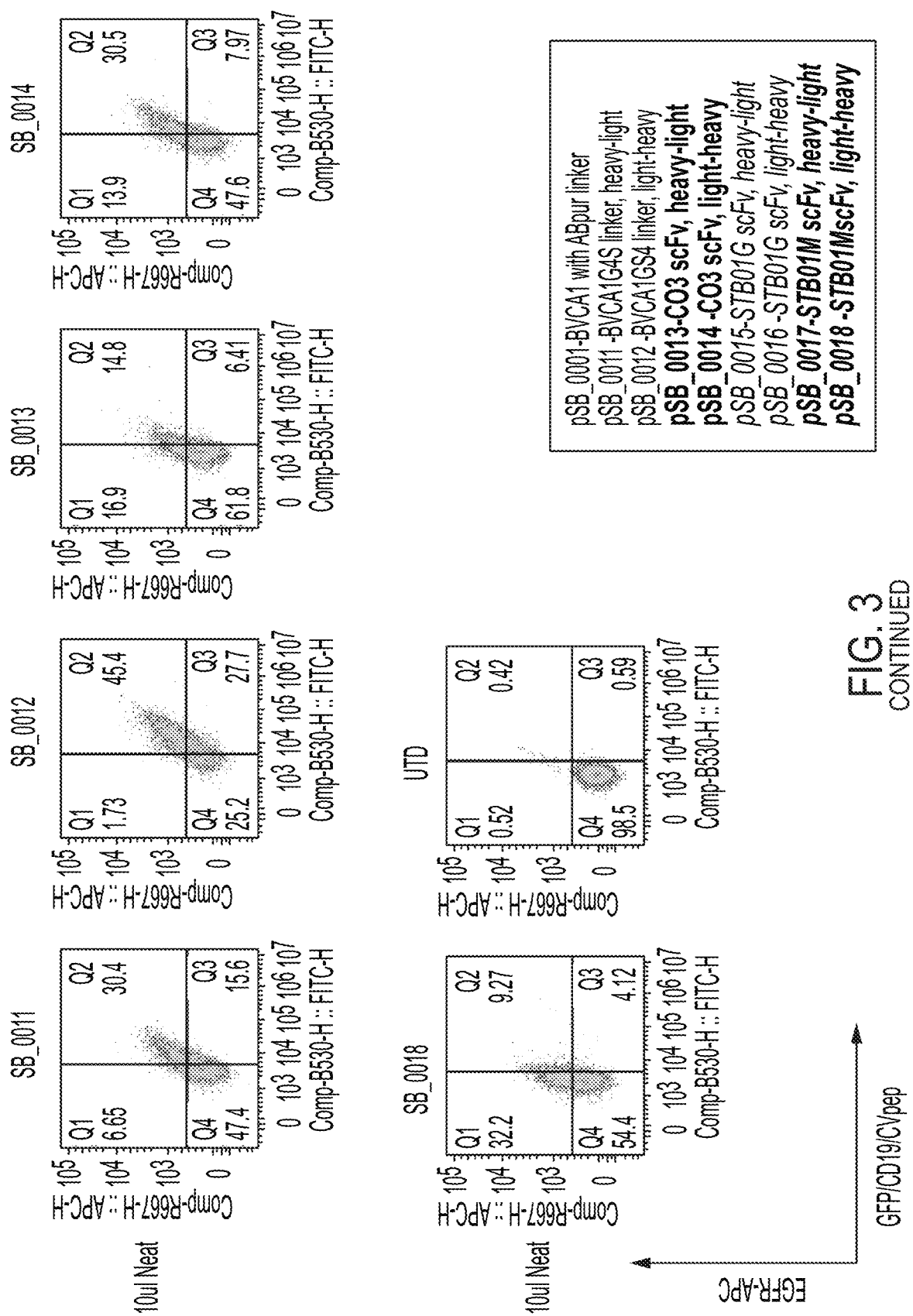

FIG. 3 shows that in an assay with soluble bead-bound-peptide, BVCA1 and SBT01 demonstrated binding specificity to CV.

Figure 4:
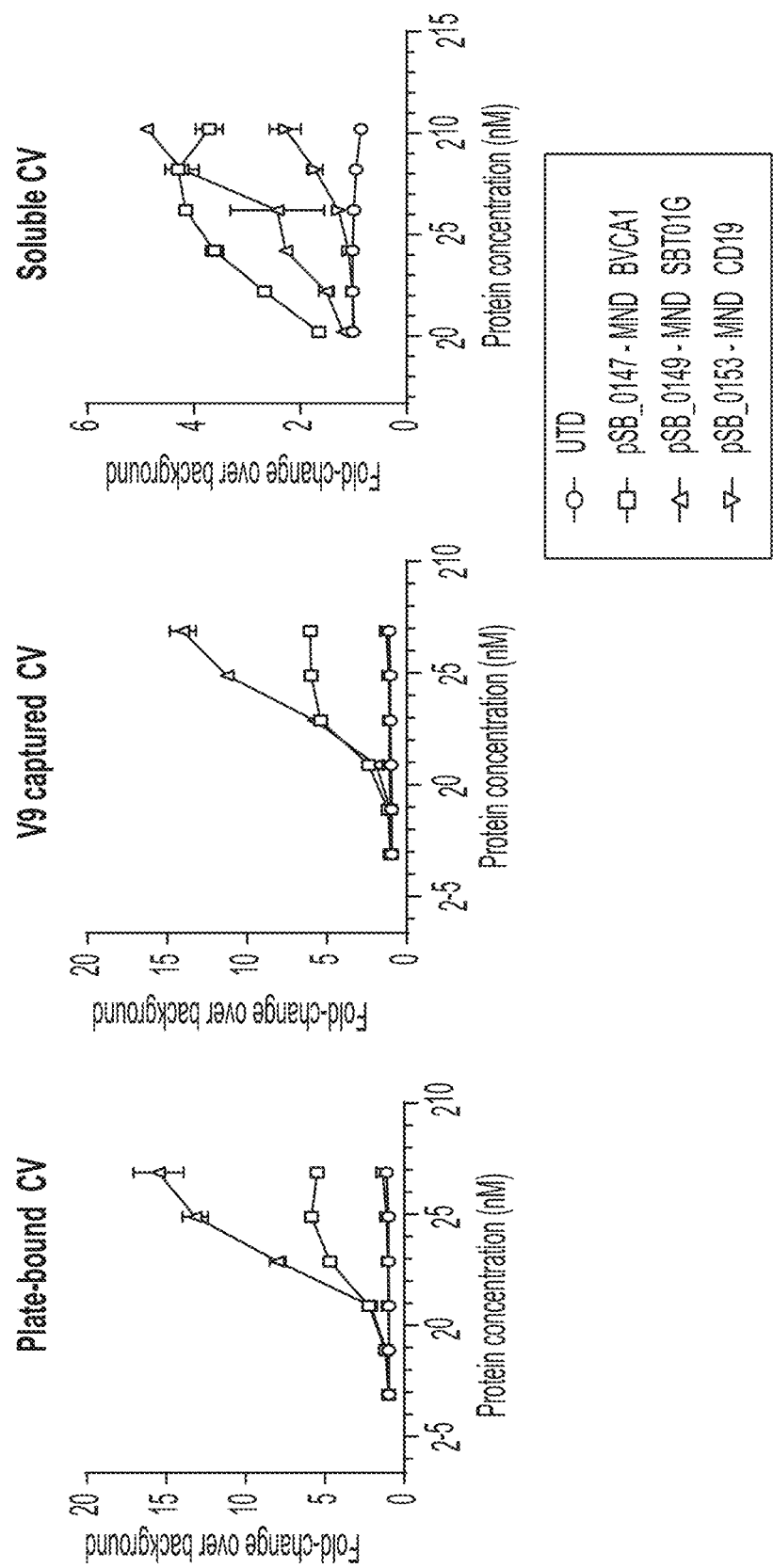
FIG. 4: MND-SBT01G shows a stronger response to plate-bound, antibody captured CV, but not soluble CV than MND-BVCA1.

FIG. 4 shows the response of BVCA1 and SBT01G to plate-bound CV, antibody (V9) captured CV, and soluble CV at different protein concentrations. The results show that SBT01G has a stronger response to plate-bound CV and antibody (V9) captured CV, but not soluble CV, than BVCA1.

Example 2: SBT01 and BVCA1 Respond to Synovial Fluids from Rheumatoid Arthritis Patients Jurkat-FF-Luciferase transduction—24×10⁶ Jurkat-FF-luc cells were pelleted and resuspended in 24 ml RPMI containing protamine sulfate and virus at a MOI of 3, to express CARs of pSB_0147, pSB-0149 and pSB0139. Cells were mixed and 4 ml were aliquoted into each well of a 6-well plate. Plates were then spun and placed in an incubator overnight. Cells were pelleted and reseeded in 25 ml RPMT in T75 flasks.

Synovial Fluid Stimulus—Transduced cells were pelleted and resuspended in RPMI and placed in wells of black/white plates. Synovial fluid (SF) samples from RA patients were thawed, vortexed, and diluted in RPMI before being added to plates containing transduced cells. Cells were cultured with SF at 37° C.

Luciferase Assay—Approximately 24 hours later, 75 µl BioGlo reagent was added to each well, and the plates were incubated 2-3 mins in the dark. Luminescence was then read on a plate reader.

Treg isolation and Tissue Culture—Primary human Treg cells were sourced from healthy donors from leukoreduction chamber residuals or leukopaks. Peripheral blood mononuclear cells (PBMC) were isolated by density gradient centrifugation using Ficoll-Paque Plus. CD25+ cells were enriched by positive selection. Treg cells were next isolated using FACS by gating for CD4+CD25+CD127lo cells. After isolation, cells were stimulated with CTS Dynabeads Treg Xpander (Gibco) at a 1:1 bead to cell ratio and cultured in RPMI medium, supplemented with 10% FBS, non-essential amino acids, sodium pyruvate, and beta-mercaptoethanol with recombinant human IL-2 at 300 IU/mL at a density of 0.25-0.3 million cells/mL. On day 9 of expansion, fresh CTS Dynabeads Treg Xpander were added at a 1:1 bead to cell ratio.

Transduction of Primary Tregs—Primary Tregs were transduced with CV-CAR constructs on day 2 of expansion via spin-osculation in the presence of protamine sulfate.

Activation of Tregs—CV-CAR-expressing Treg cells were cultured in vitro with a dilution of synovial fluid samples ranging from 1:5 to 1:160. Treg activation was assessed by measurement of CD71 expression.

Flow Cytometry and FACS Analysis—Activation cultures were collected and centrifuged at 300×g for 5 min and then resuspended in 1× Flowstain Buffer (Invitrogen) with a viability dye (Invitrogen), anti-EGFR and CD71 surface staining antibody. Tregs were incubated for 30 min at 4° C., then centrifuged and washed with 1× Flow stain Buffer. Stained cells were fixed with CytoFix (BD Biosciences) then analyzed by flow cytometry.

Figure 5:
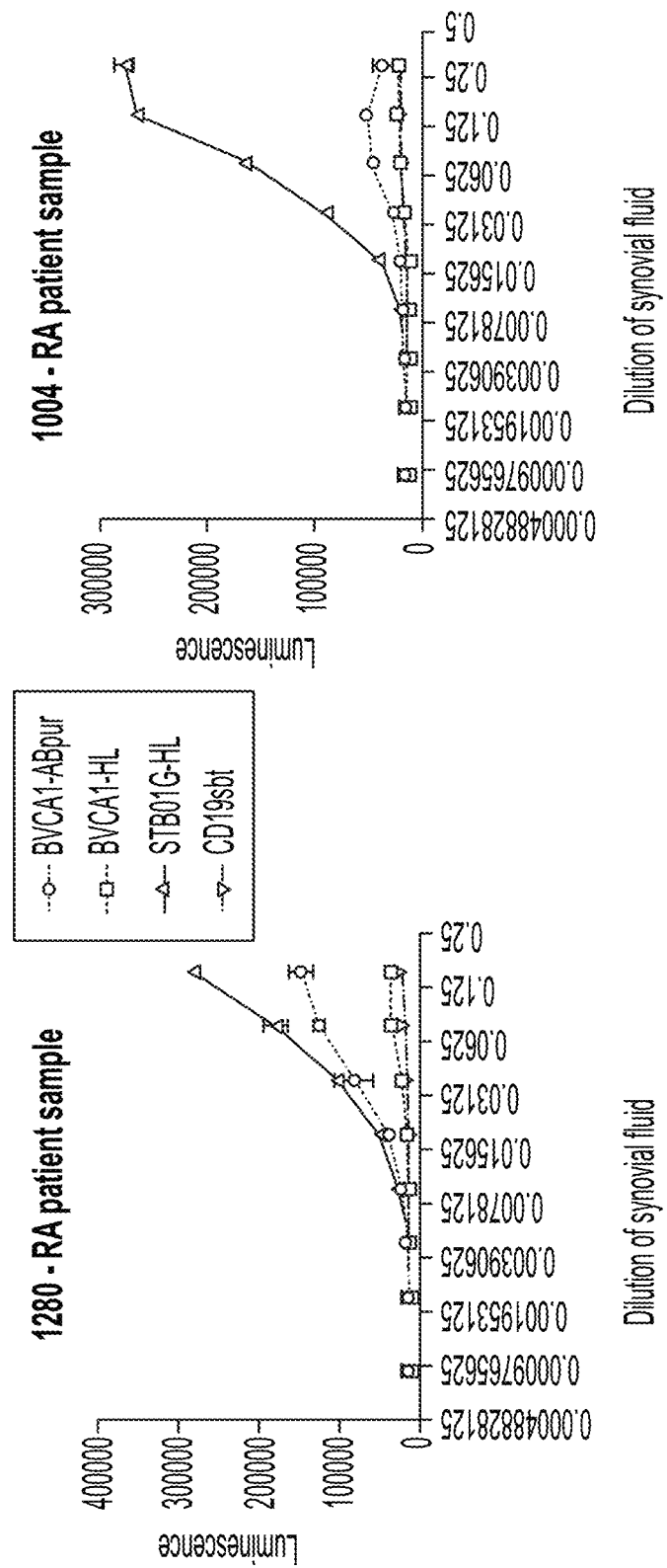
FIG. 5: Testing of an initial batch of synovial fluid from Innovative Research showed SBT01G gave stronger responses than BVCA1.
Figure 5:
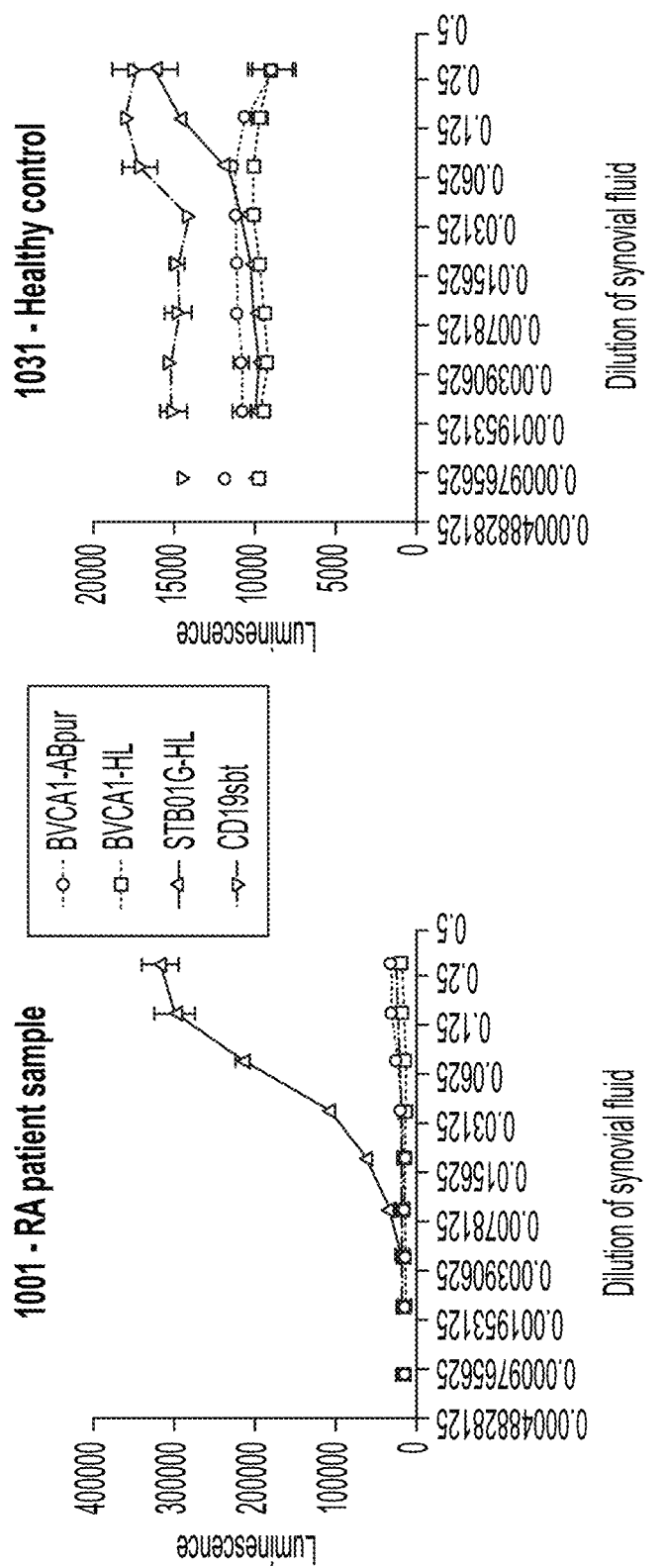

FIG. 5 shows the response of SBT01G and BVCA1 to synovial fluids from RA patients. The data shows that SBT01G gave stronger responses than BVCA1 to synovial fluids from several RA patients.

Figure 6:
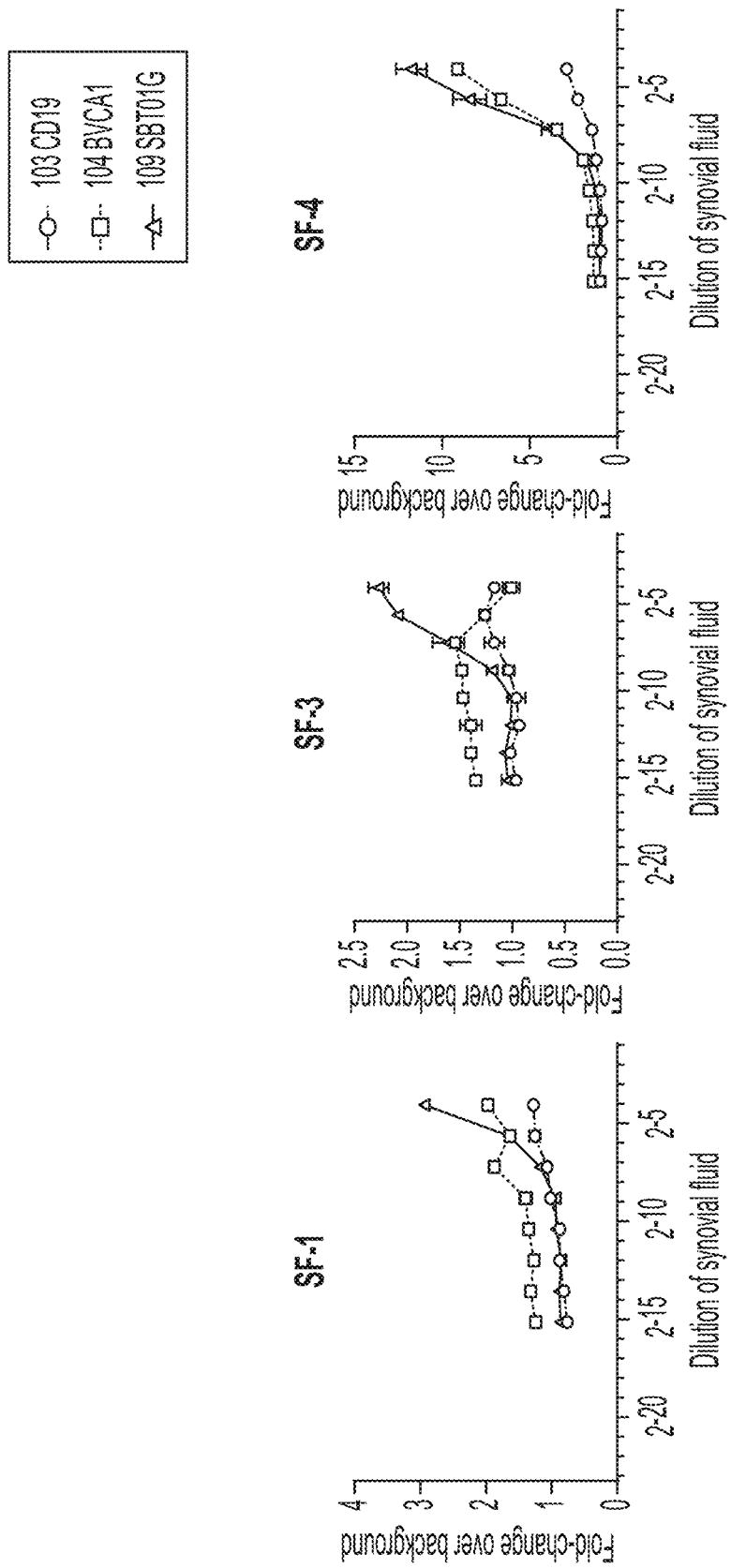
FIG. 6: Further testing of 15 synovial fluid samples from Swedish patients showed that, for samples that gave a response, SBT01G was stronger than BVCA1.
Figure 6:
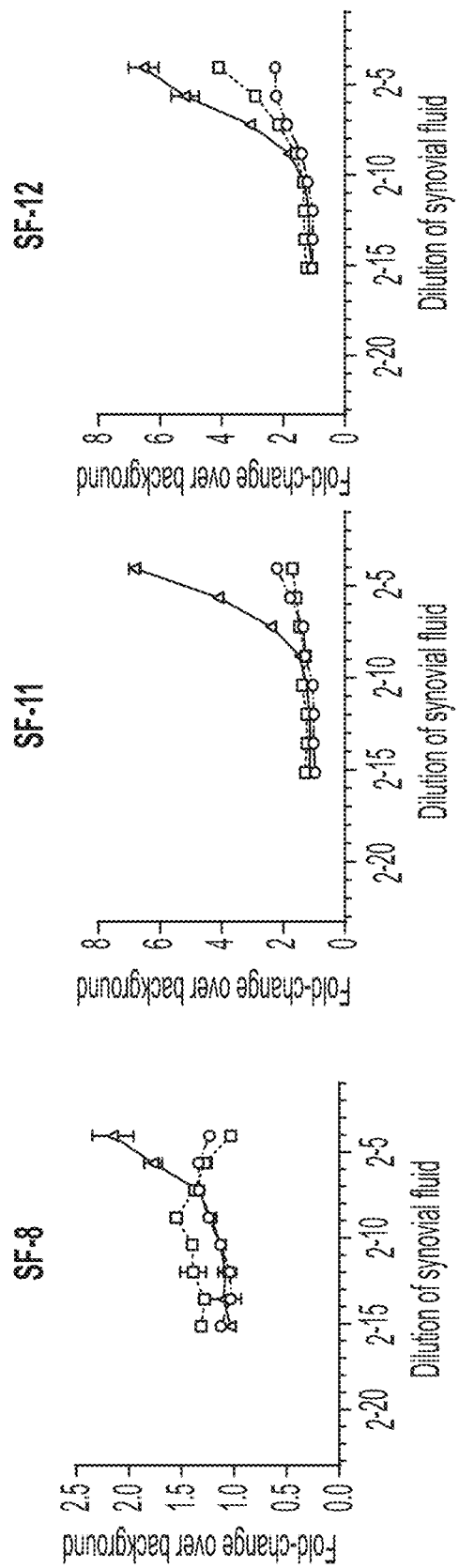

FIG. 6 shows for synovial fluid samples from Swedish RA patients that triggered a response, that SBT01G was again stronger than BVCA1.

Figure 7:
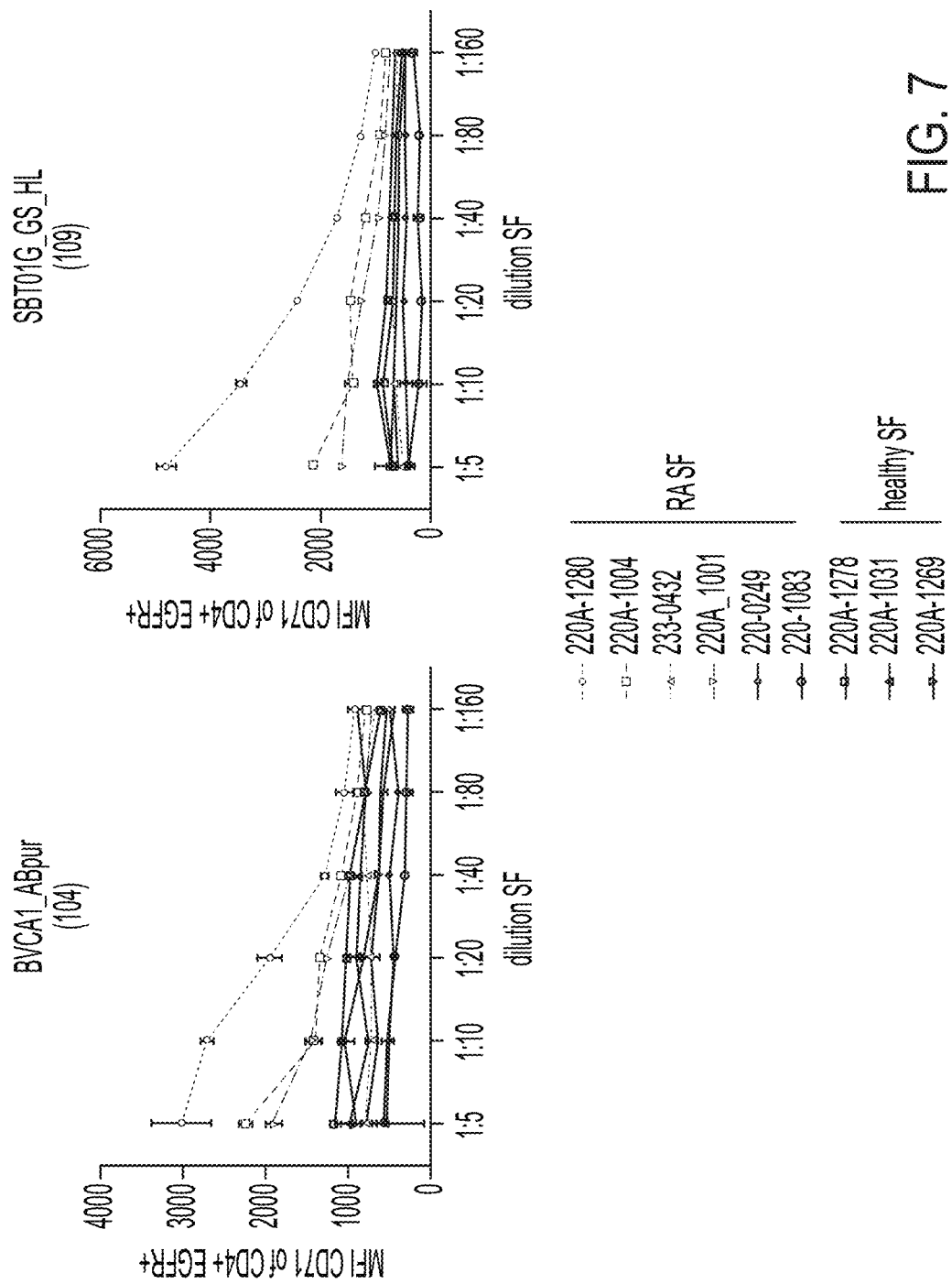
FIG. 7: Primary Treg responses to synovial fluid (SF) demonstrate SBT01G is more sensitive than BVCA1 to SF from RA patients.

FIG. 7 shows responses of primary Treg cells transduced with CV-CARs to synovial fluid from multiple RA patients. The primary Treg cells expressing the SBT01G CAR are more sensitive to synovial fluid from RA patients than primary Treg cells expressing the BVCA1 CAR.

Example 3: SBT01 and BVCA1 Response to Citrullinated Fibrinogen

Plate Coating—Citrullinated protein was diluted in PBS and added to wells of a black/white isoplate. Plates were placed at 4° C. overnight to coat the plate wells.

Luciferase Assay—Stably-transduced and untransduced (UTD) Jurkat-FF-luc cell lines were pelleted and resuspended in RPMI containing 10% FBS. The citrullinated protein-coated plates were washed three times with PBS. 50,000 cells per well in 75 μl were added the coated plates. 5 μl of 15×PMA/Iono in RPMI were added to each well, and the plates were placed in the 37° C. incubator. Approximately 24 hours later, 75 μl BioGlo reagent was added to each well, and the plates were incubated 2-3 mins in the dark. Luminescence was then read on a plate reader.

Treg Isolation and Tissue Culture—Primary human Treg cells were sourced from healthy donors from leukoreduction chamber residuals or leukopaks. Peripheral blood mononuclear cells (PBMC) were isolated by density gradient centrifugation using Ficoll-Paque Plus. CD25+ cells were enriched by positive selection. Treg cells were next isolated using FACS by gating for CD4+CD25+CD127lo cells and left were isolated using FACS gating for CD4+ CD25loCD127pos. After isolation, cells were stimulated with CTS Dynabeads Treg Xpander (Gibco) at a 1:1 bead to cell ratio and cultured in RPMI medium, supplemented with 10% FBS, non-essential amino acids, sodium pyruvate, and b-mercaptoethanol with recombinant human IL-2 at 300 IU/mL at a density of 0.25-0.3 million cells/mL. On day 9 of expansion fresh CIS Dynabeads Treg Xpander were added at a 1:1 bead to cell ratio.

Transduction of Primary Tregs and Teffs—Primary Tregs and Teff were transduced with CD19-CAR or CV-CAR constructs on day 2 of expansion via spin-occulation in the presence of protamine sulfate.

Activation of Tregs—Before start of activation cultures CAR expressing Tregs and Teff were labelled with a proliferation dye, CFSE. CD19-CAR and CV-CAR-expressing Treg cells were cultured in vitro with plate-coated citrullinated vimentin (CV) or citrullinated fibrinogen (CF) ranging in dose from 30 ng/ml to 10 μg/ml. Treg activation was assessed by measurement of percentages of proliferating cells and by CD71 expression.

Flow Cytometry and FACS Analysis—Activation cultures were collected and centrifuged at 300×g for 5 min and then resuspended in 1× Flowstain Buffer (Invitrogen) with a viability dye (Invitrogen), anti-EGFR and CD71 surface staining antibody. Tregs were incubated for 30 min at 4° C., then centrifuged and washed with 1× Flowstain Buffer. Stained cells were fixed with CytoFix (BD Biosciences) then analyzed by flow cytometry.

Figure 8:
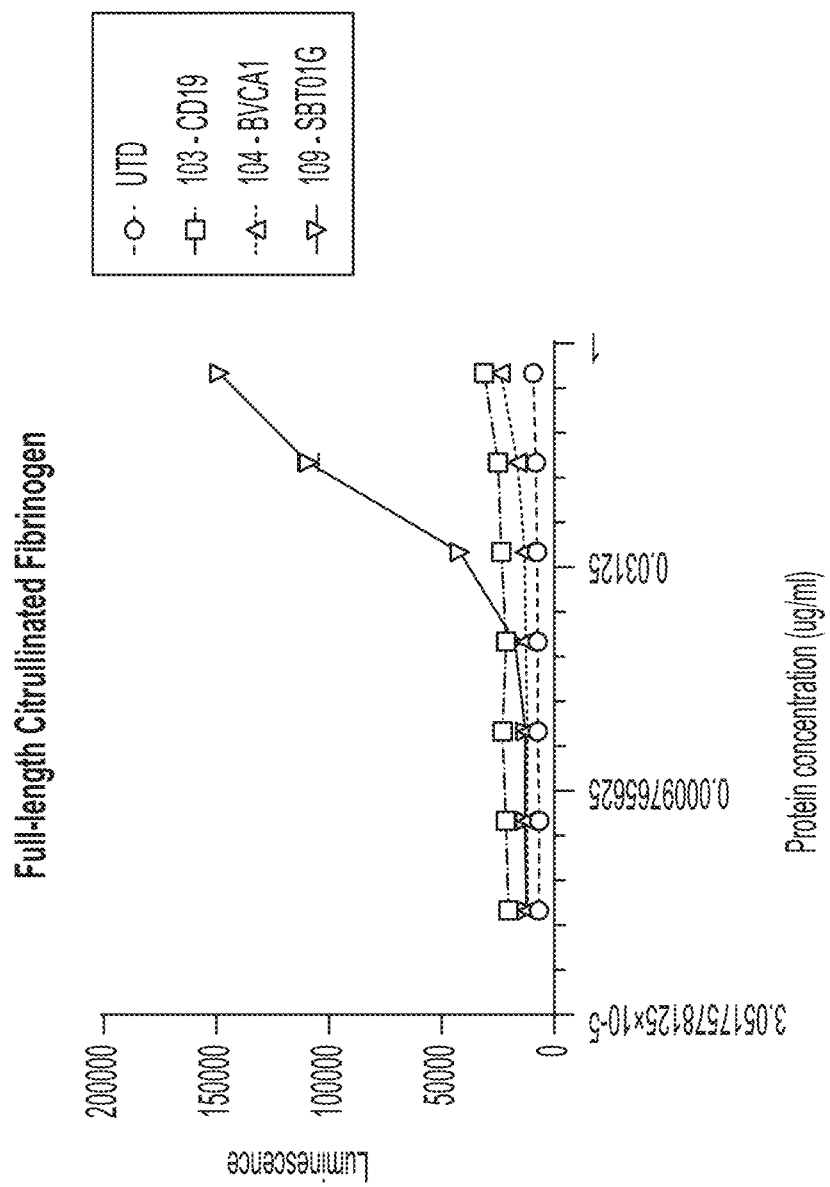
FIG. 8: SBT01G, but not BVCA1, is also able to respond to plate-bound full-length PAD2 citrullinated fibrinogen.

FIG. 8 shows responses of SBT01G and BVCA1 to plate-bound, full-length peptidylarginine deaminase 2 (PAD2)-citrullinated fibrinogen. The results show that SBT01G, but not BVCA1, is also able to respond to plate-bound, full-length PAD2-citrullinated fibrinogen.

FIG. 9 shows that SBT01G CAR expressed on Teff cells and Treg cells respond to citrullinated vimentin (CV) and citrullinated fibrinogen (CF). In contrast, BVCA1 CAR expressed on Teff cells and Treg cells respond to CV, but not to CF.

Thus, FIGS. 1-9 show that SBT01G consistently performed as well as, or superior to BVCA1 in all assay systems.

Example 4: CV CARS Demonstrate Functional Responses When Different Promoters and Linkers Are Used Treg Isolation and Tissue Culture—Primary human Treg cells were sourced from healthy donors from leukoreduction chamber residuals or leukopaks. Peripheral blood mononuclear cells (PBMC) were isolated by density gradient centrifugation using Ficoll-Paque Plus. CD25+ cells were enriched by positive selection. Treg cells were next isolated using FACS by gating for CD4+CD25+CD127lo cells. After isolation, cells were stimulated with CTS Dynabeads Treg Xpander (Gibco) at a 1:1 bead to cell ratio and cultured in RPMI medium, supplemented with 10% FBS, non-essential amino acids, sodium pyruvate, and b-mercaptoethanol with recombinant human IL-2 at 300 IU/mL at a density of 0.25-0.3 million cells/mL. On day 9 of expansion fresh CTS Dynabeads Treg Xpander were added at a 1:1 bead to cell ratio.

Transduction of Primary Tregs—Primary Tregs were transduced with CV-CAR constructs on day 2 of expansion via spin-occulation in the presence of protamine sulfate.

Activation of Tregs—Before start of activation cultures, CAR expressing Tregs were labelled with a proliferation dye, CFSE. CV-CAR-expressing Treg cells were cultured in vitro with bead captured CV peptide. Treg activation was assessed by measurement of percentages of proliferating cells.

Flow Cytometry and FACS Analysis Activation Assay—Activation cultures were collected and centrifuged at 300×g for 5 min and then resuspended in 1× Flowstain Buffer (Invitrogen) with a viability dye (Invitrogen) and anti-EGFR surface staining antibody. Tregs were incubated for 30 min at 4° C., then centrifuged and washed with 1× Flowstain Buffer. Stained cells were fixed with CytoFix (BD Biosciences) then analyzed by flow cytometry.

Flow Cytometry and FACS Analysis of Treg phenotype—On Day 14 of expansion untransduced (UTD), CD19-CAR and CV-CAR expressing Tregs were stained for transcription factors FoxP3 and Helios. Cells were fixed and permeabilized using eBiosciences FoxP3 transcription factor buffer set (eBiosciences).

Resting of Treg Cultures—On day 14 of expansion CD19-CAR and CV-CAR expressing Tregs were harvested, debeaded using a magnet and put in culture with 300 IU/ml IL-2 only at 0.5 million cells/ml Flow Cytometry and FACS Analysis of CAR Expression—CD19-CAR and CV-CAR expressing Tregs on day 14 of expansion and after 2 or 5 days of rest were stained with viability dye (Invitrogen) and anti-EGFR surface staining antibody. CV-CAR expression was detected by incubating the cells with 1 µg/ml CV, followed by FITC-labelled anti-vimentin (clone V9, Invitrogen).

Plate Coating—Citrullinated vimentin (CV) was diluted in PBS and added to wells of a black/white isoplate. Plates were placed at 4° C. overnight to coat the plate wells.

Luciferase Assay—Stably-transduced and untransduced (UTD) Jurkat-FF-luc cell lines were pelleted and resuspended in RPMI containing 10% FBS. The citrullinated protein-coated plates were washed three times with PBS. 50,000 cells per well in 75 µl were added the coated plates. 5 µl of 15×PMA/Iono in RPMI were added to each well, and the plates were placed in the 37° C. incubator. Approximately 24 hours later, 75 µl BioGlo reagent was added to each well, and the plates were incubated 2-3 mins in the dark. Luminescence was then read on a plate reader.

Figure 10A:
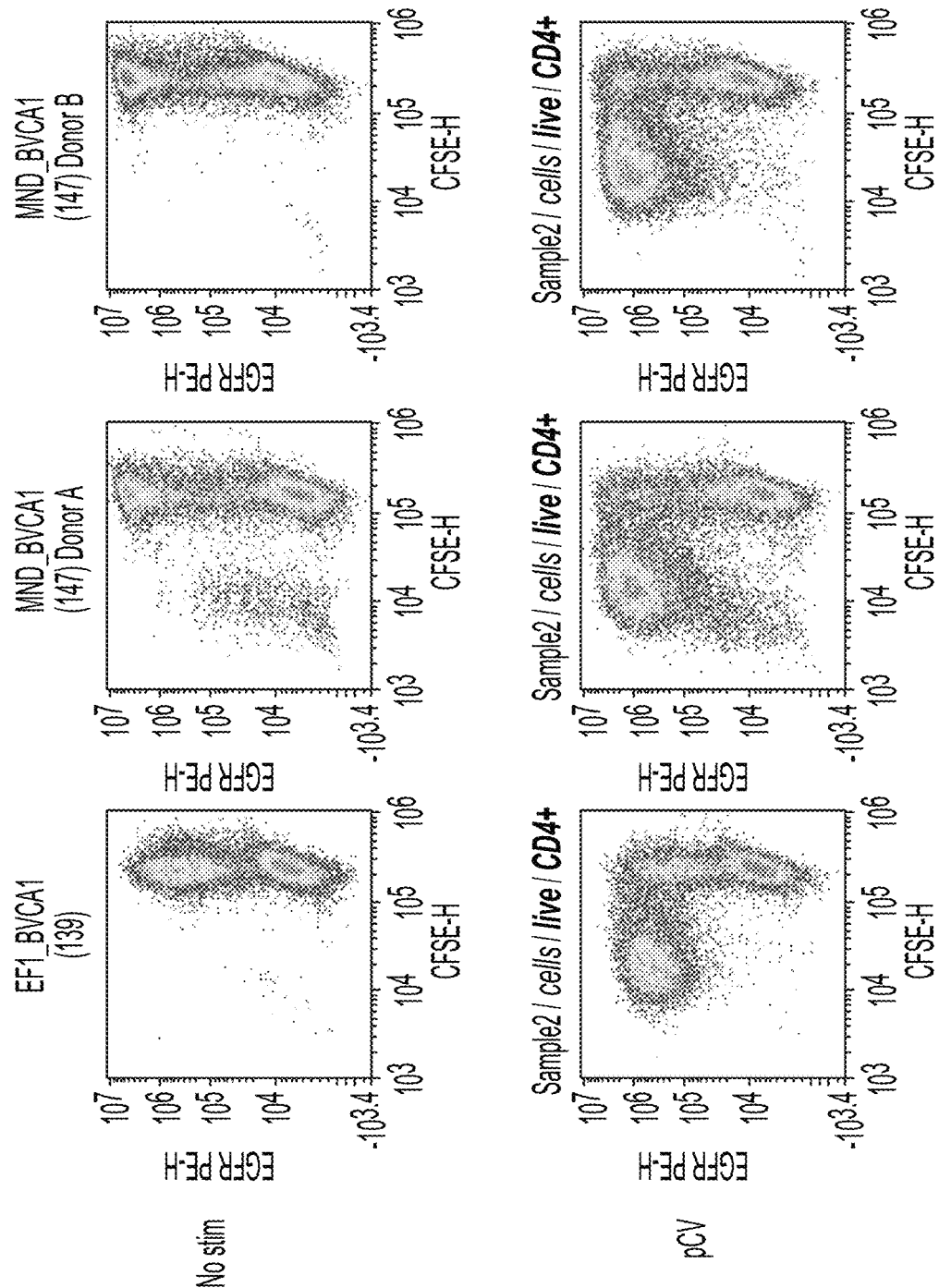
FIG. 10A-10B: Both EF1A and MND promoters demonstrate functional responses by CV CARs to soluble bead-bound-peptide. Thus, the CAR promoter does not influence Treg phenotype.
Figure 10A:
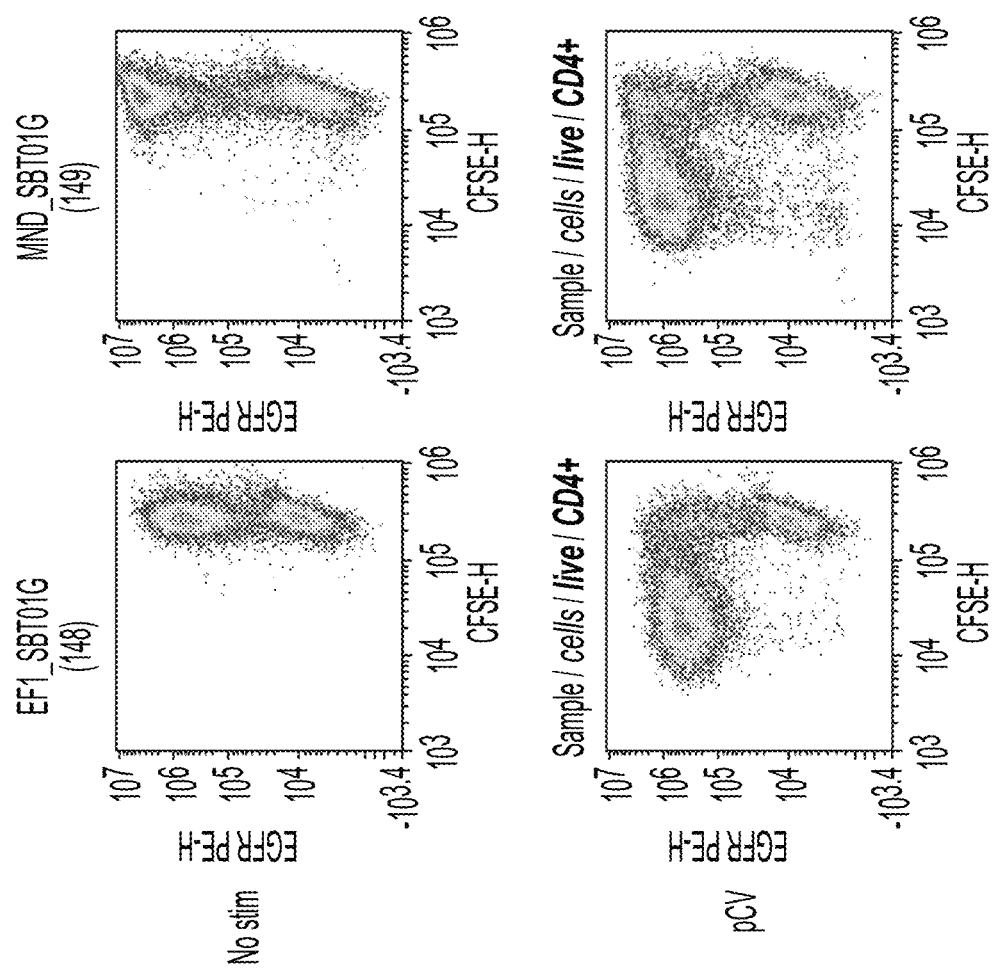
Figure 10B:
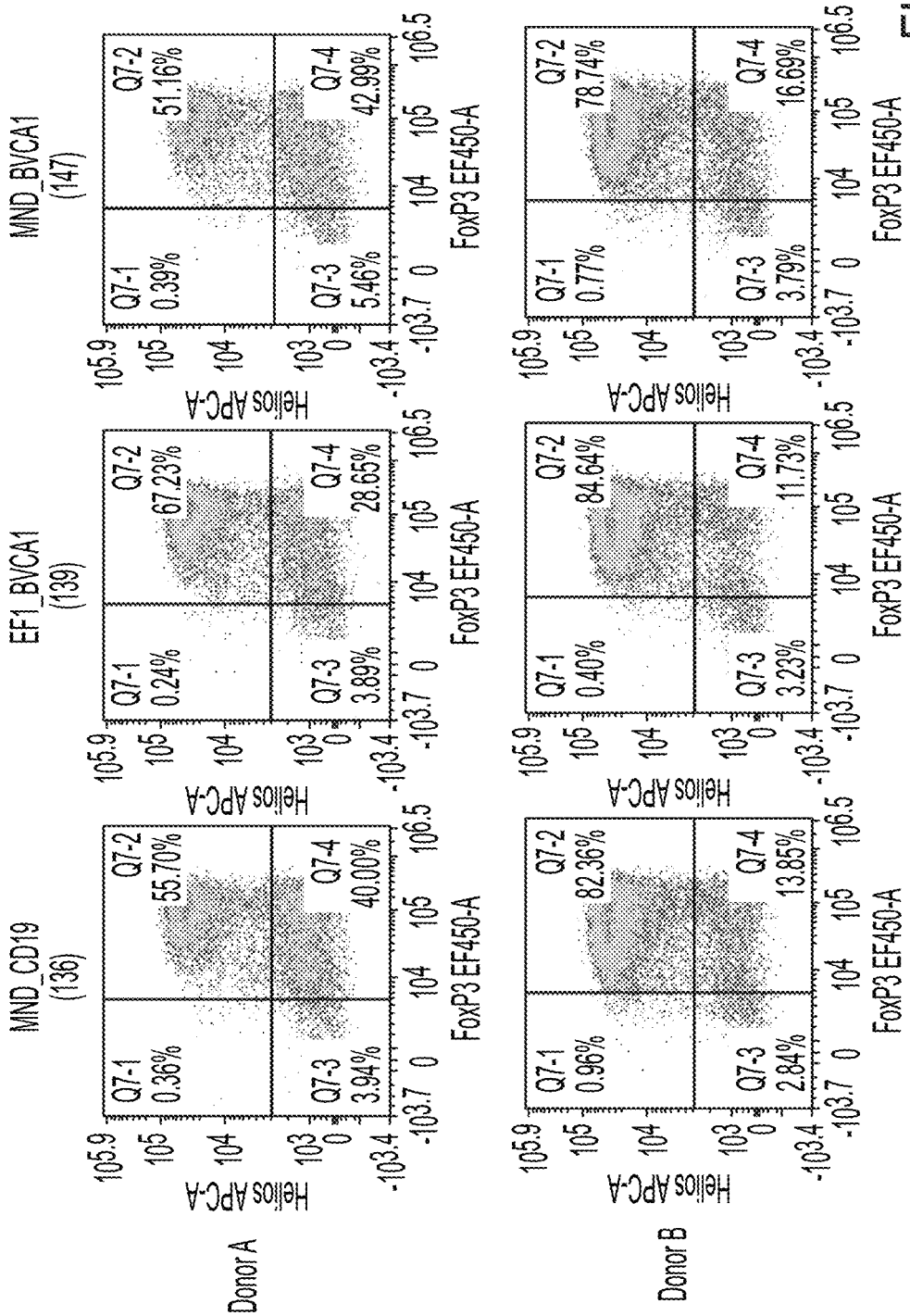
Figure 10B:
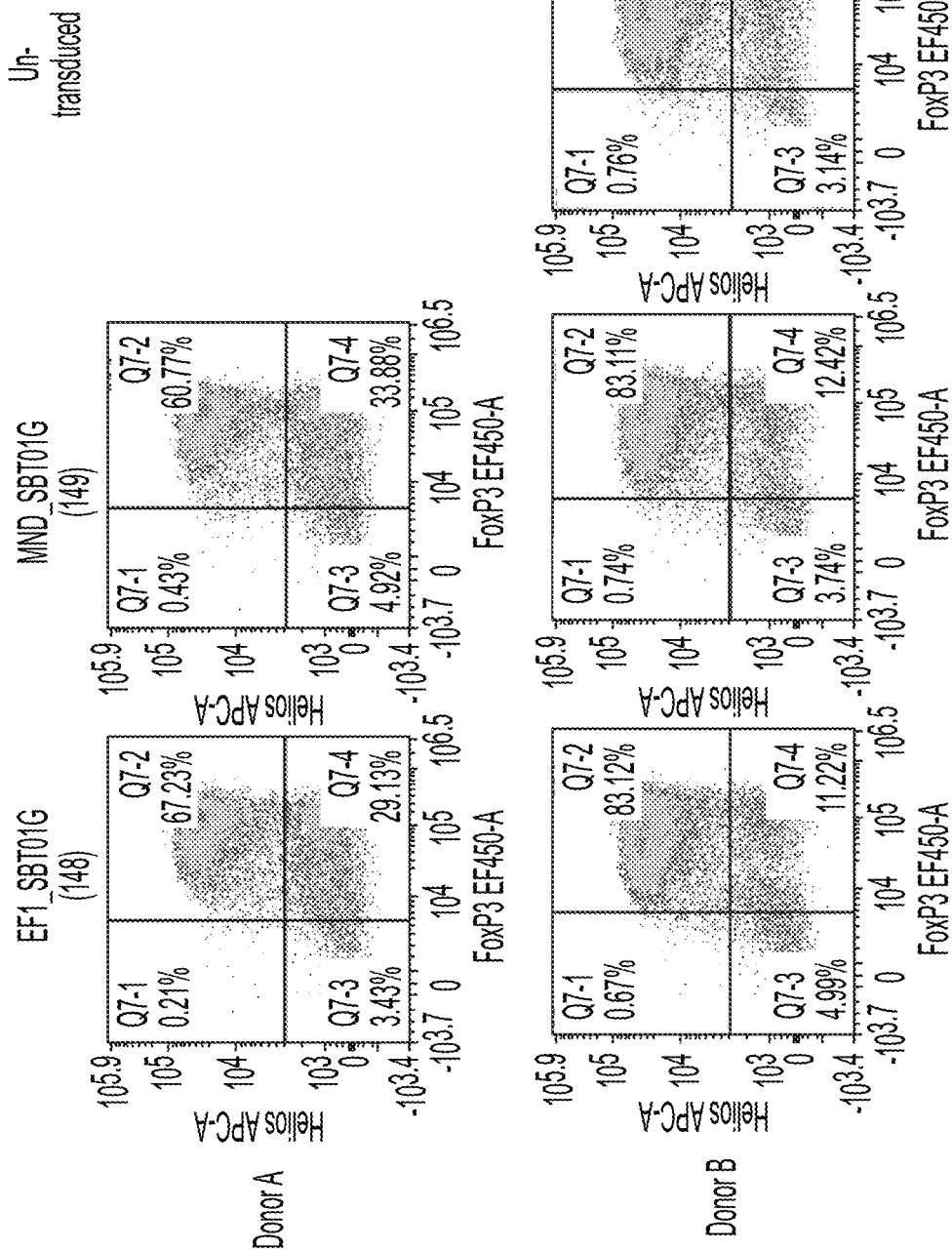

FIG. 10A shows that both EF1A and MND promoters drive expression and functional responses by CV-CAR T cells to soluble bead-bound citrullinated peptide (pCV). FIG. 10B shows that the use of different promoters does not change the phenotype of CV-CAR Treg cells.

Figure 11:
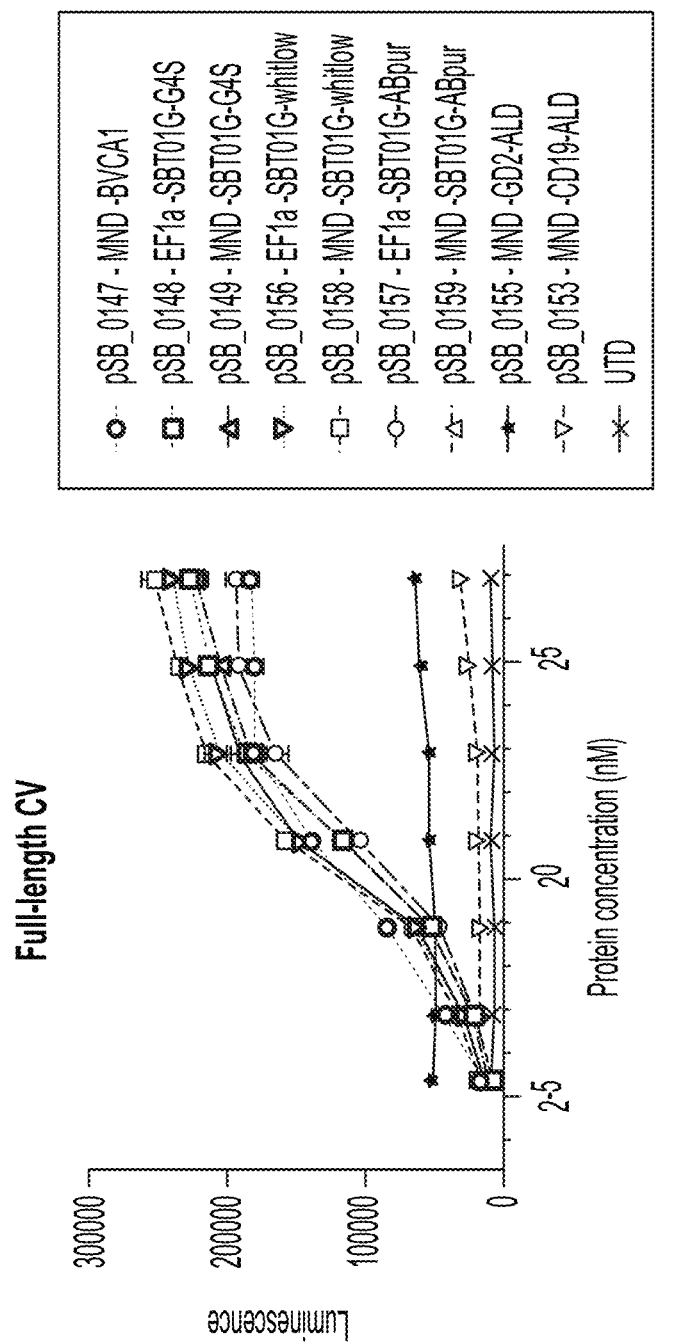
FIG. 11: scFv linker has little to no impact on SBT01G CAR-based function.

FIG. 11 shows that the choice of scFv linker has little to no impact on SBT01G CAR T cell responses to full length CV.

Figure 12A:
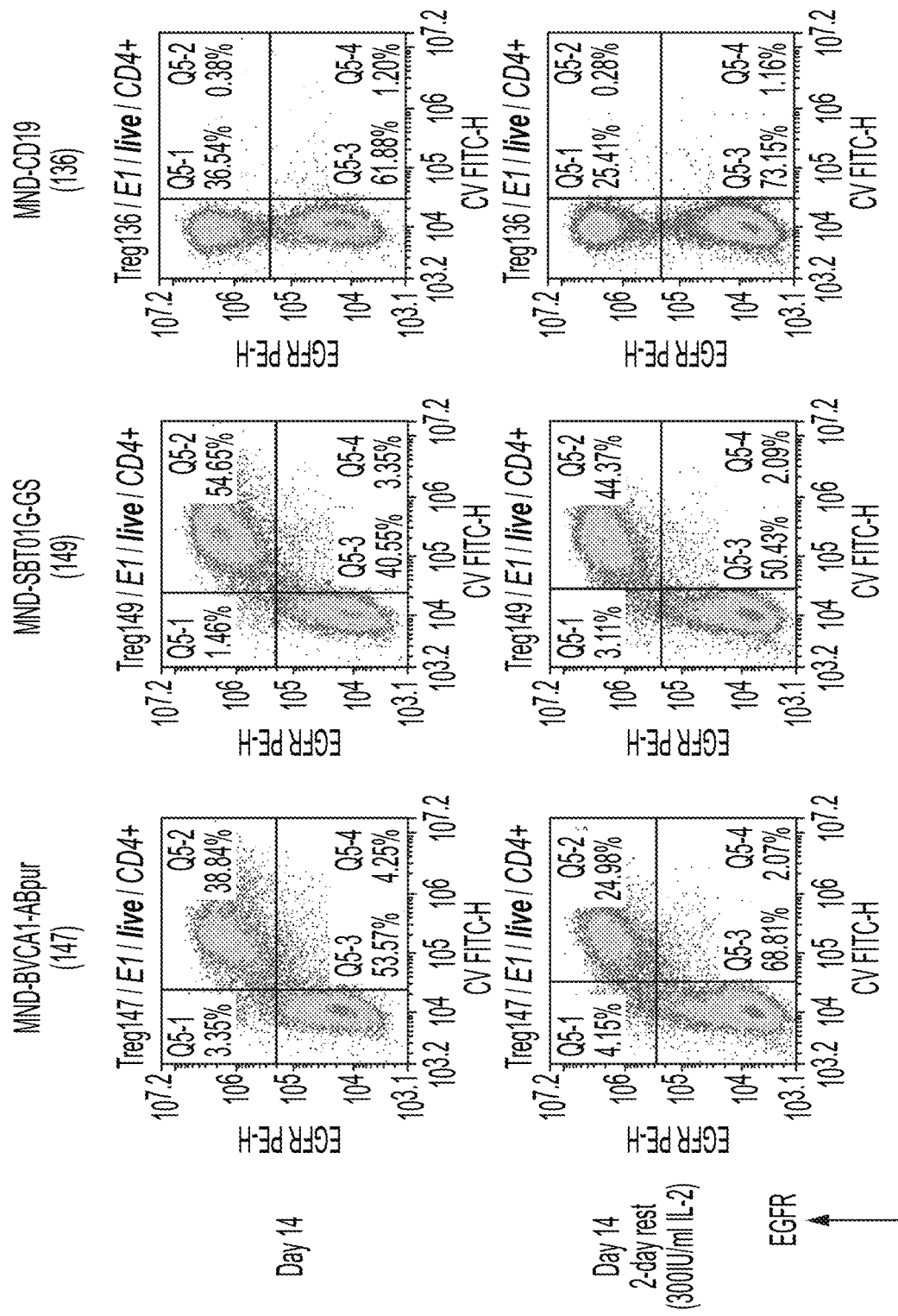
FIG. 12A-12B: SBT01G is expressed by a higher percentage of cells than BVCA1, but BVCA1 and SBT01G CAR-T cells have similar FoxP3 and Helios profiles.

FIG. 12A shows that transduction with the SBT01G CAR vector resulted in CV-CAR expression in a higher percentage of cells than did transduction with the BVCA1 CAR vector. FIG. 12B shows that SBT01G CAR and BVCA1 CAR Treg cells have similar FoxP3 and Helios profiles.

Figure 12A:
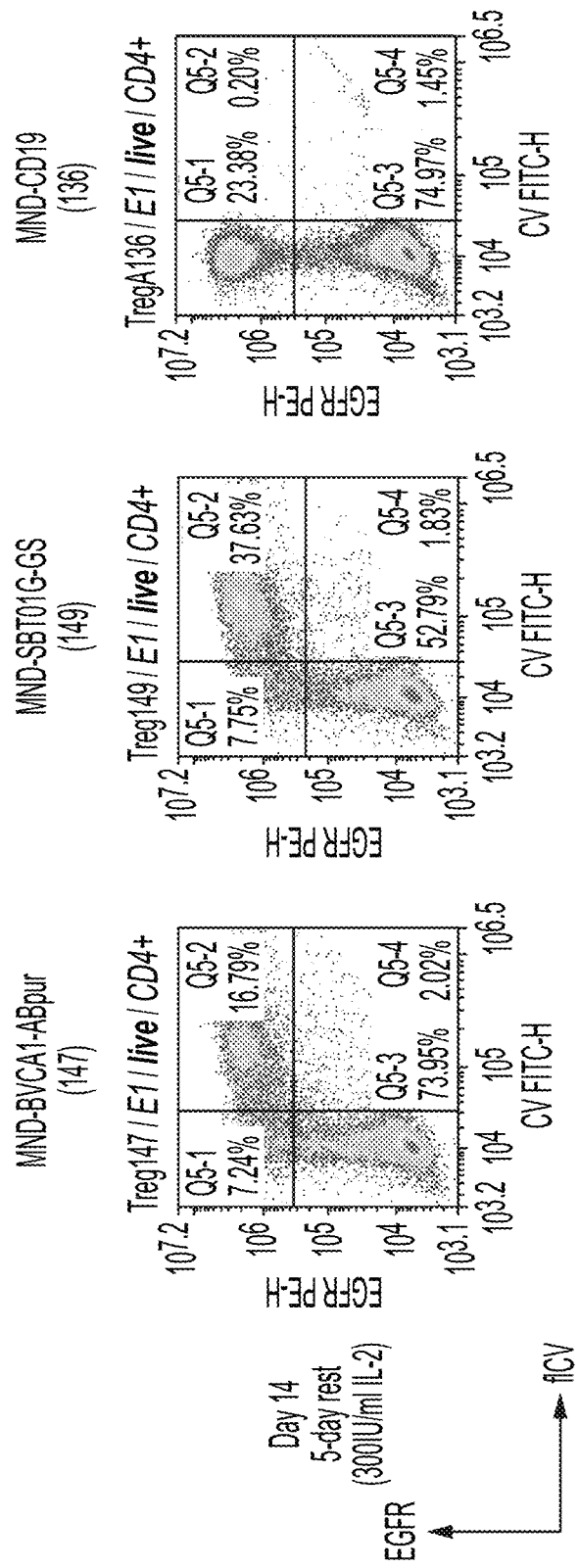
Figure 12B:
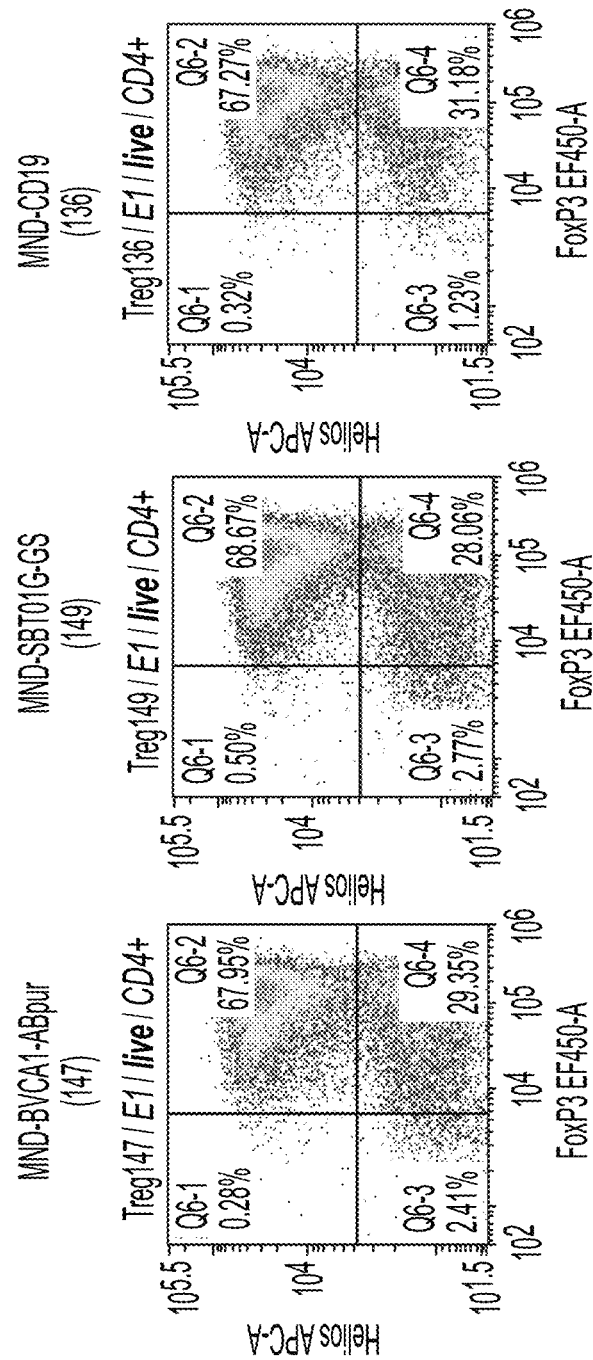

Thus, FIGS. 10-12 show that SBT01G showed higher percentage of CAR-positive Tregs, and SBT01G showed higher levels of CAR expression.

Example 5: Assessment of CV-CAR Treg Activation by Citrullinated Vimentin In Vitro Treg Isolation and Tissue Culture Primary human Treg cells were sourced from healthy donors from leukoreduction chamber residuals or leukopaks. Peripheral blood mononuclear cells (PBMC) were isolated by density gradient centrifugation using Ficoll-Paque Plus. CD25+ cells were enriched by positive selection. Treg cells were next isolated using FACS by gating for CD4+CD25+CD127lo cells. After isolation, cells were stimulated with CTS Dynabeads Treg Xpander (Gibco) at a 1:1 bead to cell ratio and cultured in RPMI medium, supplemented with 10% FBS, non-essential amino acids, sodium pyruvate, and penicillin/streptomycin with recombinant human IL-2 at 300 IU/mL at a density of 0.25-0.3 million cells/mL.

Activation of Tregs—Untransduced and CV-CAR-expressing Treg cells were cultured in vitro with the citrullinated vimentin antigen ranging in dose from 10 ng/mL to 10 µg/mL. Treg activation was assessed by measurement of percentages of proliferating cells, and levels of CD71 expression and IL-10 secretion.

Flow cytometry and FACS analysis: Untransduced and CV-CAR-expressing Treg cells were collected and centrifuged at 300×g for 5 min and then resuspended in 1× RoboSep Buffer (StemCell Technologies) with a CD71 surface staining antibody and Cell Trace Violet (CTV) viability dye cocktail (Invitrogen). Tregs were incubated for 30 min at 4° C., then centrifuged and washed with 1× RoboSep Buffer. Stained cells were then analyzed by flow cytometry.

Results

Figure 13:
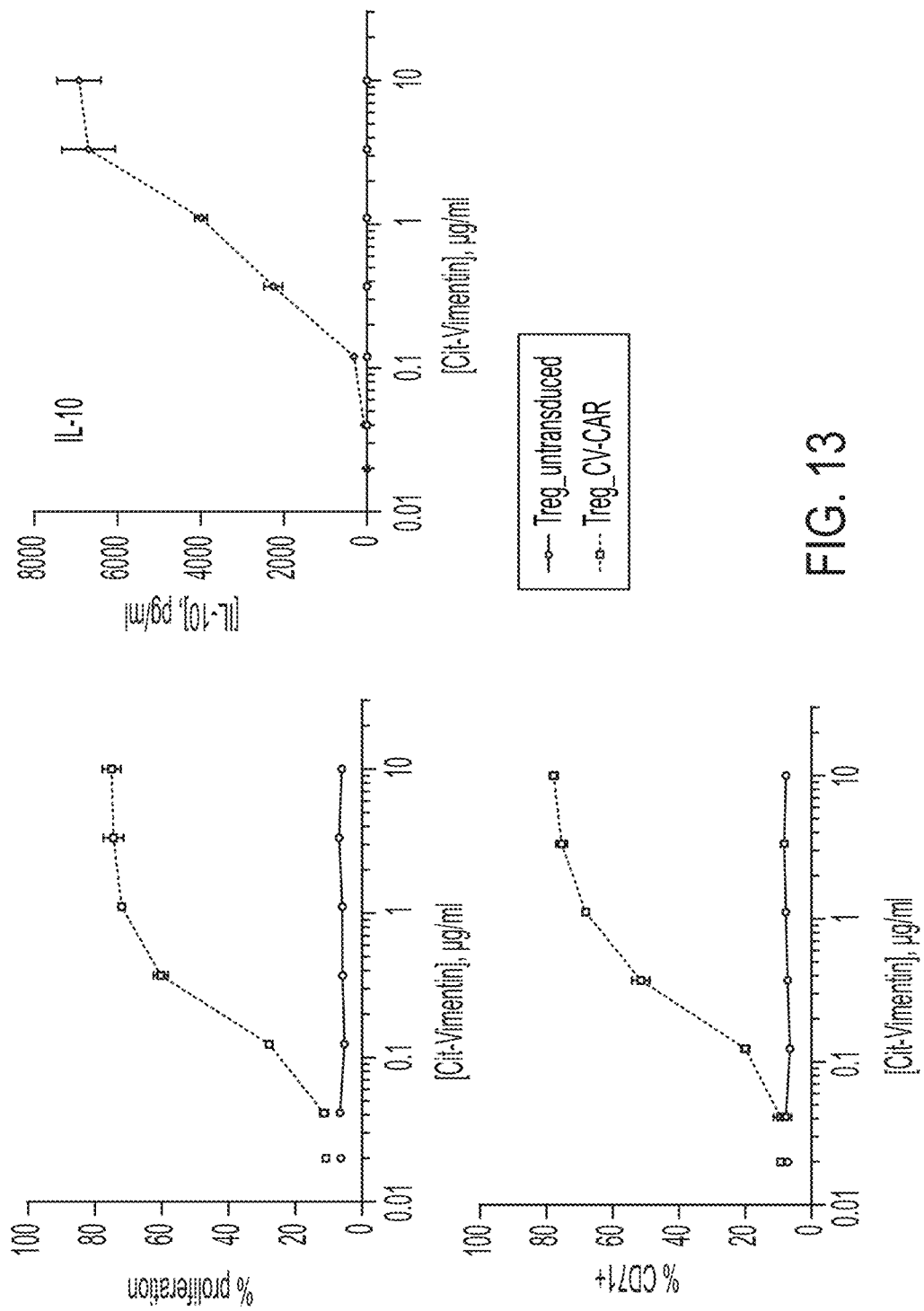
FIG. 13: CV-CAR Treg cells (SBT01G) but not untransduced Treg cells are activated by citrullinated vimentin (CV). Activation was demonstrated by target antigen-specific increases in proliferation, CD71 expression and IL-10 secretion.

Treg activation in response to citrullinated vimentin (CV) was assessed in vitro. FIG. 13 shows a dose-dependent, CV-induced activation of CV-CAR Treg cells, as demonstrated by increases in proliferating cells, CD71 expression and IL-10 secretion. In contrast, untransduced Treg cells were not activated by CV. These results demonstrate that Treg activation upon stimulation with CV is specific to Tregs expressing a CV-CAR.

Figure 14:
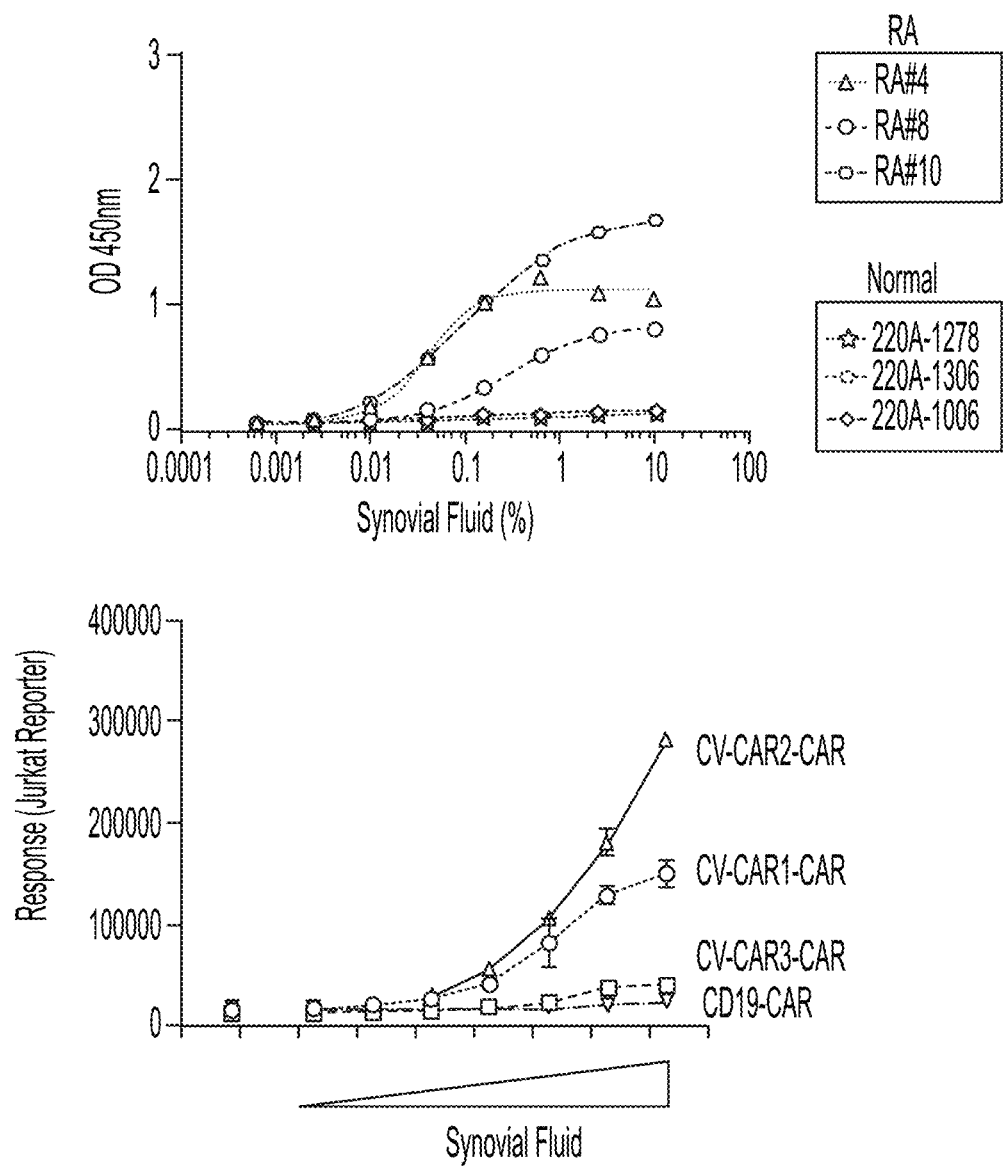
FIG. 14: CV-CAR Treg cells respond to citrullinated proteins in the synovial fluid from the majority of RA patients. In contrast, CV-CAR Treg cells do not respond to synovial fluid from normal controls (subjects without RA).
Figure 14:
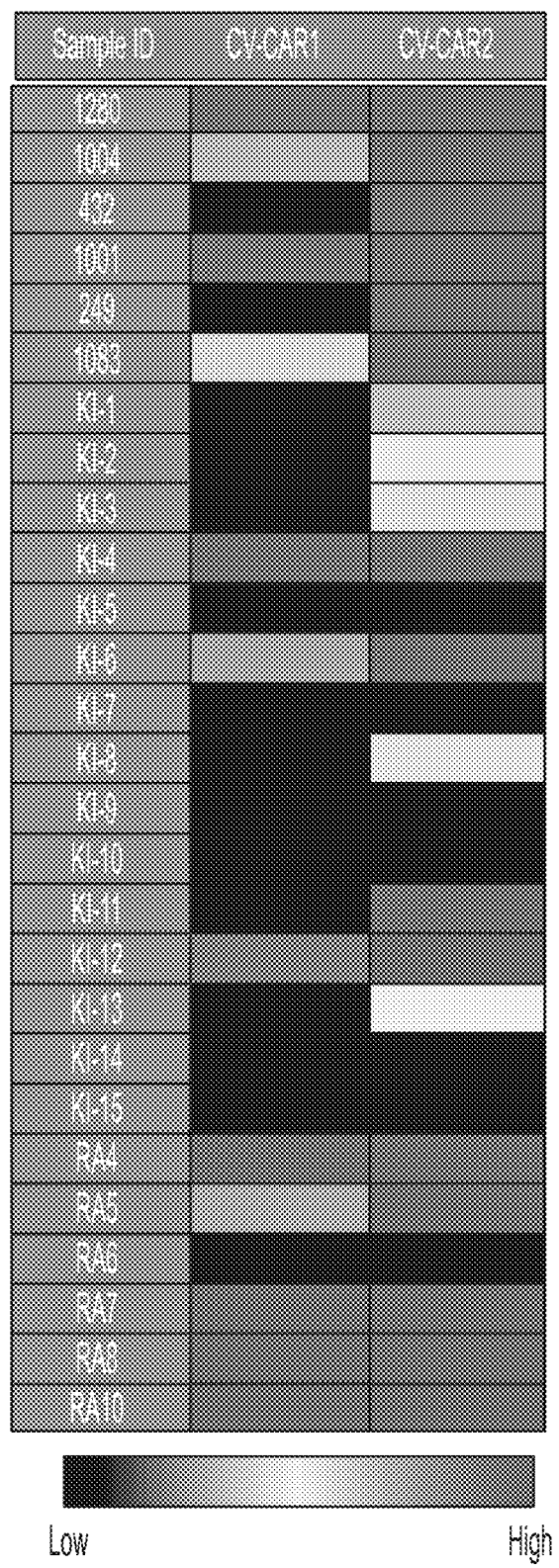

The amount of CV present in the synovial fluid of healthy donors and rheumatoid arthritis (RA) patients was assessed by ELISA as shown in FIG. 14. Jurkat reporter cells expressing one of three different CV-CARs or a control CD19-CAR were incubated with increasing amounts of synovial fluid and responses were measured as an indicator of CV-CAR binding and signal transduction for T cell activation. FIG. 14 shows that Jurkat cells (immortalized, human T lymphocytes) expressing CV-CAR1 (BVCA1) and CV-CAR2 (SBT01G), but not CV-CARS (C03) or CD19-CAR, showed an increase in response to synovial fluid (SF). FIG. 14 also shows that CV-CAR2 (SBT01G) T cells were activated by SF samples from more RA patients than CV-CAR1 (BVCA1) T cells.

Figure 15:
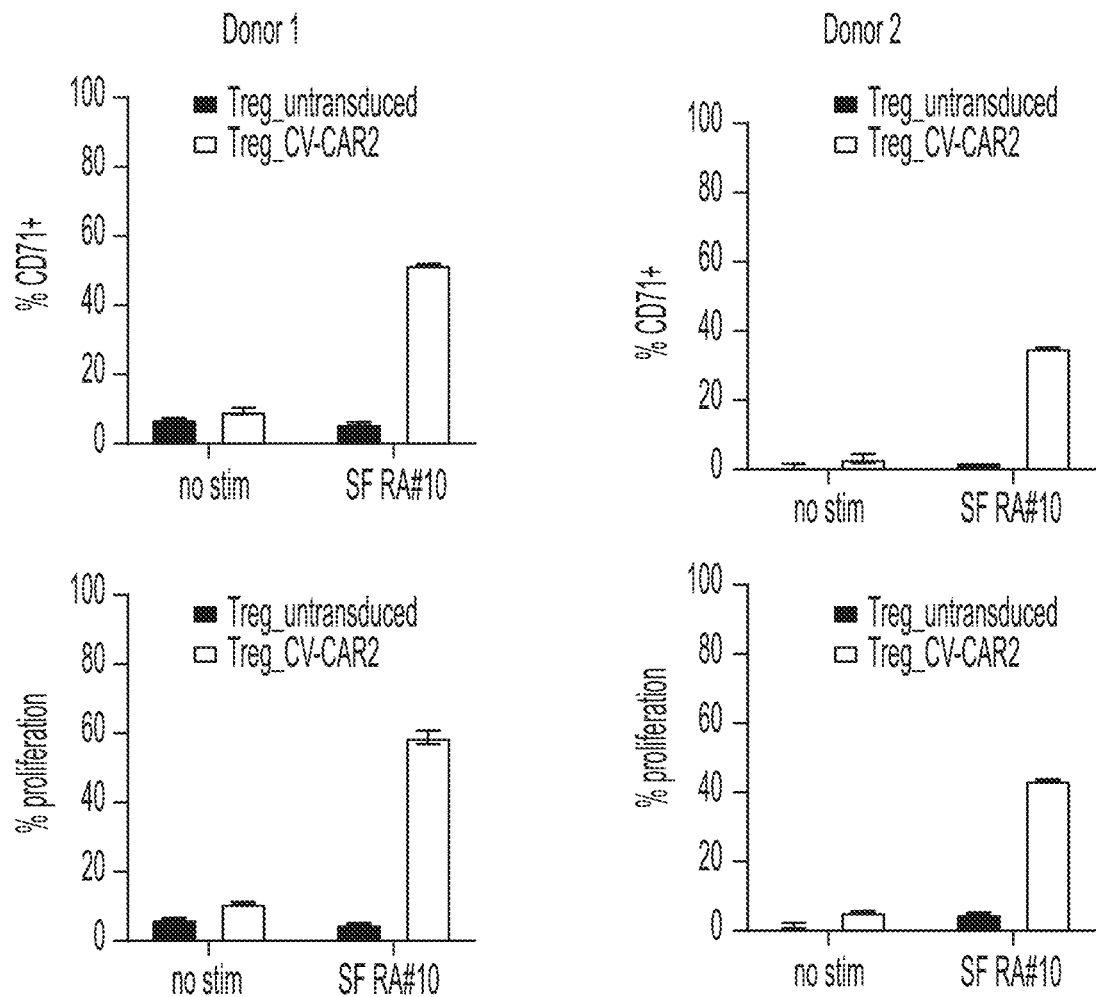
FIG. 15: CV-CAR Treg cells (SBT01G) but not untransduced Treg cells from two donors are specifically activated by synovial fluid from RA patients.

In order to demonstrate that Tregs expressing CV-CARs are activated by citrullinated antigen in the synovial fluid of RA patients, untransduced and CV-CAR2 Tregs were incubated with RA synovial fluid or vehicle and levels of proliferation and CD71 expression were measured. FIG. 15 shows that CV-CAR2 Treg cells from two donors were activated in a RA synovial fluid-specific manner.

Taken together, these results establish that CV-CAR Treg cells are able to bind to a citrullinated antigen, which is present in RA synovial fluid, resulting in activation necessary for suppressive functions.

Example 6: Assessment of CV-Induced Suppression of Teff Cells by CV-CAR Tregs

Treg suppression assay—Treg cells expressing CV-CARs were prepared as described above from fresh human leukopaks in a 96-well U-bottom plate. Tregs were incubated with CV as antigenic stimulus or with a vehicle control. Tregs were co-cultured with either CD3/CD28-activated or CD19-

CAR-specific Teff cells to assess Treg suppression of target cells. Teff cells were co-cultured at the following Treg:Teff ratios: (CD3/CD28-activation) 1:4=0.25, 1:2=0.5, 1:1=1, 2:1=2 and 4:1=4, or (CD19-specific) 1:4, 1:2, 1:1, 2:1 and 4:1.

Results

Figure 16A:
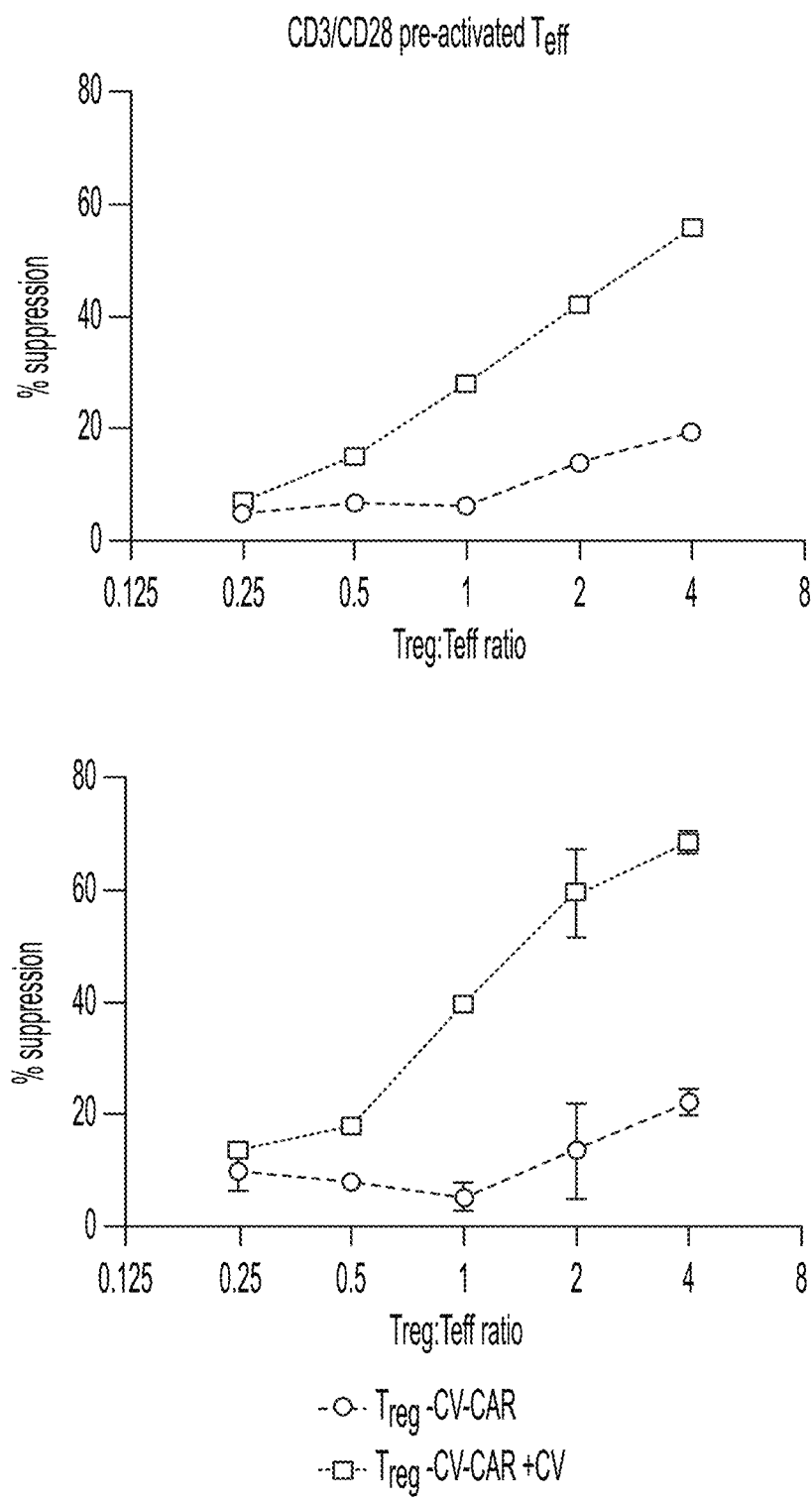
FIG. 16A-16B: Assessment of the suppressive function of CV-CAR Treg cells.
Figure 16B:
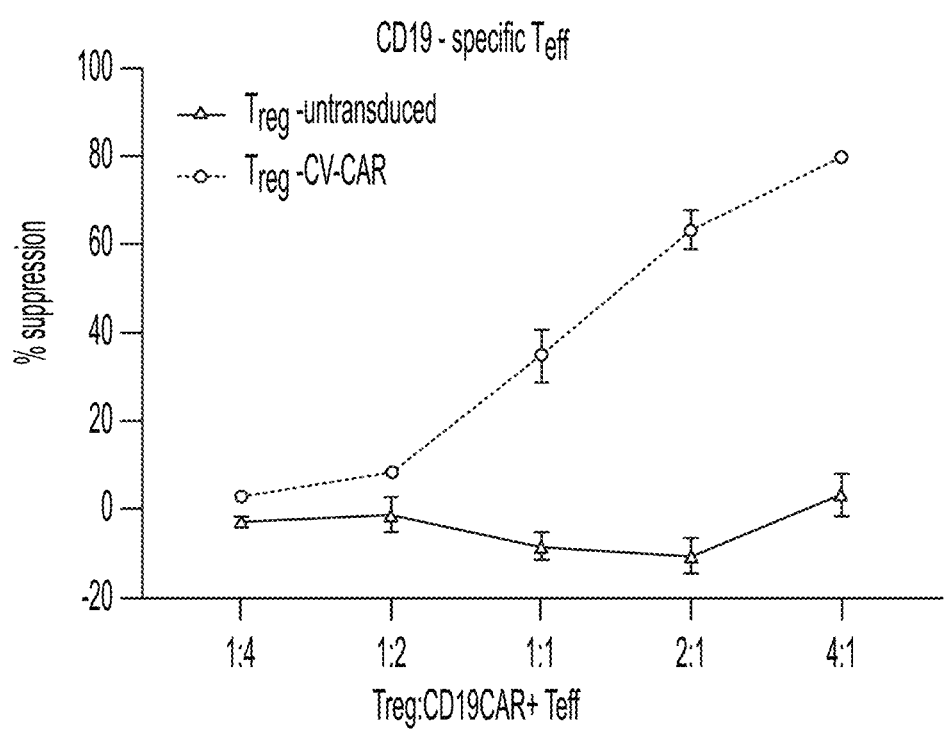

FIG. 16A shows that CV-CAR Tregs stimulated with CV were able to suppress proliferation of CD3/CD28 activated Teff cells at a low Treg:Teff ratio. FIG. 16B shows that CV-CAR Tregs stimulated with CV were also able to suppress proliferation of CD19-CAR Teff cells at a low Treg:Teff ratio.

Example 7: Analysis of CV-CAR Tregs in a Rodent Model of CV-Associated Pulmonary Inflammation In human rheumatoid arthritis (RA) patients, consistently high concentrations of citrullinated vimentin (CV) in synovial fluid identify CV as a relevant biomarker for human RA. However, current mouse models of RA display inconsistent CV levels, which complicates the in vivo analysis of CV-CAR Tregs. To induce CV production and release into the extracellular matrix, a mouse model of LPS-induced lung inflammation was developed. The model is characterized by an acute inflammatory response including pulmonary neutrophilia and increased secretion of the pro-inflammatory cytokines interleukin-6 (IL-6), interleukin-1 beta (IL-1b) and tumor-necrosis factor-alpha (TNF-alpha), as well as an accumulation of CV in lung tissue within days after intranasal LPS challenge. Chimeric antigen receptors (CAR) specific to CV have been shown to react to the accumulated CV protein in lung tissue, which results in survival, proliferation and increases in suppressive activity in an antigen-specific manner of the respective CV-CAR Treg cells.

Methods

Six-to-eight week old immunocompromised NCG mice were obtained from Charles River Laboratories. Mice were randomized by body weight and divided into groups of 5-10 animals. Mice were subjected to intranasal (IN) treatment with LPS (5 mg/kg) on days 0, 1, 6, and 12 to induce pulmonary inflammation, and release and accumulation of citrullinated vimentin (CV) in the affected tissues. On day 0, CV-CAR Treg cells were harvested from actively growing cultures, the stimulation beads were removed magnetically, and the Tregs were subsequently labeled with Cell Trace Violet (CTV) (Invitrogen). About 4 hours after the initial LPS challenge, the CTV-labeled Tregs were adjusted to $25 \times 10^6$ cells/mL in 0.9% sterile saline solution (NaCl) and a 200 µl dose was injected intravenously (IV) such that each mouse received a total of $5 \times 10^6$ cells. Following CV-CAR Treg or control CD19-CAR Treg adoptive cell transfer, all mice received intraperitoneal (IP) injections of IL-2 (160,000 IU) on days 1, 2, 5, 6, 7, 8, 9, and 12. Mice were monitored daily for any clinical signs of distress, and body weight was measured twice per week. Mice were euthanized on day 13, and the spleen and lungs were harvested and processed into single cell suspensions for flow cytometric analysis of the human CV-CAR and CD19-CAR Tregs.

Results

Figure 17:
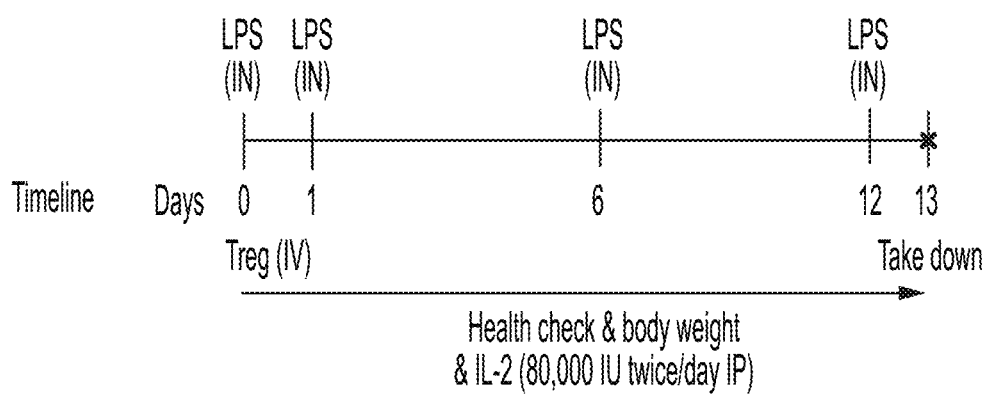
FIG. 17: A timeline of human CV-CAR Treg cell activation in vivo in a lipopolysaccharide (LPS)-induced, murine model of pulmonary inflammation is shown. In brief, human CV-CAR Treg cells were administered intravenously (IV) on Day 0, human IL-2 was administered intraperitoneally (IP) twice daily, and LPS was administered intranasally (IN) on Days 0, 1, 6 and 12. On Day 13, mice were sacrificed and organs were harvested to facilitate analysis of Treg cells.

FIG. 17 shows an exemplary timeline for inducing CV-associated, pulmonary inflammation in mice and the activation of CV-CAR Treg cells in vivo.

Results

Figure 18A:
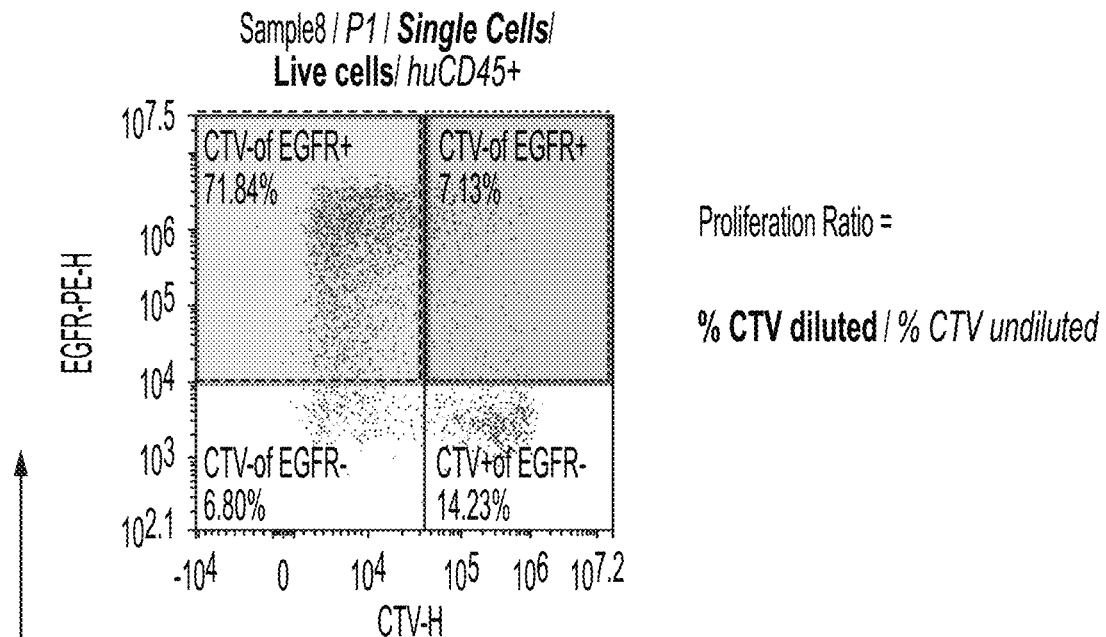
FIG. 18A-18B: Flow cytometry dot plots comparing epidermal growth factor (EGFR) expression by human CV-CAR Treg cells versus of levels of Cell Trace Violet (CIV) are shown.
Figure 18B:
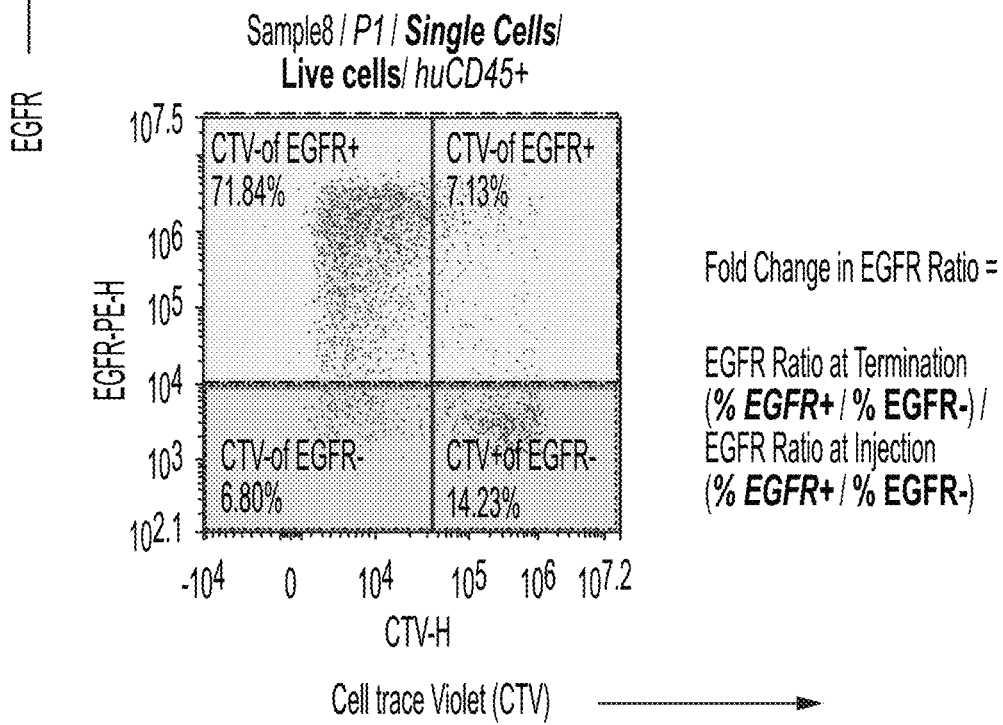

FIG. 18A shows how a proliferation ratio was calculated from flow cytometry data, while FIG. 18B show how a fold change in EGFR ratio (CAR marker) was calculated from the same data.

Figure 19A:
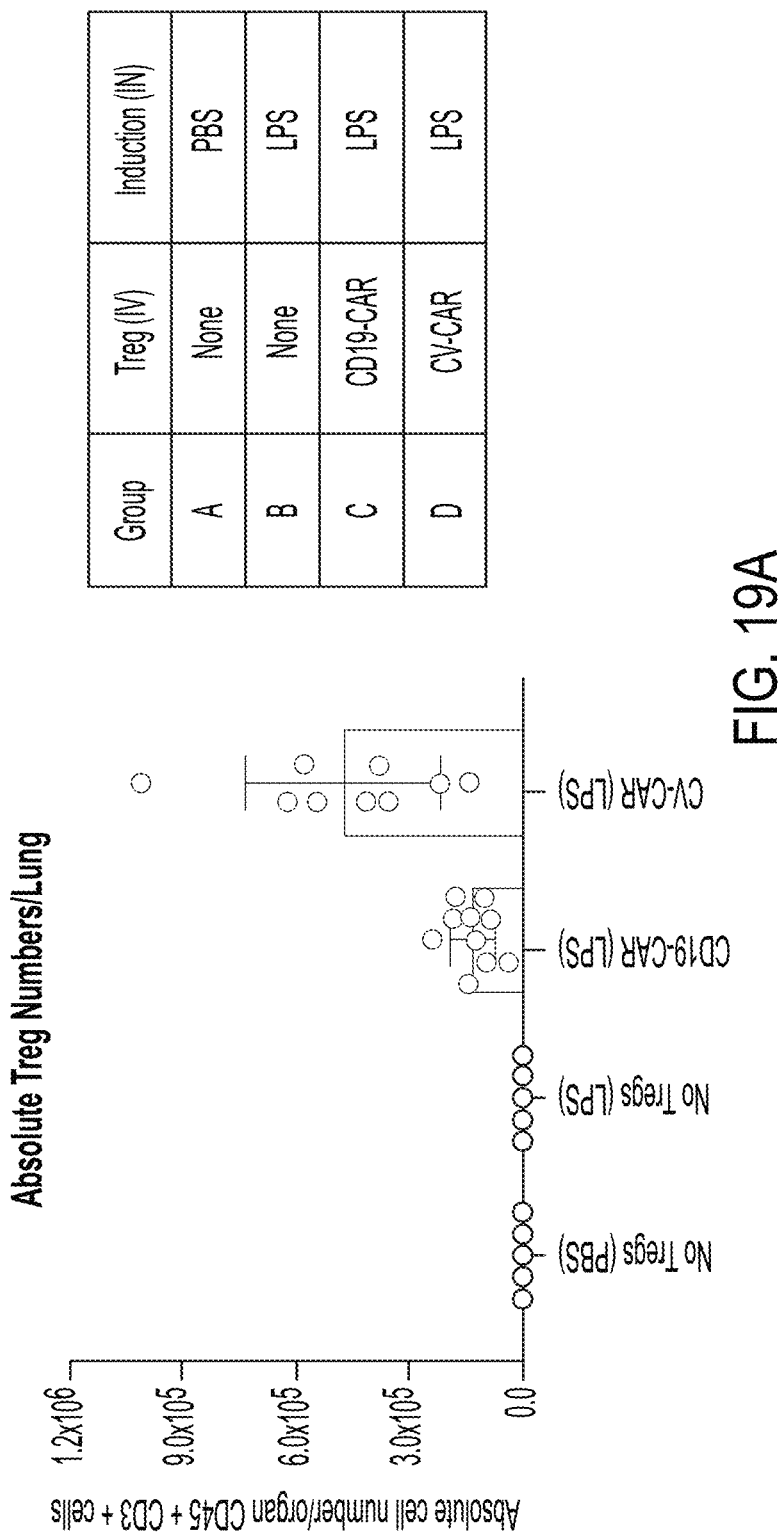
FIG. 19A-19B: CV-CAR Tregs proliferate in a LPS-induced, murine model of pulmonary inflammation but not in control recipients of PBS.
Figure 19B:
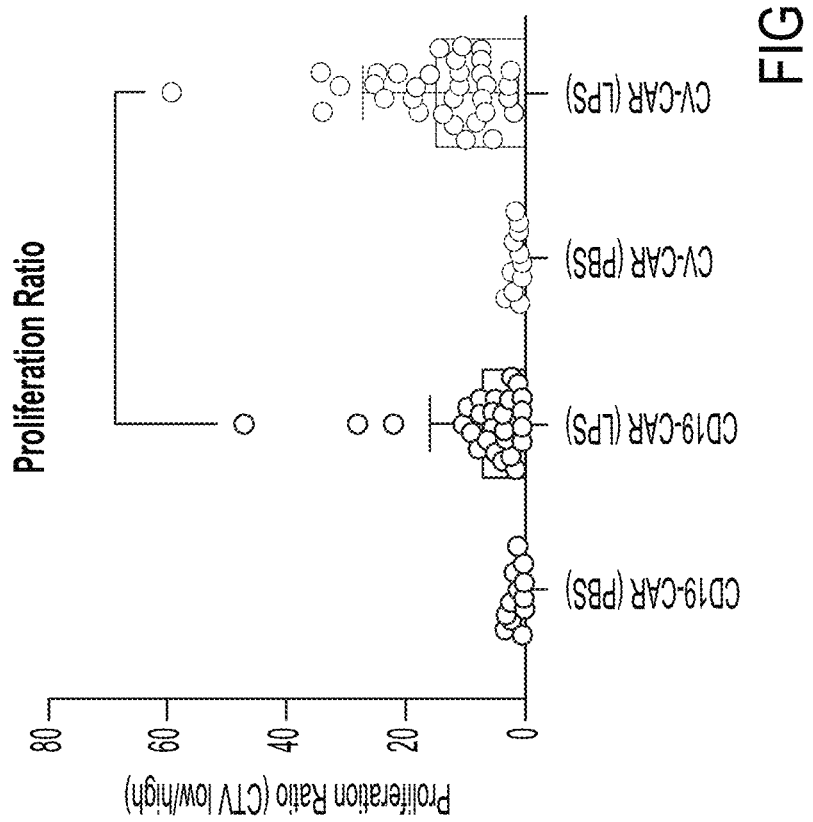

FIG. 19A shows that the absolute number of CV-CAR Tregs were significantly enriched in lung tissue from mice with LPS-induced pulmonary inflammation. FIG. 19B shows that the proliferation ratio of CV-CAR Tregs was significantly increased in lung tissue from mice with LPS-induced pulmonary inflammation. These results demonstrate that CV-CAR Tregs have improved capacity compared to control Tregs to hone to and proliferate in inflamed lung tissues characterized by accumulation of citrullinated vimentin. As such, this murine pulmonary inflammation model permits the testing of human CV-CAR Tregs in vivo.

EXEMPLARY EMBODIMENTS

1. A chimeric antigen receptor (CAR) comprising an antigen-binding domain, a hinge domain, a transmembrane domain, one or more co-stimulatory domains, and an intracellular signaling domain, wherein the antigen binding domain specifically binds to a citrullinated polypeptide, optionally wherein the antigen-binding domain specifically binds to three or more different citrullinated proteins or citrullinated fragments thereof.

2. The CAR of Embodiment 1, wherein the antigen binding domain binds to a plurality of different citrullinated proteins or citrullinated fragments thereof.

3. The CAR of Embodiment 1, wherein the antigen binding domain binds to one or more of: (i) citrullinated vimentin, (ii) citrullinated filaggrin, (iii) citrullinated fibrinogen and (iv) citrullinated peptides fragments of these, e.g., of at least any of 10, 12, 14 or 16 amino acids.

4. The CAR of Embodiment 1, wherein the antigen-binding domain binds to at least two of (i) citrullinated vimentin, (ii) citrullinated filaggrin, and (iii) citrullinated fibrinogen, or citrullinated peptides fragments thereof.

5. The CAR of Embodiment 1, wherein the antigen-binding domain binds to all three of (i) citrullinated vimentin, (ii) citrullinated filaggrin, and (iii) citrullinated fibrinogen, or citrullinated peptides fragments thereof.

6. The CAR of Embodiment 5, that binds further binds citrullinated tenascin C.

7. The CAR of Embodiment 1, wherein the antigen binding domain comprises a VH domain and a VL domain, wherein:
(i) the VH domain comprises a VH-CDR1 comprising the amino acid sequence of SEQ ID NO:32, a VH-CDR2 comprising the amino acid sequence of SEQ ID NO:34, and a VH-CDR3 comprising the amino acid sequence of SEQ ID NO:36, and
(ii) the VL domain of the target-binding domain comprises a VL-CDR1 comprising the amino acid sequence of SEQ ID NO:39, a VL-CDR2 comprising the amino acid sequence of SEQ ID NO:41, and a VL-CDR3 comprising the amino acid sequence of SEQ ID NO:43.

8. The CAR of Embodiment 1, wherein the intracellular signaling domain is derived from CD3zeta.

9. The CAR of Embodiment 1, wherein the at least one co-stimulatory domain is derived from a member of the group consisting of: FceR1g, Fcg, CD28, 4-1BB, CTLA-4, CTLA-4/CD-28 hybrid, DAP10, CD27, and 2B4, optionally wherein the at least one co-stimulatory domain comprises a CD28 and/or a 4-1BB co-stimulatory domain.

10. The CAR of Embodiment 1, wherein the antigen binding domain comprises an antibody, antibody fragment, a camelid nanobody, a heavy chain only antibody or an aptamer.

11. The CAR of any one of Embodiments 1 to 10, wherein the transmembrane domain is a CD8 transmembrane domain or a CD28 transmembrane; and the hinge domain is a CD8 hinge domain or a CD28 hinge domain; and/or further comprising a signal peptide, optionally wherein the signal peptide is a CD8 signal peptide or a GM-CSF signal peptide.

12. The CAR of Embodiment 11, wherein the antigen-specific binding domain comprises a single chain fragment.

13. The CAR of Embodiment 12, wherein the single chain fragment comprises a single chain variable fragment (scFv), optionally wherein the scFv fragment comprises:
(a) a VH domain comprising the amino acid sequence of SEQ ID NO:1; and
(b) a VL domain comprising the amino acid sequence of SEQ ID NO:4.

14. The CAR of Embodiment 13, wherein the scFv fragment comprises:
(a) a VH selected from:

```
(1) SBT01 VH (M)
                                          (SEQ ID NO: 1)
HLHLQESGPGLVKPSETLSLTCTVSGGSINDTTYYWGWIRQPPGKGLEW
IGSIYYRGNTHYNSSLRSRVTMSVDTSKNRFSLKVTSVTAADTAVYYCA
RLDPFDYWGRGTLVTVSS;
or (2) SBT01 VH (G)
                                          (SEQ ID NO: 2)
QLQLQESGPGLVKPSETLSLTCTVSGGSISSSSYYWGWIRQPPGKGLEW
IGSIYYSGSTYYNPSLKSRVTISVDTSKNQFSLKLSSVTAADTAVYYCA
RLDPFDYWGRGTLVTVSS;
and (b) a VL selected from:
(1) SBT01 VL (M)
                                          (SEQ ID NO: 3)
SYVLTQPPSVSLAPGETATSTCGGDDIENQNVNWYQQKSGQAPMLLFFD
TRRPSGIPERFSGSRSEDTANLTITRVEAGDDADYFCQVYDRKTDHQVF
GPGTTVTVL
or (2) SBT01 VL (G)
                                          (SEQ ID NO: 4)
SYVLTQPPSVSVAPGKTARITCGGNNIGSKSVHWYQQKPGQAPVLVIYY
DSDRPSGIPERFSGSNSGNTATLTISRVEAGDEADYYCQVWDSSSDHQV
FGTGTKVTVL.
```

15. The CAR of Embodiment 14, wherein the VH-VL fragments are joined by a linker selected from the group consisting of (i) GGGSx3 (SEQ ID NO:20), (ii) Whitlow 218 (SEQ ID NO:21), and (iii) AB Pur (SEQ ID NO:22).

16. The CAR of Embodiment 13, wherein the scFv comprises the amino acid sequence of:

```
(a) SBT01G-VHVL-GGGSx3 Linker-pSB_0149
                                          (SEQ ID NO: 5)
HLHLQESGPGLVKPSETLSLTCTVSGGSINDTTYYWGWIRQPPGKGLEW

IGSIYYRGNTHYNSSLRSRVTMSVDTSKNRFSLKVTSVTAADTAVYYCA

RLDPFDYWGRGTLVTVSSGGGGSGGGGSGGGGSSYVLTQPPSVSVAPGK

TARITCGGNNIGSKSVHWYQQKPGQAPVLVIYYDSDRPSGIPERFSGSN

SGNTATLTISRVEAGDEADYYCQVWDSSSDHQVFGTGTKVTVLR (GGGSx3 linker underlined);
or (b) SBT01G-VHVL-Whitlow 218 Linker-pSB_0158
                                          (SEQ ID NO: 6)
HLHLQESGPGLVKPSETLSLTCTVSGGSINDTTYYWGWIRQPPGKGLEW

IGSIYYRGNTHYNSSLRSRVTMSVDTSKNRFSLKVTSVTAADTAVYYCA

RLDPFDYWGRGTLVTVSSGSTSGSGKPGSGEGSTKGSYVLTQPPSVSVA

PGKTARITCGGNNIGSKSVHWYQQKPGQAPVLVIYYDSDRPSGIPERFS

GSNSGNTATLTISRVEAGDEADYYCQVWDSSSDHQVFGTGTKVTVLR (Whitlow 218 Linker underlined);
or (c) SBT01G-VHVL-AB pur Linker-pSB_0159
                                          (SEQ ID NO: 7)
HLHLQESGPGLVKPSETLSLTCTVSGGSINDTTYYWGWIRQPPGKGLEW

IGSIYYRGNTHYNSSLRSRVTMSVDTSKNRFSLKVTSVTAADTAVYYCA

RLDPFDYWGRGTLVTVSSASSGGSTSGSGKPGSGEGSSGSARSYVLTQP

PSVSVAPGKTARITCGGNNIGSKSVHWYQQKPGQAPVLVIYYDSDRPSG

IPERFSGSNSGNTATLTISRVEAGDEADYYCQVWDSSSDHQVFGTGTKV

TVLR  (AB pur Linker underlined).
```

17. The CAR of any of Embodiments 1-16, wherein the co-stimulatory domain comprises a CD28, 41BB, OX40, OX40, CD40L, MyD88, CD40, CD27, ICOS, or RANK/TRANCE-R co-stimulatory domain.

18. A nucleic acid encoding the CAR of any of Embodiments 1-17.

19. The nucleic acid of Embodiment 18, comprising DNA or RNA.

20. The nucleic acid of Embodiment 18, wherein:

the VH is encoded by the nucleic acid sequence comprising:

```
CACCTGCACTTGCAGGAGTCGGGCCCAGGACTTGTGAAGCCTTCGGAGA

CCCTGTCCCTCACCTGCACTGTCTCTGGTGGCTCCATCAACGATACCAC

TTACTACTGGGGCTGGATTCGCCAGCCCCCGGGAAGGGACTGGAGTGG

ATTGGGAGTATCTATTACCGGGGGAACACCCACTACAATTCGTCCCTGA

GGAGTCGCGTCACCATGTCTGTCGACACTTCCAAGAACCGATTCTCCCT

GAAGGTCACTTCTGTGACTGCCGCAGACACGGCTGTCTATTACTGTGCG

AGACTCGACCCATTTGACTACTGGGGCCGTGGCACCCTGGTCACTGTCT

CGAGC,
or

CAGCTGCAGCTGCAGGAGTCGGGCCCAGGACTGGTGAAGCCTTCGGAGA

CCCTGTCCCTCACCTGCACTGTCTCTGGTGGCTCCATCAGCAGTAGTAG

TTACTACTGGGGCTGGATCCGCCAGCCCCCAGGGAAGGGGCTGGAGTGG

ATTGGGAGTATCTATTATAGTGGGAGCACCTACTACAACCCGTCCCTCA

AGAGTCGAGTCACCATATCCGTAGACACGTCCAAGAACCAGTTCTCCCT

GAAGCTGAGCTCTGTGACCGCCGCAGACACGGCTGTGTATTACTGTGCG

AGACTCGACCCATTTGACTACTGGGGCCGTGGCACCCTGGTCACTGTCT

CGAGC;
``` and
the VL is encoded by a nucleic acid sequence comprising;

```
TCCTATGTCCTGACTCAGCCACCCTCAGTGTCGCT
GGCCCCGGGAGAGACGGCCACAATTACTTGTGGTG
GAGACGACATTGAAAATCAAAATGTCAACTGGTAT
CAGCAGAAGTCAGGTCAGGCCCCTATGCTGCTCAT
CTTCTTTGATACCAGACGGCCCTCAGGGATCCCGG
AGCGATTCTCTGGCTCCAGGTCTGAGGACACGGCC
AACCTGACCATCACCAGGGTCGAGGCCGGGGATGA
CGCCGACTATTTCTGTCAGGTGTATGATAGGAAGA
CTGATCACCAAGTCTTCGGACCTGGGACCACGGTC
ACCGTCCTA,
or
TCCTATGTGCTGACTCAGCCACCCTCAGTGTCAGT
GGCCCCAGGAAAGACGGCCAGGATTACCTGTGGGG
GAAACAACATTGGAAGTAAAAGTGTGCACTGGTAC
CAGCAGAAGCCAGGCCAGGCCCCTGTGCTGGTCAT
CTATTATGATAGCGACCGGCCCTCAGGGATCCCTG
AGCGATTCTCTGGCTCCAACTCTGGGAACACGGCC
ACCCTGACCATCAGCAGGGTCGAAGCCGGGGATGA
GGCCGACTATTACTGTCAGGTGTGGGACAGTAGTA
GTGATCACCAAGTCTTCGGAACTGGGACCAAGGTC
ACCGTCCTA.
```

21. The nucleic acid of Embodiment 20, wherein the VH and VL fragments are joined by linker and comprise the nucleic acid sequence of (i) SEQ ID NO:12, (ii) SEQ ID NO:13, or (iii) SEQ ID NO:14.

22. An expression vector comprising an expression control sequence operatively linked to the nucleic acid sequence of any of Embodiments 16-21.

23. The expression vector of Embodiment 22, wherein the expression control sequence comprises a regulatory region, wherein the regulatory region is selected from the group consisting of: promoter sequences, enhancer sequences, response elements, protein recognition sites, inducible elements, protein binding sequences, 5' and 3' non-translated regions, transcriptional start sites, termination sequences, polyadenylation sequences, nuclear localization, signals, and introns.

24. The expression vector of Embodiment 23, wherein the vector is an adenoviral vector, a lentiviral vector or a plasmid.

25. A host cell comprising the expression vector of Embodiment 22, 23 or 24.

26. A modified T cell that has been modified to express the chimeric antigen receptor (CAR) of any of Embodiments 1-17.

27. The modified cell of Embodiment 26, wherein the cell is a mammalian cell.

28. The modified T cell of Embodiment 27, wherein the T cell is a Treg cell.

29. The modified T cell of Embodiment 28, wherein the T-cell is a human T cell.

30. The modified T cell of Embodiment 29, wherein the T cell is a primary T cell.

31. The modified T cell of Embodiment 30, wherein the T cell is CD4+, CD25+ and CD127lo.

32. A pharmaceutical composition comprising a plurality of the modified T cell of any of Embodiments 26 to 31, and a pharmaceutically acceptable carrier.

33. A method of treating a subject suffering from rheumatoid arthritis, comprising administering to the subject an effective amount of a pharmaceutical composition of Embodiment 32.

34. The method of Embodiment 33, wherein the subject is a human.

35. The method of Embodiment 33 or 34, wherein the pharmaceutical composition is administered into a synovium of the subject.

36. The method of Embodiment 33 or 34, wherein the pharmaceutical composition is administered intravenously.

37A. The method of Embodiment 33, wherein administering comprises:
(a) isolating cells from a biological sample obtained from the subject;
(b) enriching the T cells for T regulatory cells (Treg);
(c) transfecting the enriched Treg cells with an expression vector comprising an expression control sequence operatively linked to a nucleotide sequence encoding a chimeric antigen receptor (CAR) comprising an antigen binding domain that binds to a citrullinated polypeptide;
(d) expanding the transfected Treg cells; and (e) administering the expanded Treg cells to the subject.

37B. A method of treating a subject suffering from rheumatoid arthritis, the method comprising;
(a) isolating T cells from a biological sample obtained from the subject;
(b) enriching the T cells for T regulatory cells (Treg);
(c) transfecting the enriched Treg cells with an expression vector encoding the CAR of any one of Embodiments 1-17;
(d) expanding the transfected Treg cells; and
(e) administering the expanded Treg cells to the subject.

38. The method of Embodiment 37, wherein the expansion comprises using anti-CD3/CD28 coated beads.

39. The method of Embodiment 37, wherein the expansion is does not use anti-CD3/CD28 coasted beads.

40. The method of Embodiment 37, wherein the transfection occurs by use of a viral vector, electroporation, heat shock, bacteriophage, sonication, or calcium phosphate.

41. The method of any of Embodiments 37 to 40 further comprising administering one or more anti-inflammatory and/or therapeutic agents to the subject.

42. The method of Embodiment 41, wherein the anti-inflammatory agent comprises an antibody that inhibits a pro-inflammatory cytokine.

43. The method of Embodiment 42, wherein the anti-inflammatory agent is an anti-TNF-antibody, an anti-IL-6 antibody, or a combination thereof.

44. A kit comprising a container containing the pharmaceutical composition of Embodiment 32, communicating through a fluidic conduit with a drip chamber, wherein the drip chamber communicates through a fluidic conduit with an intravenous needle.

45. The kit of Embodiment 44, wherein the container comprises a bag.

46. The kit of Embodiment 44, wherein the fluidic conduit between the container and the needle comprises one or more Y-sites and a roller clamp.

It should be understood that the description and the drawings are not intended to limit the invention to the particular form disclosed, but to the contrary, the intention is to cover all modifications, equivalents, and alternatives falling within the spirit and scope of the present invention as defined by the appended claims. Further modifications and alternative embodiments of various aspects of the invention will be apparent to those skilled in the art in view of this description. Accordingly, this description and the drawings are to be construed as illustrative only and are for the purpose of teaching those skilled in the art the general manner of carrying out the invention. It is to be understood that the forms of the invention shown and described herein are to be taken as examples of embodiments. Elements and materials may be substituted for those illustrated and described herein, parts and processes may be reversed or omitted, and certain features of the invention may be utilized independently, all as would be apparent to one skilled in the art after having the benefit of this description of the invention. Changes may be made in the elements described herein without departing from the spirit and scope of the invention as described in the following claims. Headings used herein are for organizational purposes only and are not meant to be used to limit the scope of the description.

All publications, patents, and patent applications mentioned in this specification are herein incorporated by reference to the same extent as if each individual publication, patent, or patent application was specifically and individually indicated to be incorporated by reference.

We claim:

1. A chimeric antigen receptor (CAR) comprising an antigen-binding domain, a hinge domain, a transmembrane domain, one or more co-stimulatory domains, and an intracellular signaling domain, wherein the antigen binding domain specifically binds to three or more different citrullinated proteins or citrullinated fragments thereof, and comprises complementarity-determining regions (CDRs) from VH and VL domains of SEQ ID NO:1 and SEQ ID NO:4.

2. The CAR of claim 1, wherein the antigen-binding domain binds to all three of (i) citrullinated vimentin, (ii) citrullinated filaggrin, and (iii) citrullinated fibrinogen, or citrullinated peptides fragments thereof.

3. The CAR of claim 1, wherein the antigen binding domain comprises a VH domain and a VL domain, wherein:
   (i) the VH domain comprises a VH-CDR1 comprising the amino acid sequence of SEQ ID NO:32, a VH-CDR2 comprising the amino acid sequence of SEQ ID NO:34, and a VH-CDR3 comprising the amino acid sequence of SEQ ID NO:36, and
   (ii) the VL domain of the target-binding domain comprises a VL-CDR1 comprising the amino acid sequence of SEQ ID NO:39, a VL-CDR2 comprising the amino acid sequence of SEQ ID NO:41, and a VL-CDR3 comprising the amino acid sequence of SEQ ID NO:43.

4. The CAR of claim 1, wherein the intracellular signaling domain is derived from CD3-zeta.

5. The CAR of claim 1, wherein the one or more co-stimulatory domains comprises a domain of the group consisting of FceR1g, Fcg, CD28, CD134 (OX40), CD137 (4-1BB), CTLA-4, CTLA-4/CD-28 hybrid, DAP10, CD27, 2B4, and combinations thereof.

6. The CAR of claim 1, wherein the antigen binding domain comprises an antibody, an antibody fragment, a camelid nanobody, a heavy chain only antibody or an aptamer.

7. The CAR of claim 1, wherein the transmembrane domain is a CD8 transmembrane domain or a CD28 transmembrane domain.

8. The CAR of claim 1, wherein the hinge domain is a CD8 hinge domain or a CD28 hinge domain.

9. The CAR of claim 1, wherein the antigen-specific binding domain comprises a single chain fragment.

10. The CAR of claim 9, wherein the single chain fragment comprises a single chain variable fragment (scFv).

11. The CAR of claim 10, wherein the scFv fragment comprises:
    (a) a VH domain comprising the amino acid sequence having at least 95% identity to SEQ ID NO:1; and
    (b) a VL domain comprising the amino acid sequence having at least 95% identity to SEQ ID NO:4.

12. The CAR of claim 10, wherein the scFv fragment comprises:
    (a) a VH domain comprising the amino acid sequence of SEQ ID NO:1; and
    (b) a VL domain comprising the amino acid sequence of SEQ ID NO:4.

13. The CAR of claim 12, wherein the VH domain and the VL domain are joined by a linker comprising the amino acid sequence of SEQ ID NO:20, SEQ ID NO:21, or SEQ ID NO:22.

14. The CAR of claim 13, wherein the scFv comprises the amino acid sequence of SEQ ID NO:5.

15. A nucleic acid encoding the CAR of claim 1.

16. The nucleic acid of claim 15, wherein the VH domain is encoded by the nucleic acid sequence comprising SEQ ID NO:8; and the VL domain is encoded by the nucleic acid sequence comprising SEQ ID NO:11.

17. The nucleic acid of claim 16, wherein the VH and VL fragments are joined by a linker and comprise the nucleic acid sequence of SEQ ID NO:12, or (ii) SEQ ID NO:13, or (iii) SEQ ID NO:14.

18. An expression vector comprising an expression control sequence operatively linked to the nucleic acid sequence of claim 17.

19. A modified T cell that has been modified to express the chimeric antigen receptor (CAR) of claim 1.

20. The modified T cell of claim 19, wherein the T cell is a Treg cell.

21. The modified T cell of claim 20, wherein the T cell is a human T cell.

22. The modified T cell of claim 21, wherein the T cell is a primary T-cell.

23. The modified T cell of claim 22, wherein the T cell is CD4+, CD25+ and CD127lo.

24. A pharmaceutical composition comprising a plurality of the modified T cells of claim 23, and a pharmaceutically acceptable carrier.

25. A method of treating a human subject suffering from rheumatoid arthritis, comprising administering to the subject an effective amount of the pharmaceutical composition of claim 24.

26. The method of claim 25, wherein the pharmaceutical composition is administered into a synovium of the subject.

27. The method of claim 25, wherein the pharmaceutical composition is administered intravenously.

28. A method of treating a human subject suffering from rheumatoid arthritis, the method comprising:
   (a) isolating T cells from a biological sample obtained from the subject;
   (b) enriching the T cells for T regulatory cells (Treg);
   (c) transfecting the enriched Treg cells with an expression vector encoding the CAR of claim 1;
   (d) expanding the transfected Treg cells; and
   (e) administering the expanded Treg cells to the subject.

29. The method of claim 28, wherein the expansion comprises using anti-CD3/CD28 coated beads.

30. The method of claim 28, wherein the expansion does not comprise using anti-CD3/CD28 coasted beads.

* * * * *

SEQUENCE LISTING

```
Sequence total quantity: 48
SEQ ID NO: 1            moltype = AA   length = 116
FEATURE                 Location/Qualifiers
source                  1..116
                        mol_type = protein
                        organism = Homo sapiens
SEQUENCE: 1
HLHLQESGPG LVKPSETLSL TCTVSGGSIN DTTYYWGWIR QPPGKGLEWI GSIYYRGNTH   60
YNSSLRSRVT MSVDTSKNRF SLKVTSVTAA DTAVYYCARL DPFDYWGRGT LVTVSS      116

SEQ ID NO: 2            moltype = AA   length = 116
FEATURE                 Location/Qualifiers
source                  1..116
                        mol_type = protein
                        organism = Homo sapiens
SEQUENCE: 2
QLQLQESGPG LVKPSETLSL TCTVSGGSIS SSSYYWGWIR QPPGKGLEWI GSIYYSGSTY   60
YNPSLKSRVT ISVDTSKNQF SLKLSSVTAA DTAVYYCARL DPFDYWGRGT LVTVSS      116

SEQ ID NO: 3            moltype = AA   length = 108
FEATURE                 Location/Qualifiers
source                  1..108
                        mol_type = protein
                        organism = Homo sapiens
SEQUENCE: 3
SYVLTQPPSV SLAPGETATI TCGGDDIENQ NVNWYQQKSG QAPMLLIFFD TRRPSGIPER   60
FSGSRSEDTA NLTITRVEAG DDADYFCQVY DRKTDHQVFG PGTTVTVL               108

SEQ ID NO: 4            moltype = AA   length = 108
FEATURE                 Location/Qualifiers
source                  1..108
                        mol_type = protein
                        organism = Homo sapiens
SEQUENCE: 4
SYVLTQPPSV SVAPGKTARI TCGGNNIGSK SVHWYQQKPG QAPVLVIYYD SDRPSGIPER   60
FSGSNSGNTA TLTISRVEAG DEADYYCQVW DSSSDHQVFG TGTKVTVL               108

SEQ ID NO: 5            moltype = AA   length = 240
FEATURE                 Location/Qualifiers
source                  1..240
                        mol_type = protein
                        organism = synthetic construct
SEQUENCE: 5
HLHLQESGPG LVKPSETLSL TCTVSGGSIN DTTYYWGWIR QPPGKGLEWI GSIYYRGNTH   60
YNSSLRSRVT MSVDTSKNRF SLKVTSVTAA DTAVYYCARL DPFDYWGRGT LVTVSSGGGG  120
SGGGGSGGGG SSYVLTQPPS VSVAPGKTAR ITCGGNNIGS KSVHWYQQKP GQAPVLVIYY  180
DSDRPSGIPE RFSGSNSGNT ATLTISRVEA GDEADYYCQV WDSSSDHQVF GTGTKVTVLR  240

SEQ ID NO: 6            moltype = AA   length = 243
FEATURE                 Location/Qualifiers
source                  1..243
                        mol_type = protein
                        organism = synthetic construct
SEQUENCE: 6
HLHLQESGPG LVKPSETLSL TCTVSGGSIN DTTYYWGWIR QPPGKGLEWI GSIYYRGNTH   60
YNSSLRSRVT MSVDTSKNRF SLKVTSVTAA DTAVYYCARL DPFDYWGRGT LVTVSSGSTS  120
GSGKPGSGEG STKGSYVLTQ PPSVSVAPGK TARITCGGNN IGSKSVHWYQ QKPGQAPVLV  180
IYYDSDRPSG IPERFSGSNS GNTATLTISR VEAGDEADYY CQVWDSSSDH QVFGTGTKVT  240
VLR                                                                243
```

```
SEQ ID NO: 7                moltype = AA   length = 249
FEATURE                     Location/Qualifiers
source                      1..249
                            mol_type = protein
                            organism = synthetic construct
SEQUENCE: 7
HLHLQESGPG LVKPSETLSL TCTVSGGSIN DTTYYWGWIR QPPGKGLEWI GSIYYRGNTH   60
YNSSLRSRVT MSVDTSKNRF SLKVTSVTAA DTAVYYCARL DPFDYWGRGT LVTVSSASSG  120
GSTSGSGKPG SGEGSSGSAR SYVLTQPPSV SVAPGKTARI TCGGNNIGSK SVHWYQQKPG  180
QAPVLVIYYD SDRPSGIPER FSGSNSGNTA TLTISRVEAG DEADYYCQVW DSSSDHQVFG  240
TGTKVTVLR                                                          249

SEQ ID NO: 8                moltype = DNA   length = 348
FEATURE                     Location/Qualifiers
source                      1..348
                            mol_type = genomic DNA
                            organism = Homo sapiens
SEQUENCE: 8
cacctgcact tgcaggagtc gggcccagga cttgtgaagc cttcggagac cctgtccctc   60
acctgcactg tctctggtgg ctccatcaac gataccactt actactgggg ctggattcgc  120
cagcccccag ggaagggact ggagtggatt gggagtatct attaccggga aacacccac   180
tacaattcgt ccctgaggag tcgcgtcacc atgtctgtcg acacttccaa gaaccgattc  240
tccctgaagg tcacttctgt gactgccgca gacacggctg tctattactg tgcgagactc  300
gacccatttg actactgggg ccgtggcacc ctggtcactg tctcgagc               348

SEQ ID NO: 9                moltype = DNA   length = 348
FEATURE                     Location/Qualifiers
source                      1..348
                            mol_type = genomic DNA
                            organism = Homo sapiens
SEQUENCE: 9
cagctgcagc tgcaggagtc gggcccagga ctggtgaagc cttcggagac cctgtccctc   60
acctgcactg tctctggtgg ctccatcagc agtagtagtt actactgggg ctggatccgc  120
cagcccccag ggaagggcct ggagtggatt gggagtatct attatagtgg gagcacctac  180
tacaacccgt ccctcaagag tcgagtcacc atatccgtag acacgtccaa gaaccagttc  240
tccctgaagc tgagctctgt gaccgccgca gacacggctg tgtattactg tgcgagactc  300
gacccatttg actactgggg ccgtggcacc ctggtcactg tctcgagc               348

SEQ ID NO: 10               moltype = DNA   length = 324
FEATURE                     Location/Qualifiers
source                      1..324
                            mol_type = genomic DNA
                            organism = Homo sapiens
SEQUENCE: 10
tcctatgtcc tgactcagcc accctcagtg tcgctggccc cgggagagac ggccacaatt   60
acttgtggtg gagacgacat tgaaaatcaa aatgtcaact ggtatcagca gaagtcaggt  120
caggccccta tgctgctcat cttctttgat accagacggc cctcaggat  cccgagcga   180
ttctctggct ccaggtctga ggacacggca aacctgacca tcaccaggt  cgaggccggg  240
gatgacgccg actatttctg tcaggtgtat gataggaaga ctgatcacca agtcttcgga  300
cctgggacca cggtcaccgt ccta                                         324

SEQ ID NO: 11               moltype = DNA   length = 324
FEATURE                     Location/Qualifiers
source                      1..324
                            mol_type = genomic DNA
                            organism = Homo sapiens
SEQUENCE: 11
tcctatgtgc tgactcagcc accctcagtg tcagtggccc caggaaagac ggccaggatt   60
acctgtgggg gaaacaacat tggaagtaaa agtgtgcact ggtaccagca gaagccaggc  120
caggcccctg tgctggtcat ctattatgat agcgaccggc cctcaggat  ccctgagcga  180
ttctctggct ccaactctgg gaacacggcc accctgacca tcagcaggt  cgaagccggg  240
gatgaggccg actattactg tcaggtgtgg acagtagta  gtgatcacca agtcttcgga  300
actgggacca aggtcaccgt ccta                                         324

SEQ ID NO: 12               moltype = DNA   length = 720
FEATURE                     Location/Qualifiers
source                      1..720
                            mol_type = other DNA
                            organism = synthetic construct
SEQUENCE: 12
cacctgcact tgcaggagtc gggcccagga cttgtgaagc cttcggagac cctgtccctc   60
acctgcactg tctctggtgg ctccatcaac gataccactt actactgggg ctggattcgc  120
cagcccccag ggaagggact ggagtggatt gggagtatct attaccggga aacacccac   180
tacaattcgt ccctgaggag tcgcgtcacc atgtctgtcg acacttccaa gaaccgattc  240
tccctgaagg tcacttctgt gactgccgca gacacggctg tctattactg tgcgagactc  300
gacccatttg actactgggg ccgtggcacc ctggtcactg tctcgagcgg tggcggtggc  360
tcgggcggtg gtgggcggg  tggcggcgga tcttcctatg tgctgactca gccaccctca  420
gtgtcagtgg ccccaggaaa gacggccagg attacctgtg gggaaacaa  cattggaagt  480
```

```
aaaagtgtgc actggtacca gcagaagcca ggccaggccc ctgtgctggt catctattat    540
gatagcgacc ggccctcagg gatccctgag cgattctctg ctccaactc tgggaacacg     600
gccaccctga ccatcagcag ggtcgaagcc gggatgagg ccgactatta ctgtcaggtg     660
tgggacagta gtagtgatca ccaagtcttc ggaactggga ccaaggtcac cgtcctacgc    720

SEQ ID NO: 13            moltype = DNA   length = 729
FEATURE                  Location/Qualifiers
source                   1..729
                         mol_type = other DNA
                         organism = synthetic construct
SEQUENCE: 13
cacctgcact tgcaggagtc gggcccagga cttgtgaagc cttcggagac cctgtccctc    60
acctgcactg tctctggtgg ctccatcaac gataccactt actactgggg ctggattcgc    120
cagccccccg ggaagggact ggagtggatt gggagtatct attaccgggg gaacacccac    180
tacaattcgt ccctgaggag tcgcgtcacc atgtctgtcg acacttccaa gaaccgattc    240
tccctgaagg tcacttctgt gactgccgca gacacggctg tctattactg tgcgagactc    300
gacccatttg actactgggg ccgtggcacc ctggtcactg tctcgagcgg aagcacgagt    360
ggttcaggca aaccgggttc cggtgaaggt tcaacaaaag gttcctatgt gctgactcag    420
ccacccctcag tgtcagtggc cccaggaaaa acgccagga ttacctgtgg gggaaacaac    480
attgaagta aaagtgtgca ctggtaccag cagaagccag gccaggcccc tgtgctggtc     540
atctattatg atagcgaccg gccctcaggg atccctgagc gattctctgg ctccaactct    600
gggaacacgg ccaccctgac catcagcagg gtcgaagccg ggatgaggc cgactattac    660
tgtcaggtgt gggacagtag tagtgatcac caagtcttcg gaactgggac caaggtcacc    720
gtcctacgc                                                           729

SEQ ID NO: 14            moltype = DNA   length = 747
FEATURE                  Location/Qualifiers
source                   1..747
                         mol_type = other DNA
                         organism = synthetic construct
SEQUENCE: 14
cacctgcact tgcaggagtc gggcccagga cttgtgaagc cttcggagac cctgtccctc    60
acctgcactg tctctggtgg ctccatcaac gataccactt actactgggg ctggattcgc    120
cagccccccg ggaagggact ggagtggatt gggagtatct attaccgggg gaacacccac    180
tacaattcgt ccctgaggag tcgcgtcacc atgtctgtcg acacttccaa gaaccgattc    240
tccctgaagg tcacttctgt gactgccgca gacacggctg tctattactg tgcgagactc    300
gacccatttg actactgggg ccgtggcacc ctggtcactg tctcgagcgc ctctagcggg    360
gggagcacat caggaagcgg caagcccggt agcggcgaag ctcctctgg cagcgcccgc    420
tcctatgtgc tgactcagcc acccctcagt gtcagtggcc caggaaagac ggccaggatt    480
acctgtgggg gaaacaacat tggaagtaaa agtgtgcact ggtaccagca gaagccaggc    540
caggcccctg tgctggtcat ctattatgat agcgaccggc cctcagggat ccctgagcga    600
ttctctggct ccaactctgg gaacacggcc accctgacca tcagcagggt cgaagccggg    660
gatgaggccg actattactg tcaggtgtgg gacagtagta gtgatcacca agtcttcgga    720
actgggacca aggtcaccgt cctacgc                                       747

SEQ ID NO: 15            moltype = AA   length = 69
FEATURE                  Location/Qualifiers
source                   1..69
                         mol_type = protein
                         organism = Homo sapiens
SEQUENCE: 15
TTTPAPRPPT PAPTIASQPL SLRPEACRPA AGGAVHTRGL DFACDIYIWA PLAGTCGVLL    60
LSLVITLYC                                                           69

SEQ ID NO: 16            moltype = AA   length = 27
FEATURE                  Location/Qualifiers
source                   1..27
                         mol_type = protein
                         organism = Homo sapiens
SEQUENCE: 16
FWVLVVVGGV LACYSLLVTV AFIIFWV                                       27

SEQ ID NO: 17            moltype = AA   length = 24
FEATURE                  Location/Qualifiers
source                   1..24
                         mol_type = protein
                         organism = Homo sapiens
SEQUENCE: 17
IYIWAPLAGT CGVLLLSLVI TLYC                                          24

SEQ ID NO: 18            moltype = AA   length = 22
FEATURE                  Location/Qualifiers
source                   1..22
                         mol_type = protein
                         organism = Homo sapiens
SEQUENCE: 18
MLLLVTSLLL CELPHPAFLL IP                                            22
```

```
SEQ ID NO: 19          moltype = AA  length = 112
FEATURE                Location/Qualifiers
source                 1..112
                       mol_type = protein
                       organism = Homo sapiens
SEQUENCE: 19
RVKFSRSADA PAYQQGQNQL YNELNLGRRE EYDVLDKRRG RDPEMGGKPR RKNPQEGLYN    60
ELQKDKMAEA YSEIGMKGER RRGKGHDGLY QGLSTATKDT YDALHMQALP PR           112

SEQ ID NO: 20          moltype = AA  length = 15
FEATURE                Location/Qualifiers
source                 1..15
                       mol_type = protein
                       organism = synthetic construct
SEQUENCE: 20
GGGGSGGGGS GGGGS                                                     15

SEQ ID NO: 21          moltype = AA  length = 18
FEATURE                Location/Qualifiers
source                 1..18
                       mol_type = protein
                       organism = synthetic construct
SEQUENCE: 21
GSTSGSGKPG SGEGSTKG                                                  18

SEQ ID NO: 22          moltype = AA  length = 24
FEATURE                Location/Qualifiers
source                 1..24
                       mol_type = protein
                       organism = synthetic construct
SEQUENCE: 22
ASSGGSTSGS GKPGSGEGSS GSAR                                           24

SEQ ID NO: 23          moltype = AA  length = 20
FEATURE                Location/Qualifiers
source                 1..20
                       mol_type = protein
                       organism = Homo sapiens
SEQUENCE: 23
MALPVTALLL PLALLLHAAR                                                20

SEQ ID NO: 24          moltype = AA  length = 16
FEATURE                Location/Qualifiers
source                 1..16
                       mol_type = protein
                       organism = Homo sapiens
VARIANT                3
                       note = X = citrulline
VARIANT                11..12
                       note = X = citrulline
SEQUENCE: 24
STXSVSSSSY XXMFGG                                                    16

SEQ ID NO: 25          moltype = AA  length = 15
FEATURE                Location/Qualifiers
source                 1..15
                       mol_type = protein
                       organism = Homo sapiens
VARIANT                5
                       note = X = citrulline
VARIANT                10
                       note = X = citrulline
VARIANT                12
                       note = X = citrulline
SEQUENCE: 25
VYATXSSAVX LXSSV                                                     15

SEQ ID NO: 26          moltype = AA  length = 15
FEATURE                Location/Qualifiers
source                 1..15
                       mol_type = protein
                       organism = Homo sapiens
VARIANT                1
                       note = X = citrulline
VARIANT                13
                       note = X = citrulline
VARIANT                15
                       note = X = citrulline
```

```
SEQUENCE: 26
XPAPPPISGG GYXAX                                             15

SEQ ID NO: 27           moltype = AA  length = 19
FEATURE                 Location/Qualifiers
source                  1..19
                        mol_type = protein
                        organism = Homo sapiens
VARIANT                 7
                        note = X = citrulline
SEQUENCE: 27
SHQESTXGRS RGRSGRSGS                                         19

SEQ ID NO: 28           moltype = AA  length = 42
FEATURE                 Location/Qualifiers
source                  1..42
                        mol_type = protein
                        organism = Homo sapiens
SEQUENCE: 28
KRGRKKLLYI FKQPFMRPVQ TTQEEDGCSC RFPEEEEGGC EL                42

SEQ ID NO: 29           moltype = AA  length = 41
FEATURE                 Location/Qualifiers
source                  1..41
                        mol_type = protein
                        organism = Homo sapiens
SEQUENCE: 29
RSKRSRLLHS DYMNMTPRRP GPTRKHYQPY APPRDFAAYR S                 41

SEQ ID NO: 30           moltype = AA  length = 39
FEATURE                 Location/Qualifiers
source                  1..39
                        mol_type = protein
                        organism = Homo sapiens
SEQUENCE: 30
IEVMYPPPYL DNEKSNGTII HVKGKHLCPS PLFPGPSKP                    39

SEQ ID NO: 31           moltype = AA  length = 30
FEATURE                 Location/Qualifiers
source                  1..30
                        mol_type = protein
                        organism = Homo sapiens
SEQUENCE: 31
HLHLQESGPG LVKPSETLSL TCTVSGGSIN                              30

SEQ ID NO: 32           moltype = AA  length = 7
FEATURE                 Location/Qualifiers
source                  1..7
                        mol_type = protein
                        organism = Homo sapiens
SEQUENCE: 32
DTTYYWG                                                       7

SEQ ID NO: 33           moltype = AA  length = 14
FEATURE                 Location/Qualifiers
source                  1..14
                        mol_type = protein
                        organism = Homo sapiens
SEQUENCE: 33
WIRQPPGKGL EWIG                                               14

SEQ ID NO: 34           moltype = AA  length = 16
FEATURE                 Location/Qualifiers
source                  1..16
                        mol_type = protein
                        organism = Homo sapiens
SEQUENCE: 34
SIYYRGNTHY NSSLRS                                             16

SEQ ID NO: 35           moltype = AA  length = 32
FEATURE                 Location/Qualifiers
source                  1..32
                        mol_type = protein
                        organism = Homo sapiens
```

```
SEQUENCE: 35
RVTMSVDTSK NRFSLKVTSV TAADTAVYYC AR                             32

SEQ ID NO: 36           moltype = AA   length = 6
FEATURE                 Location/Qualifiers
source                  1..6
                        mol_type = protein
                        organism = Homo sapiens
SEQUENCE: 36
LDPFDY                                                          6

SEQ ID NO: 37           moltype = AA   length = 11
FEATURE                 Location/Qualifiers
source                  1..11
                        mol_type = protein
                        organism = Homo sapiens
SEQUENCE: 37
WGRGTLVTVS S                                                    11

SEQ ID NO: 38           moltype = AA   length = 22
FEATURE                 Location/Qualifiers
source                  1..22
                        mol_type = protein
                        organism = Homo sapiens
SEQUENCE: 38
SYVLTQPPSV SVAPGKTARI TC                                        22

SEQ ID NO: 39           moltype = AA   length = 11
FEATURE                 Location/Qualifiers
source                  1..11
                        mol_type = protein
                        organism = Homo sapiens
SEQUENCE: 39
GGNNIGSKSV H                                                    11

SEQ ID NO: 40           moltype = AA   length = 15
FEATURE                 Location/Qualifiers
source                  1..15
                        mol_type = protein
                        organism = Homo sapiens
SEQUENCE: 40
WYQQKPGQAP VLVIY                                                15

SEQ ID NO: 41           moltype = AA   length = 7
FEATURE                 Location/Qualifiers
source                  1..7
                        mol_type = protein
                        organism = Homo sapiens
SEQUENCE: 41
YDSDRPS                                                         7

SEQ ID NO: 42           moltype = AA   length = 32
FEATURE                 Location/Qualifiers
source                  1..32
                        mol_type = protein
                        organism = Homo sapiens
SEQUENCE: 42
GIPERFSGSN SGNTATLTIS RVEAGDEADY YC                             32

SEQ ID NO: 43           moltype = AA   length = 11
FEATURE                 Location/Qualifiers
source                  1..11
                        mol_type = protein
                        organism = Homo sapiens
SEQUENCE: 43
QVWDSSSDHQ V                                                    11

SEQ ID NO: 44           moltype = AA   length = 9
FEATURE                 Location/Qualifiers
source                  1..9
                        mol_type = protein
                        organism = Homo sapiens
SEQUENCE: 44
FGTGTKVTV                                                       9

SEQ ID NO: 45           moltype = AA   length = 16
FEATURE                 Location/Qualifiers
source                  1..16
                        mol_type = protein
```

```
                        organism = Homo sapiens
SEQUENCE: 45
STRSVSSSSY RRMFGG                                                        16

SEQ ID NO: 46           moltype = AA  length = 15
FEATURE                 Location/Qualifiers
source                  1..15
                        mol_type = protein
                        organism = Homo sapiens
SEQUENCE: 46
VYATRSSAVR LRSSV                                                         15

SEQ ID NO: 47           moltype = AA  length = 15
FEATURE                 Location/Qualifiers
source                  1..15
                        mol_type = protein
                        organism = Homo sapiens
SEQUENCE: 47
RPAPPPISGG GYRAR                                                         15

SEQ ID NO: 48           moltype = AA  length = 19
FEATURE                 Location/Qualifiers
source                  1..19
                        mol_type = protein
                        organism = Homo sapiens
SEQUENCE: 48
SHQESTRGRS RGRSGRSGS                                                     19
```